(12) United States Patent
Chou et al.

(10) Patent No.: US 11,156,606 B2
(45) Date of Patent: *Oct. 26, 2021

(54) HOMOGENEOUS ASSAY (II)

(71) Applicant: Essenlix Corporation, Monmouth Junction, NJ (US)

(72) Inventors: Stephen Chou, Princeton, NJ (US); Wei Ding, East Windsor, NJ (US); Ji Li, Princeton, NJ (US); Yufan Zhang, Monmouth Junction, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/961,880

(22) PCT Filed: Jan. 11, 2019

(86) PCT No.: PCT/US2019/013388
§ 371 (c)(1),
(2) Date: Jul. 13, 2020

(87) PCT Pub. No.: WO2019/140334
PCT Pub. Date: Jul. 18, 2019

(65) Prior Publication Data
US 2020/0363408 A1 Nov. 19, 2020

Related U.S. Application Data

(60) Provisional application No. 62/616,100, filed on Jan. 11, 2018.

(51) Int. Cl.
G01N 33/543 (2006.01)
C12Q 1/6804 (2018.01)
(Continued)

(52) U.S. Cl.
CPC ..... *G01N 33/54313* (2013.01); *C12Q 1/6804* (2013.01); *C12Q 1/6869* (2013.01);
(Continued)

(58) Field of Classification Search
CPC ....... G01N 33/54313; G01N 33/54386; G01N 33/54393; G01N 33/543; C12Q 1/6804;
(Continued)

(56) References Cited

U.S. PATENT DOCUMENTS 3,368,872 A 2/1968 Natelson
3,447,863 A 6/1969 Patterson
(Continued)

FOREIGN PATENT DOCUMENTS

AU 198813789 A 9/1988
AU 619459 B 1/1992
(Continued)

OTHER PUBLICATIONS

Written Opinion for PCT/US2019/013388 established by ISA/US dated Jun. 5, 2019.
(Continued)

*Primary Examiner* — Christopher L Chin

(57) ABSTRACT

Among other things, the present disclosure is related to devices and methods of performing biological and chemical assays, such as but not limited to immunoassays and nucleic assay acid, particularly a homogeneous assay that does not use a wash step and that is fast (e.g., 60 seconds from dropping a sample to displaying results). The present disclosure is related to both competitive and non-competitive homogeneous assays.

62 Claims, 25 Drawing Sheets

(51) Int. Cl.
*C12Q 1/6869* (2018.01)
*G06K 9/00* (2006.01)

(52) U.S. Cl.
CPC ... *G01N 33/54386* (2013.01); *G06K 9/00134* (2013.01); *G06K 9/00147* (2013.01)

(58) Field of Classification Search
CPC .............. C12Q 1/6869; C12Q 1/6837; G06K 9/00134; G06K 9/00147; B01L 3/5055
USPC ........ 356/244, 246; 422/401, 408, 425, 430, 422/551, 561, 563; 435/288.3, 288.7; 436/165, 534, 805, 807
See application file for complete search history.

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,083,761 A | 7/2000 | Kedar et al. |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Ivardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |

(56) References Cited

U.S. PATENT DOCUMENTS

| | | |
|---|---|---|
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0323330 A1 | 10/2014 | Bergo |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 0961110 A2 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991020009 | 12/1991 |
| WO | 1999042743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2011102903 A1 | 8/2011 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |
| WO | 2017048871 A1 | 3/2017 |
| WO | 2017112957 A1 | 6/2017 |

OTHER PUBLICATIONS

International Preliminary Report on Patentability for PCT/US2019/013388 established by ISA/US dated Jan. 27, 2020.

Written Opinion of the International Searching Authority for PCT/US2019/013388 established by the ISA/KR completed on Jun. 5, 2019.

International Preliminary Report on Patentability of the International Preliminary Examining Authority for PCT/US2019/013388 established by the IPEA/US completed on Jan. 27, 2020.

HOMOGENEOUS ASSAY (II)

CROSS REFERENCING

This application is a National Stage entry (§ 371) application of International Application No. PCT/US19/13388, filed Jan. 11, 2019, which claims the benefit of U.S. Provisional Patent Application No. 62/616,100, filed Jan. 11, 2018, the contents of which are relied upon and incorporated herein by reference in their entirety.

The entire disclosure of any publication or patent document mentioned herein is entirely incorporated by reference.

FIELD

The present disclosure is related to the field of bio/chemical sampling, sensing, assays and applications. Particularly, the present invention is related to bio/chemical assays, including, including immunoassays and nucleic acid assays.

BACKGROUND

In biological and chemical assays (e.g. diagnostic testing), a homogeneous assay, which does not comprise a wash step, is preferred. The present disclosure provides devices and methods for achieving these goals.

BRIEF SUMMARY

In some embodiments, the present invention takes, while the sample mixed with beads and without washing the sample, at two images of, a first image and a second image of a common area of the thin sample layer, wherein the common area of the thin sample layer is an area of the sample that contains at least one bead, wherein the first image is a direct image that measures position of a bead in the common area regardless if the bead captured a labeled competitive detection agent or not; and the second image is a signal image that is configured to measure signal from the labeled competitive detection agent. For example, the first image is a bright field image and ad the second image is fluorescence image.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A skilled artisan will understand that the drawings, described below, are for illustration purposes only. In some Figures, the drawings are in scale. In the figures that present experimental data points, the lines that connect the data points are for guiding a viewing of the data only and have no other means. For clarity purposes, some elements are enlarged when illustrated in the Figures. It should be noted that the Figures do not intend to show the elements in strict proportion. The dimensions of the elements should be delineated from the descriptions herein provided and incorporated by reference. The drawings are not intended to limit the scope of the present invention in any way.

16 illustrates some of the exemplary processes of the beads-enhanced speed test (BEST) for homogeneous nucleic acid hybridization assay, according to some embodiments of the present invention.

Figure 17A:
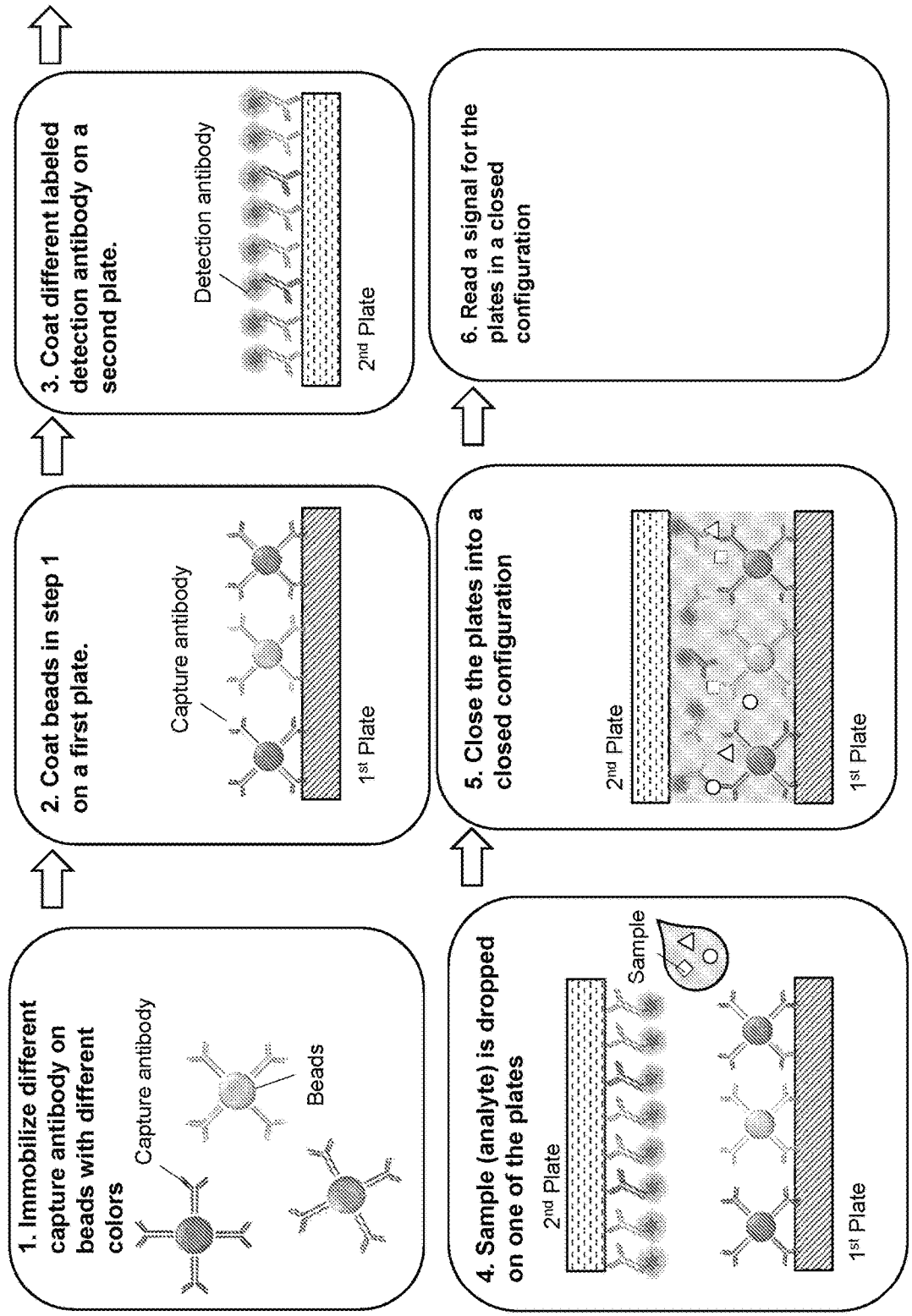
Figure 17B:
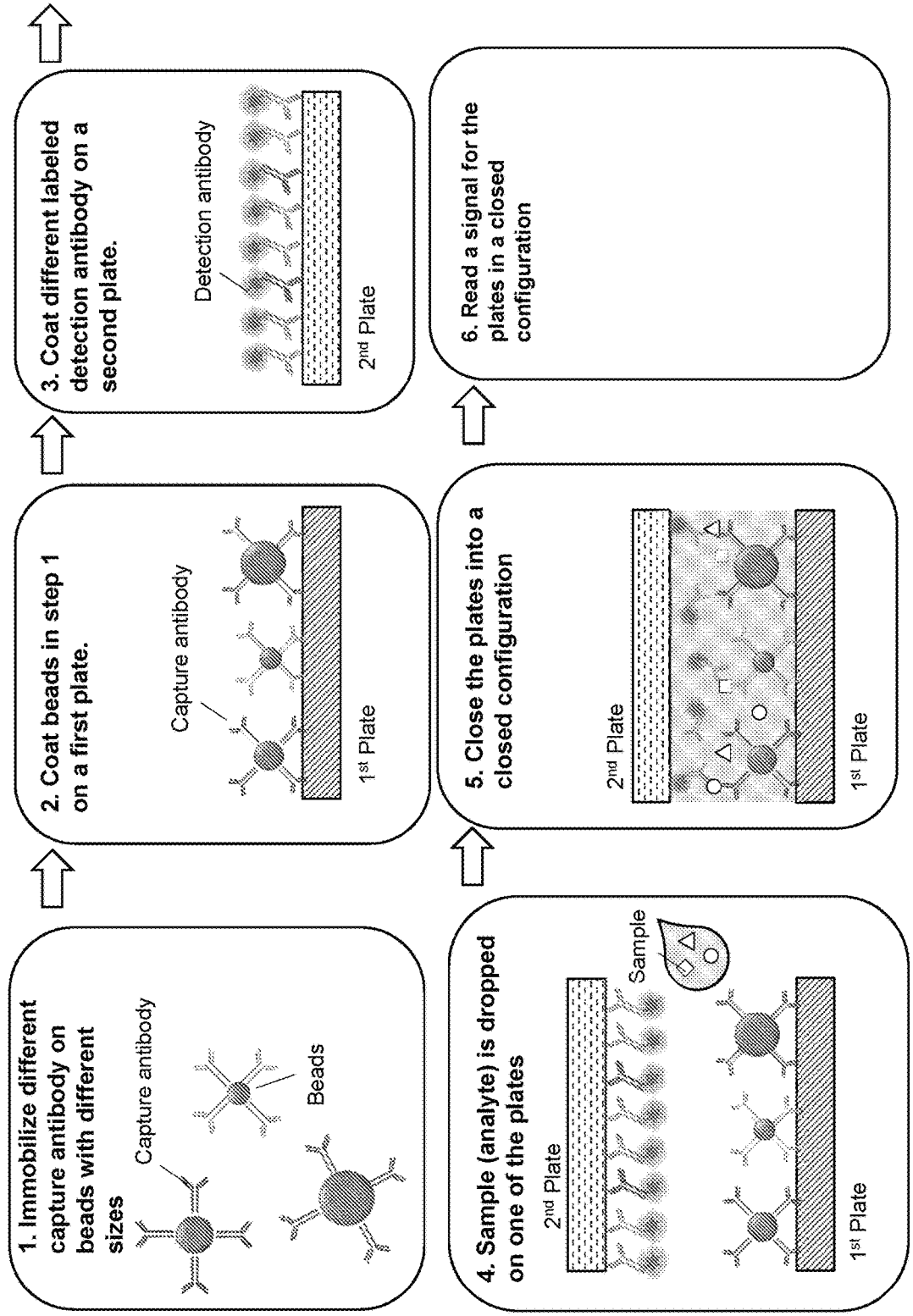
Figure 17C:
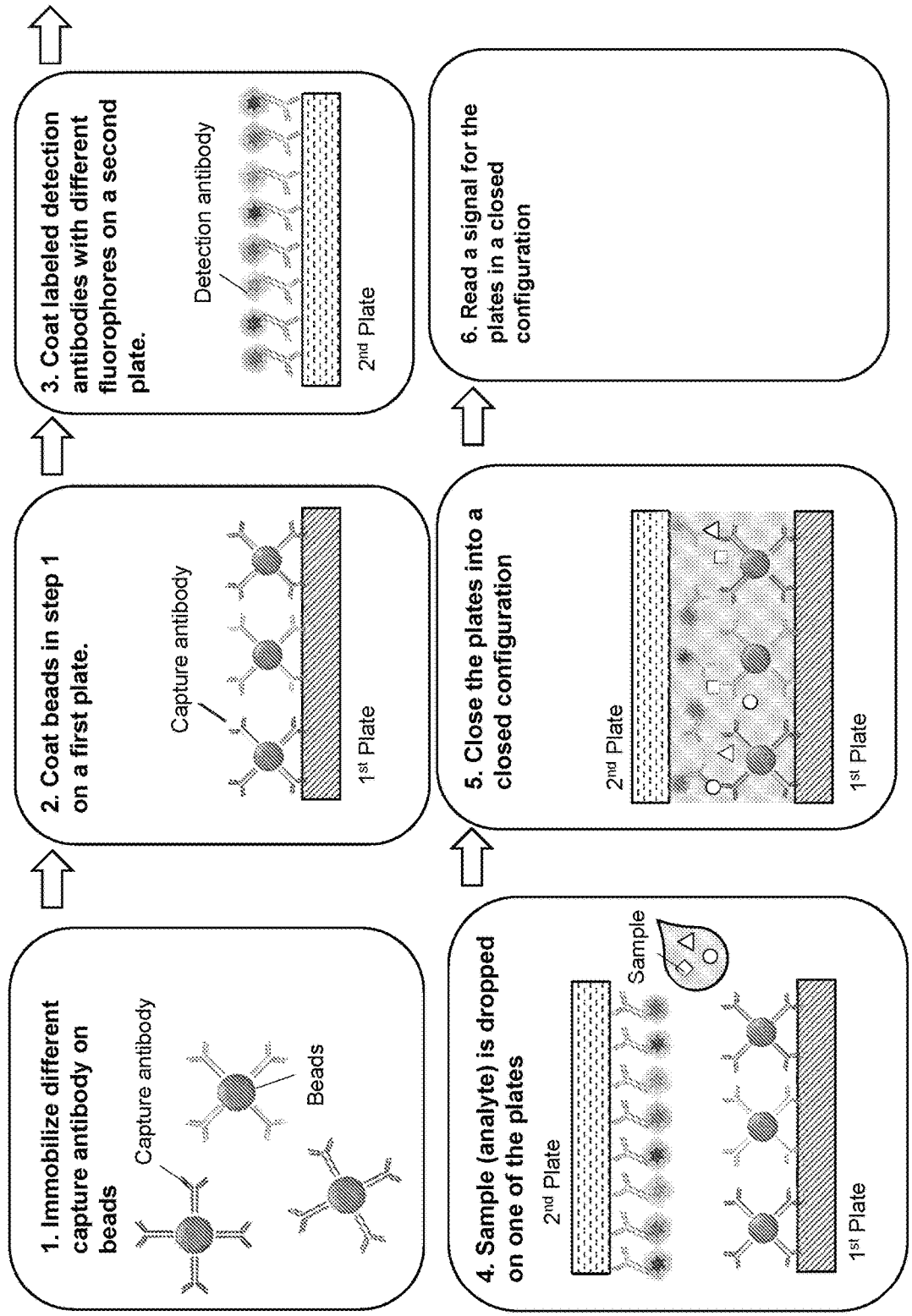

FIGS. 17A-C illustrate three different exemplary processes of multiplexed homogeneous immunoassays, respectively, according to some embodiments of the present invention.

Figure 18A:
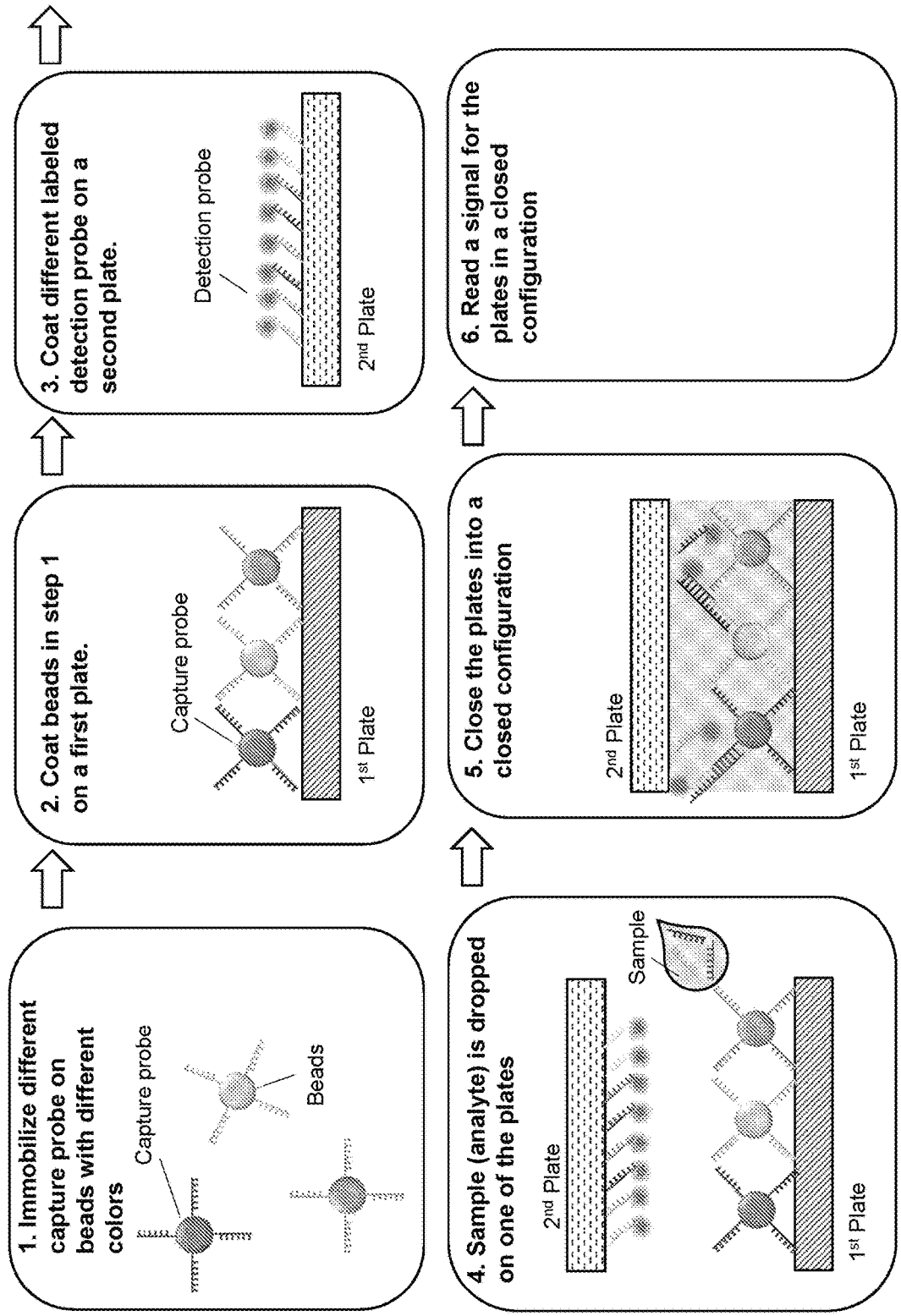
Figure 18B:
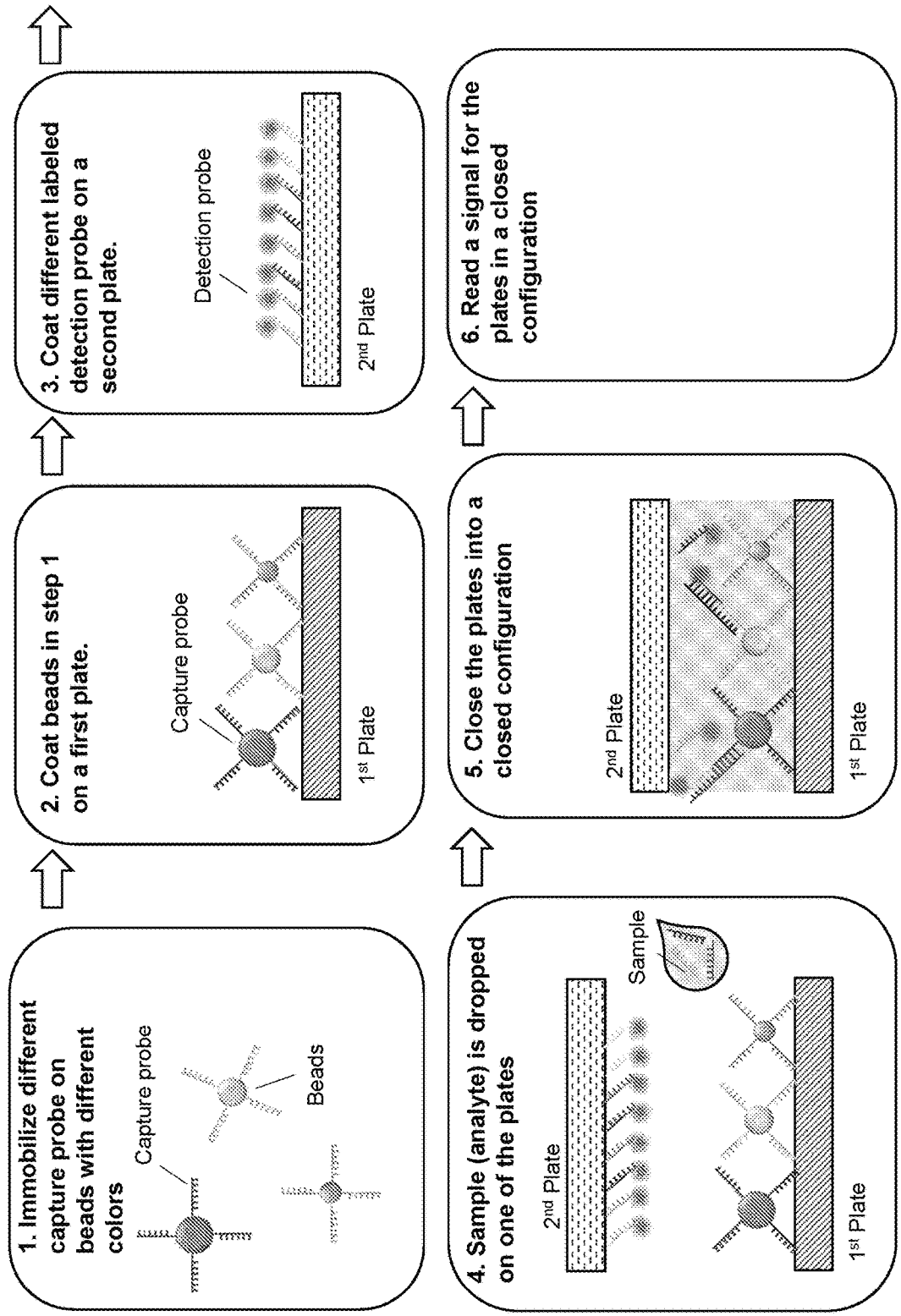
Figure 18C:
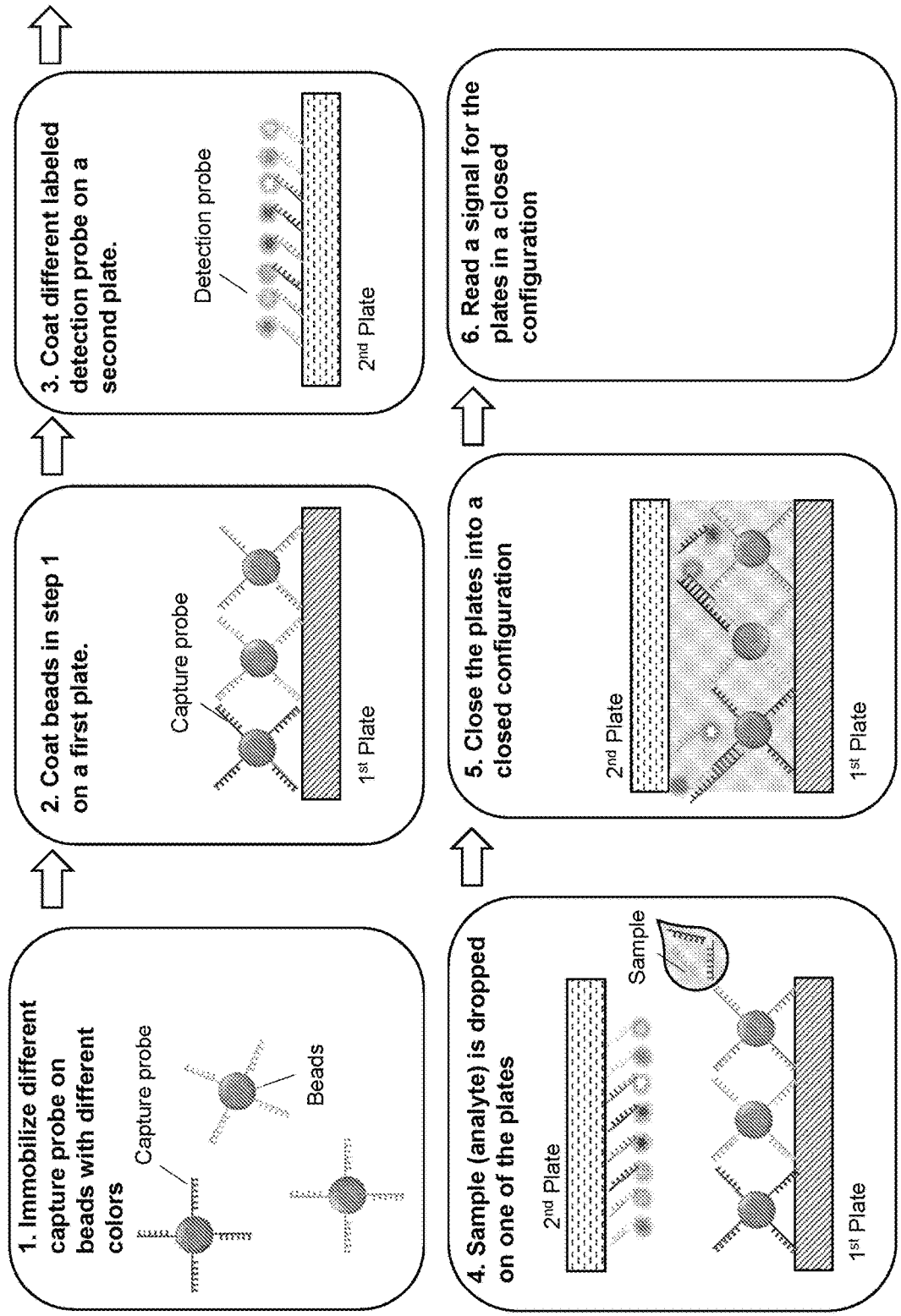

FIGS. 18A-C illustrate three different exemplary processes of multiplexed homogeneous nucleic acid hybridization assays, respectively, according to some embodiments of the present invention.

Figure 19:
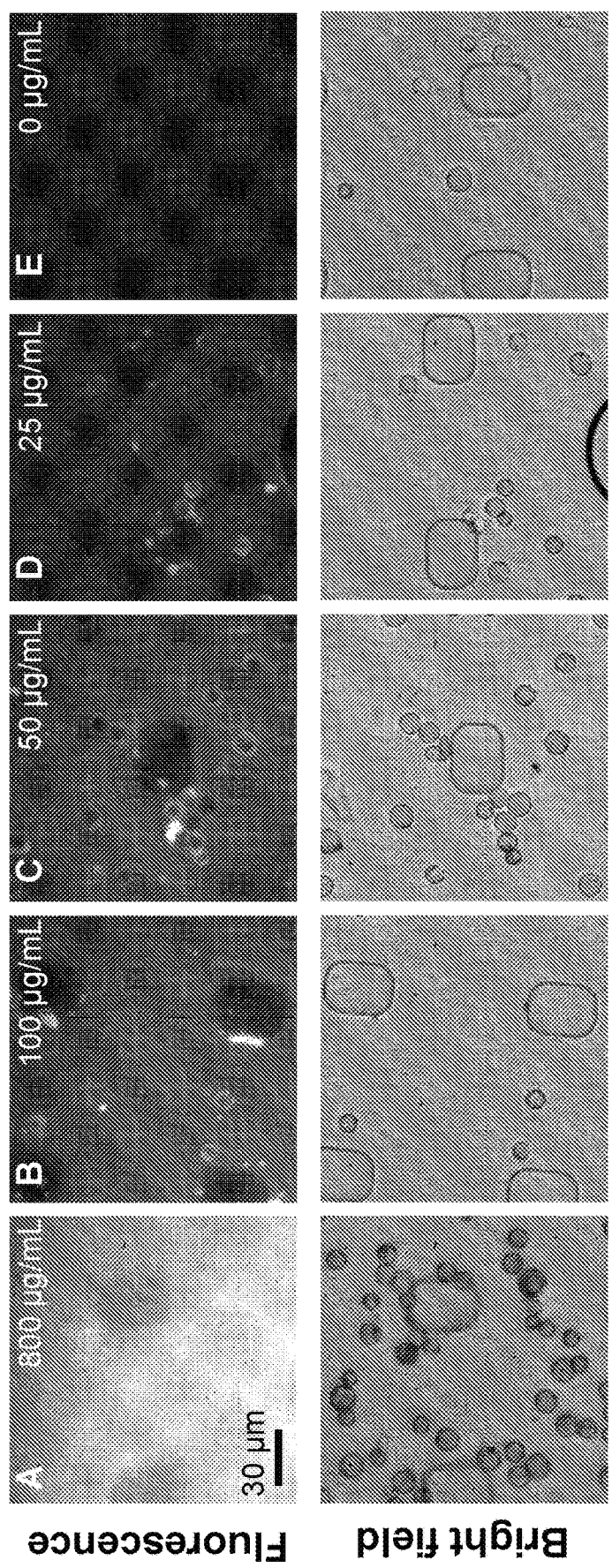

FIG. 19 illustrates exemplary fluorescence and bright-field images of the fluorescent stained beads inside a sample (e.g., solution) sandwiched between two plates, without washing away the sample. The spacers are visible in the bright field images.

DETAILED DESCRIPTION

The following detailed description illustrates certain embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The terms "labeled analyte" and "bound label" are interchangeable. The phrase "labeled analyte" refers to an analyte that is detectably labeled with a light emitting label such that the analyte can be detected by assessing the presence of the label. A labeled analyte may be labeled directly (e.g., the analyte itself may be directly conjugated to a label, e.g., via a strong bond, e.g., a covalent or non-covalent bond), or a labeled analyte may be labeled indirectly (e.g., the analyte is bound by a secondary capture agent that is directly labeled).

The terms "unbound label" and "background" are interchangeable, with understanding that the signal of "unbound label" includes signals from other background that are not "unbound label".

The term "lateral area" refers to the area that is in parallel with the plate.

The term "analyte-concentration area" refers to an area of a surface where the area has a higher affinity to bind the labeled analyte/bound label (or to bind an analyte what later binds a label) than the rest area of the surface.

The term "lateral distance between two neighboring analyte concentration areas" or "IACD (inter analyte concentration-area distance)" refers to the distance between the average center of each analyte concentration area. For example, if each of the analyte concentration area has a circular shape in lateral shape, the IACD is the distance between the centers of the two circles. Another example, if each of the two analyte concentration areas is a vertical plane, then the IACD is the lateral distance between the two planes.

The term "diffusion parameter" or "DP" as used herein refers to a parameter that is equal to $\sqrt{Dt}$, wherein D is the diffusion constant of the analyte in the sample and the t is the intended assay time (e.g., the diffusion parameter is equal to the square-root of the diffusion constant of the analyte in the sample multiplying the intended assay time); wherein the intended assay time is a time parameter. For example, if the diffusion constant of the analyte in the sample is $1\times10^{-7}$ cm2/s, the intended assay time is 60 sec, then the diffusion parameter is 24 um (micron). Some of the common analyte diffusion constants are IgG in PBS: $3\times10^{-7}$ cm2/s, IgG in blood: $1\times10^{-7}$ cm2/s, and 20 bp DNA in blood: $4\times10^{-7}$ cm2/s.

The term "bead" as used herein refers to a nano-scale or micro-scale three-dimensional object, regardless of its shape and material. The term "bead" and "particle" is interchangeable.

The term "specifically capture" means that a capture agent selectively bound an analyte that will be detected.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow") refers to a particular type of COF, wherein the final thickness of a part or entire sample after the compression is "regulated" by spacers, wherein the spacers, that are placed between the two plates.

The terms "specific binding" and "selective binding" refer to the ability of a capture agent to preferentially bind to a particular target molecule that is present in a heterogeneous mixture of different target molecule. A specific or selective binding interaction will discriminate between desirable (e.g., active) and undesirable (e.g., inactive) target molecules in a sample, typically more than about 10 to 100-fold or more (e.g., more than about 1000- or 10,000-fold).

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The term "capture agent" as used herein, refers to a binding member, e.g. nucleic acid molecule, polypeptide molecule, or any other molecule or compound, that can specifically bind to its binding partner, e.g., a second nucleic acid molecule containing nucleotide sequences complementary to a first nucleic acid molecule, an antibody that specifically recognizes an antigen, an antigen specifically recognized by an antibody, a nucleic acid aptamer that can specifically bind to a target molecule, etc. A capture agent may concentrate the target molecule from a heterogeneous mixture of different molecules by specifically binding to the target molecule. Binding may be non-covalent or covalent. The affinity between a binding member and its binding partner to which it specifically binds when they are specifically bound to each other in a binding complex is characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower KD.

The term "a secondary capture agent" which can also be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugation (Hermanson, "Bioconjugate Techniques" Academic Press, 2nd Ed., 2008).

The term "capture agent-reactive group" refers to a moiety of chemical function in a molecule that is reactive with capture agents, e.g., can react with a moiety (e.g., a hydroxyl, sulfhydryl, carboxyl or amine group) in a capture agent to produce a stable strong, e.g., covalent bond.

The term "antibody," as used herein, is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (σ), and alpha (α) which encode the IgM, IgD, IgG, IgE, and IgA antibody "isotypes" or "classes" respectively. Antibody herein is meant to include full length antibodies and antibody fragments, and may refer to a natural antibody from any organism, an engineered antibody, or an antibody generated recombinantly for experimental, therapeutic, or other purposes. The term "antibody" includes full length antibodies, and antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies.

The terms "antibody epitope," "epitope," "antigen" are used interchangeably herein to refer to a biomolecule that is bound by an antibody. Antibody epitopes can include proteins, carbohydrates, nucleic acids, hormones, receptors, tumor markers, and the like, and mixtures thereof. An antibody epitope can also be a group of antibody epitopes, such as a particular fraction of proteins eluted from a size exclusion chromatography column. Still further, an antibody epitope can also be identified as a designated clone from an expression library or a random epitope library.

An "allergen," as used herein is a substance that elicits an allergic, inflammatory reaction in an individual when the individual is exposed to the substance, e.g., by skin contact, ingestion, inhalation, eye contact, etc. An allergen may include a group of substances that together elicit the allergic reaction. Allergens may be found in sources classified by the following groups: natural and artificial fibers (cotton, linen, wool, silk, teak, etc., wood, straw, and other dust); tree pollens (alder, birch, hazel, oak, poplar, palm, and others); weeds and flowers (ambrosia, artemisia, and others); grasses and corns (fescue, timothy grass, rye, wheat, corn, bluegrass, and others); drugs (antibiotics, antimicrobial drugs, analgetics and non-steroid anti-inflammatory drugs, anesthetics and muscle relaxants, hormones, and others); epidermal and animal allergens (epithelium of animals, feathers of birds, sera, and others); molds and yeasts (*Penicillium* notation, *Cladosporium* spp., *Aspergillus fumigatus, Mucor racemosus,* and others); insect venoms; preservatives (butylparaben, sorbic acid, benzoate, and others); semen (ejaculate); parasitic and mite allergens (ascarids, *Dermatophagoides pteronyssinus, Dermatophagoides farinae, Euroglyphus maynei,* and others); occupational and hobby allergens (coffee beans, formaldehyde, latex, chloramine, dyes, and others); food allergens (egg products, dairy products and cheeses, meat products, fish and seafood, soy products, mushrooms, flours and cereals, vegetables, melons and gourds, beans, herbs and spices, nuts, citrus and other fruits, berries, teas and herbs, nutritional supplements, and other products), etc.

The term "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these.

As is known to one skilled in the art, hybridization can be performed under conditions of various stringency. Suitable hybridization conditions are such that the recognition interaction between a capture sequence and a target nucleic acid is both sufficiently specific and sufficiently stable. Conditions that increase the stringency of a hybridization reaction are widely known and published in the art. See, for example, Green, et al., (2012), infra.

The term "protein" refers to a polymeric form of amino acids of any length, e.g., greater than 2 amino acids, greater than about 5 amino acids, greater than about 10 amino acids, greater than about 20 amino acids, greater than about 50 amino acids, greater than about 100 amino acids, greater than about 200 amino acids, greater than about 500 amino acids, greater than about 1000 amino acids, greater than about 2000 amino acids, usually not greater than about 10,000 amino acids, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Also included by these terms are polypeptides that are post-translationally modified in a cell, e.g., glycosylated, cleaved, secreted, prenylated, carboxylated, phosphorylated, etc., and polypeptides with secondary or tertiary structure, and polypeptides that are strongly bound, e.g., covalently or non-covalently, to other moieties, e.g., other polypeptides, atoms, cofactors, etc.

The term "complementary" as used herein refers to a nucleotide sequence that base-pairs by hydrogen bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarily may be calculated to assess the possibility of a non-specific (off-target) binding. In general, a complementary of 50% or less does not lead to non-specific binding. In addition, a complementary of 70% or less may not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 200 nucleotides and up to 300 nucleotides in length, or longer, e.g., up to 500 nucleotides in length or longer. Oligonucleotides may be synthetic and, in certain embodiments, are less than 300 nucleotides in length.

The term "attaching" as used herein refers to the strong, e.g., covalent or non-covalent, bond joining of one molecule to another.

The term "surface attached" as used herein refers to a molecule that is strongly attached to a surface.

The term "sample" as used herein relates to a material or mixture of materials containing one or more analytes or entity of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The term "analyte" refers to a molecule (e.g., a protein, peptides, DNA, RNA, nucleic acid, or other molecule), cells, tissues, viruses, and nanoparticles with different shapes.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminescence. An external excitation can be a combination of the above.

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wiley & Sons, 2002).

The term "specific binding conditions" and "conditions suitable for binding," as used herein with respect to binding of a capture agent to an analyte, e.g., a biomarker, a biomolecule, a synthetic organic compound, an inorganic compound, etc., refers to conditions that produce nucleic acid duplexes or, protein/protein (e.g., antibody/antigen) complexes, protein/compound complexes, aptamer/target complexes that contain pairs of molecules that specifically bind to one another, while, at the same time, disfavor to the formation of complexes between molecules that do not specifically bind to one another. Specific binding conditions are the summation or combination (totality) of both hybridization and wash conditions, and may include a wash and blocking steps, if necessary. For nucleic acid hybridization, specific binding conditions can be achieved by incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 ug/ml denatured, sheared salmon sperm DNA, followed by washing the filters in 0.1×SSC at about 65° C.

For binding of an antibody to an antigen, specific binding conditions can be achieved by blocking a first plate containing antibodies in blocking solution (e.g., PBS with 3% BSA or non-fat milk), followed by incubation with a sample containing analytes in diluted blocking buffer. After this incubation, the first plate is washed in washing solution (e.g. PBS+TWEEN 20) and incubated with a secondary capture antibody (detection antibody, which recognizes a second site in the antigen). The secondary capture antibody may be conjugated with an optical detectable label, e.g., a fluorophore such as IRDye8000 W, Alexa 790, Dylight 800. After another wash, the presence of the bound secondary capture antibody may be detected. One of skill in the art would be knowledgeable as to the parameters that can be modified to increase the signal detected and to reduce the background noise.

A subject may be any human or non-human animal. A subject may be a person performing the instant method, a patient, a customer in a testing center, etc.

An "analyte," as used herein is any substance that is suitable for testing in the present invention.

As used herein, a "diagnostic sample" refers to any biological sample that is a bodily byproduct, such as bodily fluids, that has been derived from a subject. The diagnostic sample may be obtained directly from the subject in the form of liquid, or may be derived from the subject by first placing the bodily byproduct in a solution, such as a buffer. Exemplary diagnostic samples include, but are not limited to, saliva, serum, blood, sputum, urine, sweat, lacrima, semen, feces, breath, biopsies, mucus, etc.

As used herein, an "environmental sample" refers to any sample that is obtained from the environment. An environmental sample may include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. Typically, samples that are not in liquid form are converted to liquid form before analyzing the sample with the present invention.

As used herein, a "foodstuff sample" refers to any sample that is suitable for animal consumption, e.g., human consumption. A foodstuff sample may include raw ingredients, cooked food, plant and animal sources of food, preprocessed food as well as partially or fully processed food, etc. Typically, samples that are not in liquid form are converted to liquid form before analyzing the sample with the present invention.

The term "diagnostic," as used herein, refers to the use of a method or an analyte for identifying, predicting the outcome of and/or predicting treatment response of a disease or condition of interest. A diagnosis may include predicting the likelihood of or a predisposition to having a disease or condition, estimating the severity of a disease or condition, determining the risk of progression in a disease or condition, assessing the clinical response to a treatment, and/or predicting the response to treatment.

A "biomarker," as used herein, is any molecule or compound that is found in a sample of interest and that is known to be diagnostic of or associated with the presence of or a predisposition to a disease or condition of interest in the subject from which the sample is derived. Biomarkers include, but are not limited to, polypeptides or a complex thereof (e.g., antigen, antibody), nucleic acids (e.g., DNA, miRNA, mRNA), drug metabolites, lipids, carbohydrates, hormones, vitamins, etc., that are known to be associated with a disease or condition of interest.

A "condition" as used herein with respect to diagnosing a health condition, refers to a physiological state of mind or body that is distinguishable from other physiological states. A health condition may not be diagnosed as a disease in some cases. Exemplary health conditions of interest include, but are not limited to, nutritional health; aging; exposure to environmental toxins, pesticides, herbicides, synthetic hormone analogs; pregnancy; menopause; andropause; sleep; stress; prediabetes; exercise; fatigue; chemical balance; etc. The term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least 10−8M. A biotin affinity agent may also include a linker, e.g., -LC-biotin, -LC-LC-Biotin, -SLC-Biotin or -PEGn-Biotin where n is 3-12.

The term "streptavidin" refers to both streptavidin and avidin, as well as any variants thereof that bind to biotin with high affinity.

The term "marker", as used in describing a biological sample, refers to an analyte whose presence or abundance in a biological sample is correlated with a disease or condition.

The term "bond" includes covalent and non-covalent bonds, including hydrogen bonds, ionic bonds and bonds produced by van der Waal forces.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

The term "entity" refers to, but not limited to proteins, peptides, DNA, RNA, nucleic acid, molecules (small or large), cells, tissues, viruses, nanoparticles with different shapes, that would bind to a "binding site". The entity includes the capture agent, detection agent, and blocking agent. The "entity" includes the "analyte", and the two terms are used interchangeably.

The term "binding site" refers to a location on a solid surface that can immobilize "entity" in a sample.

The term "entity partners" refers to, but not limited to proteins, peptides, DNA, RNA, nucleic acid, molecules (small or large), cells, tissues, viruses, nanoparticles with different shapes, that are on a "binding site" and would bind to the entity. The entity, include, but not limited to, capture agents, detection agents, secondary detection agents, or "capture agent/analyte complex".

The term "target analytes" or "target entity" refers to a particular analyte that will be specifically analyzed (e.g., detected), or a particular entity that will be specifically bound to the binding site.

The term "smart phone" or "mobile phone", which are used interchangeably, refers to the type of phones that has a camera and communication hardware and software that can take an image using the camera, manipulate the image taken by the camera, and communicate data to a remote place. In some embodiments, the Smart Phone has a flash light.

The term "light" refers to, unless specifically specified, an electromagnetic radiation with various wavelength.

The term "average linear dimension" of an area is defined as a length that equals to the area times 4 then divided by the perimeter of the area. For example, the area is a rectangle, that has width w, and length L, then the average of the linear dimension of the rectangle is 4*W*L/(2*(L+W)) (where "*"

means multiply and "/" means divide). By this definition, the average line dimension is, respectively, W for a square of a width W, and d for a circle with a diameter d. The area include, but not limited to, the area of a binding site or a storage site.

The term "period" of periodic structure array refers to the distance from the center of a structure to the center of the nearest neighboring identical structure.

The term "storage site" refers to a site of an area on a plate, wherein the site contains reagents to be added into a sample, and the reagents are capable of being dissolving into the sample that is in contract with the reagents and diffusing in the sample.

The term "relevant" means that it is relevant to detection of analytes, quantification and/or control of analyte or entity in a sample or on a plate, or quantification or control of reagent to be added to a sample or a plate.

The term "hydrophilic", "wetting", or "wet" of a surface means that the contact angle of a sample on the surface is less than 90 degree.

The term "hydrophobic", "non-wetting", or "does not wet" of a surface means that the contact angle of a sample on the surface is equal to or larger than 90 degrees.

The term "variation" of a quantity refers to the difference between the actual value and the desired value or the average of the quantity. And the term "relative variation" of a quantity refers to the ratio of the variation to the desired value or the average of the quantity. For example, if the desired value of a quantity is Q and the actual value is (Q+μ), then the μ is the variation and the μ/(Q+μ) is the relative variation. The term "relative sample thickness variation" refers to the ratio of the sample thickness variation to the average sample thickness.

The term "optical transparent" refers to a material that allows a transmission of an optical signal, wherein the term "optical signal" refers to, unless specified otherwise, the optical signal that is used to probe a property of the sample, the plate, the spacers, the scale-marks, any structures used, or any combinations of thereof.

The term "none-sample-volume" refers to, at a closed configuration of a CROF process, the volume between the plates that is occupied not by the sample but by other objects that are not the sample. The objects include, but not limited to, spacers, air bubbles, dusts, or any combinations of thereof. Often none-sample-volume(s) is mixed inside the sample.

The term "saturation incubation time" refers to the time needed for the binding between two types of molecules (e.g. capture agents and analytes) to reach an equilibrium. For a surface immobilization assay, the "saturation incubation time" refers the time needed for the binding between the target analyte (entity) in the sample and the binding site on plate surface reaches an equilibrium, namely, the time after which the average number of the target molecules (the entity) captured and immobilized by the binding site is statistically nearly constant.

In some cases, the "analyte" and "binding entity" and "entity" are interchangeable.

A "processor," "communication device," "mobile device," refer to computer systems that contain basic electronic elements (including one or more of a memory, input-output interface, central processing unit, instructions, network interface, power source, etc.) to perform computational tasks. The computer system may be a general purpose computer that contains instructions to perform a specific task, or may be a special-purpose computer.

A "site" or "location" as used in describing signal or data communication refers to the local area in which a device or subject resides. A site may refer to a room within a building structure, such as a hospital, or a smaller geographically defined area within a larger geographically defined area. A remote site or remote location, with reference to a first site that is remote from a second site, is a first site that is physically separated from the second site by distance and/or by physical obstruction. The remote site may be a first site that is in a separate room from the second site in a building structure, a first site that is in a different building structure from the second site, a first site that is in a different city from the second site, etc.

As used herein, "raw data" includes signals and direct read-outs from sensors, cameras, and other components and instruments which detect or measure properties or characteristics of a sample. For example, raw data includes voltage or current output from a sensor, detector, counter, camera, or other component or device; raw data includes digital or analog numerical output from a sensor, detector, counter, camera, or other component or device; and raw data may include digitized or filtered output from a sensor, detector, counter, camera, or other component or device. For example, raw data includes the output of a luminometer, which may include output in "relative light units" which are related to the number of photons detected by the luminometer. Raw data may include a JPEG, bitmap, or other image file produced by a camera. Raw data may include cell counts; light intensity (at a particular wavelength, or at or within a range of wavelengths); a rate of change of the output of a detector; a difference between similar measurements made at two times; a number of events detected; the number of events detected within a pre-set range or that meet a pre-set criterion; the minimum value measured within a time period, or within a field of view; the maximum value measured within a time period, or within a field of view; and other data. Where sufficient, raw data may be used without further processing or analysis. In other cases, raw data may be further processed or used for further analysis related to the sample, the subject, or for other purposes.

"Representative of a sample" as used in reference to an output signal or raw data that are representative of the sample, refers to the output signal or raw data reflecting a measured property of the sample or a portion thereof, e.g., reflecting the amount of analyte of interest present in the sample. For instance, the intensity of a fluorescence signal representative of a sample may be more intense in a fluorescently labeled sample that contains more analyte of interest than the intensity of a fluorescence signal representative of a fluorescently labeled sample that contains less analyte.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible. One skilled artisan will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

Homogeneous Competitive Assays Using Dual Imaging

According to the present invention, an homogenous competitive assay comprises a sample chamber with two plates that sandwich a sample suspect containing an analyte, one or more particles that have a capture agent attached to the surface of the particles, wherein the capture agent specifically bind to the analyte, and a labeled competitive detection agent, wherein the labeled competing detection agent competes with the analyte, if present, for binding to the capture agent for the analyte.

According to the present invention, in certain embodiments, a method for performing a competitive assay of an analyte in a liquid sample, comprising:

(a) providing a sample that contains or is suspected of containing an analyte;

(b) providing one or more beads that have a capture agent attached onto the surface of the one or more beads, wherein the capture agent specifically binds to the analyte;

(c) providing a labeled competitive detection agent, wherein the labeled competing detection agent competes with the analyte, if present, for binding to the capture agent;

(d) providing a sample holder that is configured to make the sample into a thin layer;

(e) having the sample in the sample holder and making the sample forming a thin layer having a thickness of 200 um or less, wherein the one or more beads and the labeled competitive detection agent are mixed with the sample;

(f) taking, after step (e), without washing the sample, at least two images, including a first image and a second image, of a common area of the sample layer, wherein the common area of the sample layer is an area of the sample that contains at least one bead, wherein the first image is a direct image for measuring a position of a bead in the common area; and the second image is a signal image for measuring a signal from the labeled competitive detection agent;

(g) after (f), comparing and analyzing the first image and the second image to identify the signal at the one or more beads;

wherein the beads have various shape and have a maximum dimension in the range of 0.05 um to 50 um, wherein the spacing between the inner surfaces of the two plates is configured such that in the common area (i) the sample layer has uniform thickness, and (ii) the one or more beads do not overlap with each other in a direction normal to the sample layer such that when viewing from the top of the sample layer, no bead substantially blocks a view of any other bead.

In some embodiments, a method for performing a competitive assay of an analyte in a liquid sample, comprising:

(a) providing a sample that contains or is suspected of containing an analyte;

(b) providing one or more beads that have a capture agent attached onto the surface of the beads;

(c) providing a labeled competitive detection agent, wherein the labeled competitive detection agent specifically binds to the analyte and the capture agent, and wherein the capture agent competes with the analyte, if present, for binding to the labeled competing detection agent;

(d) providing a sample holder that is configured to make the sample into a thin layer having a thickness of 200 um or less;

(e) having the sample in the sample holder and making the sample forming a thin layer, wherein the beads and the labeled competitive detection agent are mixed with the sample;

(f) taking, after step (e), without washing the sample, at least two images, including a first image and a second image, of a common area of the thin sample layer, wherein the common area of the thin sample layer is an area of the sample that contains at least one bead, wherein the first image is a direct image for measuring a position of a bead in the common area; and the second image is a signal image for measuring a signal from the labeled competitive detection agent;

(g) after (f), comparing and analyzing the first image and the second image to identify the signal at the beads;

wherein the beads have various shape and have a maximum dimension in the range of 0.05 um to 50 um, wherein the spacing between the inner surfaces of the two plates is configured such that in the common area (i) the sample layer has uniform thickness, and (ii) the one or more beads do not overlap with each other in a direction normal to the sample layer such that when viewing from the top of the sample layer, no bead substantially blocks a view of any other bead.

In some embodiments, a method for assaying an analyte in a liquid using beads, comprising:

(a) depositing a sample that contains or is suspected of containing an analyte, into a sample holder, said sample holder comprising:
  i. a first plate; and
  ii. a second plate;
     wherein the first plate and the second plate are movable relative to each other into:
  i. an open configuration in which the first plate and the second plate are at least partially separated such that the sample can be deposited therebetween; and
  ii. a closed configuration, in which the first plate is placed on top of the second plate thereby compressing at least a portion of the sample between the first plate and the second plate into a layer having uniform thickness of 200 um or less;

(b) having the plates into a closed configuration, wherein the sample is mixed with (i) one or more beads comprising a capture agent attached onto a surface thereof; and (ii) a labeled competitive detection agent; and (c) taking, after step (b), while the plates are in the closed configuration and without washing the sample, at least two images, including a first image and a second image, of a common area of the sample layer, wherein the common area of the sample layer is an area of the sample that contains at least one bead, wherein the first image is a direct image for measuring a position of a bead in the common area, and wherein the second image is a signal image for measuring a signal from the labeled competitive detection agent;

(d) after (c), comparing and analyzing the first image and the second image to identify the signal at the beads;

wherein the beads have various shape and have a maximum dimension in the range of 0.05 um to 50 um, wherein the spacing between the inner surfaces of the two plates is configured such that in the common area (i) the sample layer has uniform thickness, and (ii) the one or more beads do not overlap with each other in a direction normal to the sample layer such that when viewing from the top of the sample layer, no bead substantially blocks a view of any other bead.

In some embodiments, a kit for performing a competitive assay for analyzing an analyte in a sample, comprising:

a first plate, a second plate, one or plurality of beads, a capture agent, and a labeled competing detection agent, wherein:
  i. the plates are movable relative to each other into different configurations;
  ii. each of the plates has, on its respective surface, a sample contact area for contacting a sample that contains an analyte;

iii. the beads have a capture agent attached onto the surface of the beads, wherein the capture agent specifically bind to the analyte;
iv. the labeled competing detection agent competes with the analyte, if present, for binding to the capture agent for the analyte;
v. beads have a capture agent attached on their surface and have a [maximum] size of 0.2 um to 100 um;
wherein one of the configurations is an open configuration, in which: the two plates are separated apart, and the sample is deposited on one or both plate;
wherein another of the configurations is a closed configuration which is configured after the sample deposition in the open configuration; and in the closed configuration: at least part of the sample is compressed by the two plates into a layer of highly uniform thickness of 200 um or less and is substantially stagnant relative to the plates; and
wherein at the closed configuration, the detector detects the analyte in the at least part of the sample.

In some embodiments, a kit for performing a competitive assay for analyzing an analyte in a sample, comprising:
a first plate, a second plate, one or plurality of beads, a capture agent, a labeled competing detection agent, and spacers wherein:
i. the plates are movable relative to each other into different configurations;
ii. each of the plates has, on its respective surface, a sample contact area for contacting a sample that contains an analyte;
iii. the beads have a capture agent attached to the surface of the beads, wherein the capture agent specifically bind to the analyte;
iv. the labeled competing detection agent competes with the analyte, if present, for binding to the capture agent for the analyte;
v. the spacers are on one or both plate, wherein the spacers are fixed on one of the plate and has flat top, and in at least one of the spacers is in the sample area;
vi. beads have a capture agent attached on their surface and have a [maximum] size of 0.2 um to 100 um;
wherein one of the configurations is an open configuration, in which: the two plates are separated apart, the spacing between the plates is not regulated by the spacers, and the sample is deposited on one or both of the plates; and
wherein another of the configurations is a closed configuration which is configured after the sample deposition in the open configuration; and in the closed configuration: at least part of the sample is compressed by the two plates into a layer of highly uniform thickness of 200 um or less and is substantially stagnant relative to the plates, wherein the uniform thickness of the layer is confined by the inner surfaces of the two plates and is regulated by the plates and the spacers.

In some embodiments, an apparatus for analyzing an analyte in a sample, comprising:
a. an imager or imagers that is configured to take a direct illumination image and an oblique illumination image of a thin layer of a sample having a thickness of 200 um or less; wherein each of the two imagers images at least a common area of the sample, wherein the sample contains an analyte and one or plurality of beads, wherein the beads have a capture agent attached on their surface and have a [maximum] size of 0.2 um to 100 um, wherein the capture agent captures the analyte, and wherein at least one of the beads is in the common area of the sample; and b. a hardware and a software that are configured to (a) identify the common area of the sample from the direct illumination image and the oblique illumination image, (b) identify the beads in the common area of the sample in direct illumination image, (c) measure, using the info in b., the light amplitude at each pixels related to the nanobeads.

2. A method for competitive assaying an analyte in a liquid sample, comprising:
(a) providing a sample that contains or is suspected of containing an analyte;
(b) providing a sample holder of any device of prior claims;
(c) providing one or more beads that have a capture agent attached onto the surface of the beads, wherein the capture agent specifically bind to the analyte;
(d) providing a labeled competitive detection agent, wherein the labeled competing detection agent competes with the analyte, if present, for binding to the capture agent for the analyte,
(e) having the sample in the sample holder and making the sample forming a thin layer having a thickness of 200 um or less, wherein the beads and the labeled competitive detection agent are mixed with the sample;
(f) taking, after step (e), two images of a common area of the thin sample layer, wherein the common area of the sample layer is an area of the sample contains at least one bead, wherein one of the images is a direct image that comprises information of the topology (i.e. geometry) and position of the bead in the common area; and the other image is a signal image that is configured to comprises signal from the labeled competitive detection agents as a major signal of the image;
(g) after (f), comparing and analyzing the two images and using an algorithm to identify the signal at the beads;
wherein the beads have various shape and has a maximum dimension in the range of 0.05 um to 50 um, where in the spacing between the two plate inner surface is configured, so that in the thin layer of the sample, the beads do not have overlap each other in the direction in normal to the thin sample layer.

In some embodiments, a method for competitive assaying an analyte in a liquid sample, comprising:
(a) providing a sample that is suspected of containing an analyte;
(b) providing a sample holder of any device of prior claims and an apparatus of any prior claims;
(c) providing one or more beads that have a capture agent attached to the surface of the beads, wherein the capture agent specifically bind to the analyte;
(d) providing a labeled competitive detection agent, wherein the labeled competing detection agent competes with the analyte, if present, for binding to the capture agent for the analyte,
(e) having the sample in the sample holder and making the sample forming a thin layer having a thickness of 200 um or less, wherein the beads and the labeled competitive detection agent are mixed with the sample;
(f) taking, after step (e), two images of a common area of the thin sample layer, wherein the common area of the sample layer is an area of the sample contains at least one bead, wherein one of the images is a direct image that comprises information of the topology (i.e. geometry) and position of the bead in the common area; and the other image is a signal image that is configured to comprises signal from the labeled competitive detection agents as a major signal of the image;

(g) after (f), comparing and analyzing the two images and using an algorithm to identify the signal at the beads;

wherein the bead have various shape and has a maximum dimension in the range of 0.05 um to 50 um, where in the spacing between the two plate inner surface is configured, so that in the thin layer of the sample, the beads do not have overlap each other in the direction in normal to the thin sample layer.

The device, kit, apparatus, and method of any prior embodiment, wherein the direct image is bright field image.

The device, kit, apparatus, and method of any prior embodiment, wherein the direct image is an image formed with an illumination from an angle about normal to the sample thin layer (0 to 30 degree from the normal).

The device, kit, apparatus, and method of any prior embodiment, wherein the signal image is a dark field image.

The device, kit, apparatus, and method of any prior embodiment, wherein the signal image is a fluorescence image.

The device, kit, apparatus, and method of any prior embodiment, wherein the signal image is a luminescence image.

The device, kit, apparatus, and method of any prior embodiment, wherein the signal image is an image formed with an illumination from an angle about parallel to the sample thin layer (0 to 30 degree from the sample plane).

The device, kit, apparatus, and method of any prior embodiment, wherein the assay is homogenous assay that measures the analyte does not use any no wash.

The device, kit, apparatus, and method of any prior embodiment, wherein the signal is an optical signal.

The device, kit, apparatus, and method of any prior embodiment, wherein the images have many pixels that are configured to identify the signals.

The device, kit, apparatus, and method of any prior embodiment, wherein the plate has a spacer to control the final sample thickness in measuring the signal.

The device, kit, apparatus, and method of any prior embodiment, wherein the total assay time is less than 10 sec, 20 sec, 30 sec, 40 sec, 50 sec, 60 sec, 120 sec, 180 sec, 240 sec, 300 sec, 400 sec, 500 sec, 1000 sec, or 2000 sec.

FIG. 1 illustrates an exemplary QMAX BEST competitive immunoassay.

1. Bead Preparation 1.1. Anti-BSA Antibody Preparation

100 μg of anti-BSA antibody (from Rockland, Cat. 201-4133-0100) was buffer exchanged with PBS buffer using Ultracel 0.5 mL 30 k Membrane (from Millipore, Cat. UFC503008) for three times according to manufacture's protocol. 100 g of anti-BSA antibody was finally diluted in 50 μL of PBS buffer at a concentration of 2 mg/mL.

1.2. 10 μm Bead Preparation 100 of 10 μm PureProteome NHS FlexiBind Magnetic Bead (from Millipore Sigma, Cat. NO. LSKMAGN4) was transferred to a 1.5 mL microcentrifuge tube. Beads were collected at the bottom of the tube using a magnet, and the storage buffer was discarded using a pipette. Beads were then immediately rinsed with ice-cold Equilibration Buffer (1 mM HCl, provided by manufacture) and vortexed vigorously for 20 s. Beads were collected at the bottom of the tube using a magnet, and the Equilibration Buffer was discarded using a pipette.

1.3. 10 μm Bead and Antibody Coupling

Immediately mixed 50 μL of anti-BSA antibody from Step 1.1 with beads from Step 1.2. Incubated beads with continuous mixing on a vortex overnight at 4° C. Beads were then collected at the bottom of the tube using a magnet and the unbounded anti-BSA antibody was removed using a pipette. Resuspended and washed the beads with 500 μL of Quench Buffer (100 mM Tris-HCl, 150 mM NaCl, pH 8.0) for three times. Incubated the beads with 500 μL of Quench Buffer at room temperature for 1 h. Beads were then washed three times with 500 μL PBS and stored in PBS at 4° C. for further use.

1.4. Morphine-BSA Competitor Coating

PBS buffer of beads from Step 1.3 was discarded with a pipette. Beads were then incubated with 50 g of Morphine-BSA with continuous mixing on a vortex for 8 h at room temperature. Beads were collected at the bottom of the tube using a magnet and the unbounded Morphine-BSA was discarded using a pipette. Beads were then washed three times with 500 μL PBS as described above.

1.5. Blocking

Beads from Step 1.4 were incubated with 4% BSA overnight at 4° C. Beads were then washed three times with 500 μL PBS as described above, and stored in 100 μL PBS at 4° C. for further use.

2. First Plate Preparation

Beads from Step 1.5 were sonicated for 2 minutes before use. Bead density was adjusted to approximately 5 beads in each 10^4 μm² pillar of view. 1 μL of beads was then dropped on the surface of the first plate (with 10 μm pillars), and dried in a desiccator at room temperature.

3. Second Plate Preparation 300 g of anti-Morphine antibody (from Fitzgerald, Cat. 10-1379) was labeled with Cy5® using Abcam Cy5® fast conjugation kit according to the manufacture's protocol. The second plate, made by PMMA, was first incubated with 1% NaOH at 42° C. for 2 h, and then rinsed three times with water before incubated with 4% BSA at room temperature for 2 h. The second plate was then rinsed three times with PBS and air dried before use.

1 μL of Cy5 labeled anti-Morphine antibody was dropped and dried on the second plate in a desiccator at room temperature.

4. Morphine QMAX BEST Competitive Immunoassay

1 μL of PBS or artificial saliva spiked with certain concentrations of morphine was dropped on the first plate where beads were dried at Step 2. The first plate and the second plate were then closed into a closed configuration, and incubated for 1 min.

5. Imaging Analysis

Without washing, QMAX card was directly measured in a closed configuration using either a microscope or a smartphone. In some embodiments, the present invention takes, while the sample mixed with beads and without washing the sample, at two images of, a first image and a second image of a common area of the thin sample layer, wherein the common area of the thin sample layer is an area of the sample that contains at least one bead, wherein the first image is a direct image that measures position of a bead in the common area regardless if the bead captured a labeled competitive detection agent or not; and the second image is a signal image that is configured to measure signal from the labeled competitive detection agent. For example, the first image is a bright field image and ad the second image is fluorescence image. In some embodiments, the two type of images are taken at the same location simultaneously.

Figure 2:
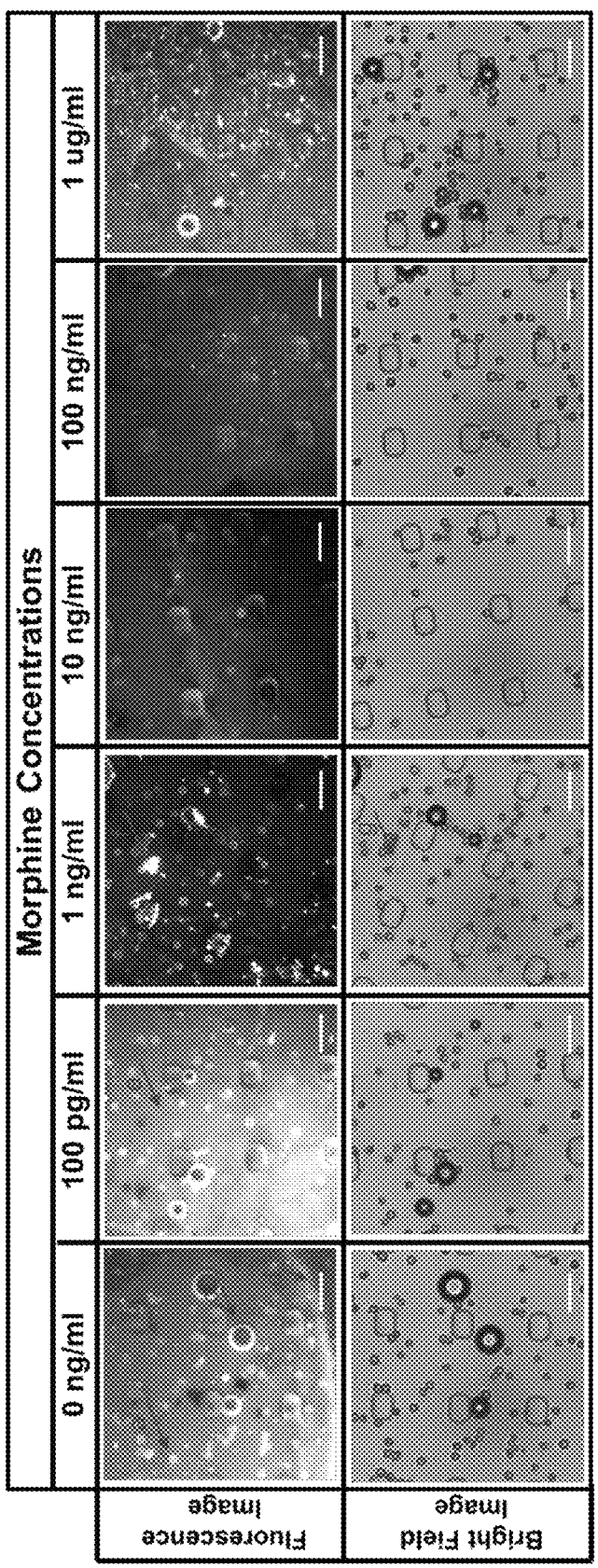
FIG. 2 illustrates fluorescence images and corresponding bright field images at the same location using different concentrations of morphine spiked in PBS buffer. The spacers are visible in the bright field images.

Examples of the experimental demonstration of the present inventions are given in FIGS. 2 and 19.

6. Analyte Analysis

In assaying the analytes, the analyte can be detected by either analogy means (analog BEST) or digital means (digital BEST). In analog BEST, the analyte amount in the sample is determined from the total amplitude of the light from all beads in the measurement area. While in a digital BEST, the analyte amount in the sample is determined from the number of the beads that have a light signal above a threshold value, wherein the threshold value is determined from a calibration and wherein as long as the light from a bead is equal or above the threshold it counts one bead regardless how much it is above the threshold.

Certain Preferred Specifications

1. Particles (beads) can have a diameter of 100 nm, 500 nm, 1 µm, 5 µm, 50 µm, 100 µm, or a range between any two of the values; and a preferred range of 0.5 µm to 10 µm, or 10 µm to 20 µm, or 20 µm to 50 µm.
2. Particles or beads can be polystyrene, polypropylene, polycarbonate, glass, metal or any other material whose surface can be modified to bind antibodies.
3. The diameter of the beads should be no larger than the pillar height of the first plate. Preferably, the diameter of the beads is similar as the pillar height of the first plate.
4. Labels can be fluorescent, colorimetric or luminescent.
5. Sample type please refers to Homogeneous Immunoassay Provisional.
6. QMAX card please refers to Homogeneous immunoassay Provisional.

FIG. 2 illustrates fluorescence images and corresponding bright field images at the same location using different concentrations of morphine spiked in PBS buffer. As shown in FIG. 2, images were taken by fluorescence microscope coupled with a mercury lamp. Scale bar represents 50 µm. (a) and (b) are 10 µm beads with different fluorescence intensities due to variations in bead coating procedure and local detection antibody concentration. (c) is an air bubble with false positive fluorescence signal resulted from light scattering, which can be excluded by software when compared with a corresponding bright field image. (d) and (h) shows fluorescence signal from undissolved fluorescence labeled anti-Morphine detection antibody. (e) is the background fluorescence signal from dissolved but unbounded fluorescence labeled anti-Morphine detection antibody. (f) and (g) shows a broken 10 µm bead which exhibits false positive fluorescence signal due to light scattering. The broken bead can be distinguished by the software when compared with a corresponding bright field image, and thus excluded from the image analysis.

Examples of Optical Systems

Figure 3:
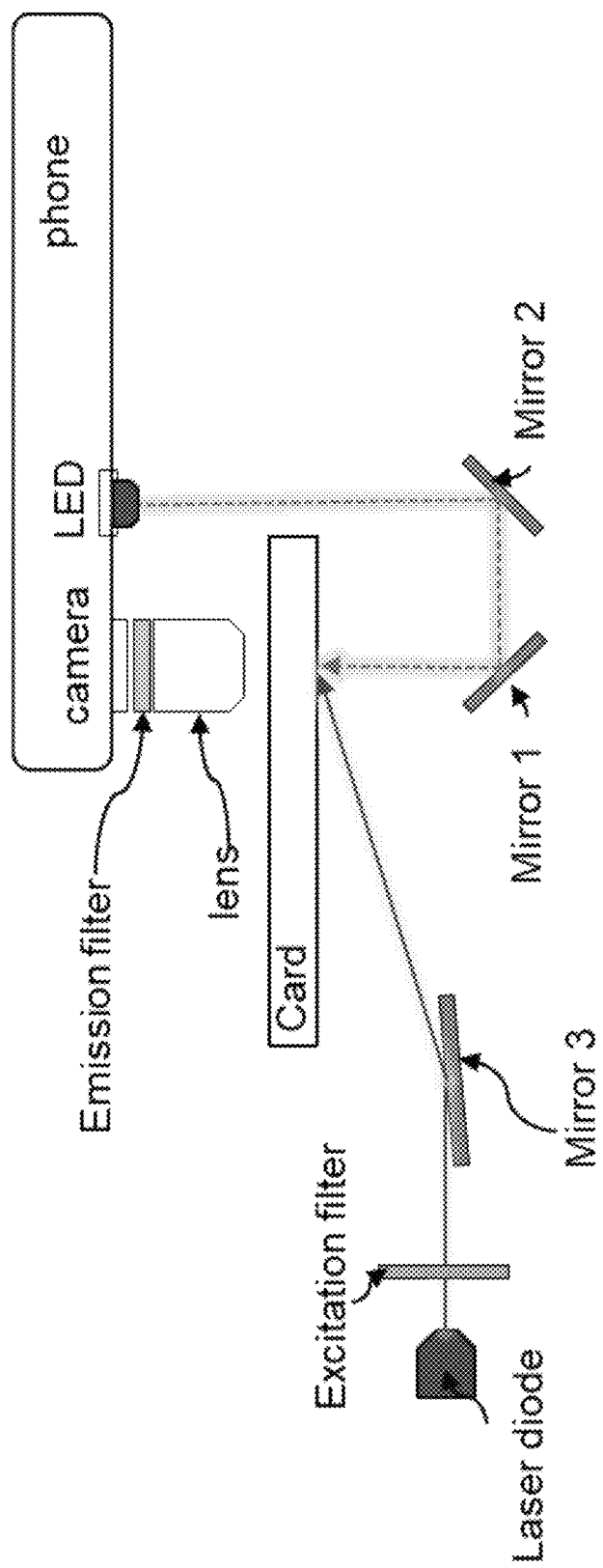
FIG. 3 illustrates an example of a QMAX card reader (or adapter), which reads both the bright field signal and fluorescence signal at the same spot of a QMAX card.

FIG. 3 illustrates an example of a QMAX card reader (or adapter), which reads both the bright field signal and fluorescence signal at the same spot of a QMAX card. In an example, the card reader uses a smartphone as both the camera and the bright field light source, and a laser diode as the fluorescence light source.

In observing the bright field signal on the QMAX card, the LED light on the smartphone is reflected by two 45-degree mirrors (mirror 1 and mirror 2), which are both underneath the QMAX card, and illuminates on the observing spot on the QMAX card from its back side. The observing spot of the QMAX card is directly underneath the smartphone camera. An emission filter and a focus lens are attached at the front of the smartphone camera. In one example, the emission filter is a 670 nm long pass filter. The lens has a focus distance around 4 mm and a numerical aperture of 0.2. The typical bright field lighting up area is a circle with a diameter of 1 mm to 5 mm. The typical observing field of view for bright field is 1 mm2 to 25 mm2.

In observing the fluorescence signal on the QMAX card, the laser light from a laser diode is reflected by a mirror (mirror 3) and illuminates on the observing spots on the QMAX card from its back side with a light incident angle to the card between 5 degree to 20 degree. There is an excitation filter at the front of the laser diode to clean up the excitation light. Optional, there is an optical lens in front of the laser diode to generate line profile of the laser light. In an example, the laser diode has a 638 nm central wavelength with 120 mW power. The excitation filter is a 650 nm short pass filter. Same as the bright field, the observing spot of the QMAX card is directly underneath the smartphone camera. An emission filter and a focus lens are attached at the front of the smartphone camera. The typical fluorescence lighting up area is a square with a size of 1 mm2 to 25 mm2. The typical observing field of view for fluorescence is 1 mm2 to 25 mm2.

In observing both the bright field and fluorescence signal at the same spot of a QMAX card, the laser diode is open first, and the smartphone camera takes the fluorescence signal from the objects on the QMAX card. Immediately after the fluorescence signal is taken, the smartphone LED is open, and the smartphone camera takes the bright field signal from the objects on the QMAX card at the same spot. Typical bright field signal taking parameters are ISO 400 to 800, integration time 1/200 s to 1/50 s. Typical fluorescence taking parameters are ISO 800 to 1600, integration time 1/3 s to 1 s.

In observing both the bright field and fluorescence signal at the same spot of a QMAX card, the smartphone LED is open first, and the smartphone camera takes the bright field signal from the objects on the QMAX card. Immediately after the bright field signal is taken, the smartphone LED is closed, and the laser diode is open, and the smartphone camera takes the fluorescence signal from the objects on the QMAX card at the same spot. Typical bright field signal taking parameters are ISO 400 to 800, integration time 1/200 s to 1/50 s. Typical fluorescence taking parameters are ISO 800 to 1600, integration time 1/3 s to 1 s.

Alternatives to the setup:

In some embodiments, mirror 1 and mirror 2 are replaced by one mirror with a tilted angle between 20 degree to 40 degree to reflect the LED light on the back of QMAX card.

In some embodiments, mirror 3 can be deleted in the setup, and the laser diode directly illuminate on the QMAX card from its back side with a light incident angle to the card between 5 degree to 20 degree.

In some embodiments, there is a focus lens between the QMAX card and mirror 1 to magnify the field of view of bright field. In an example, the lens has a focus distance of 4 mm to 6 mm and a numerical aperture of 0.1 to 0.3 and 1 to 4 mm away underneath the QMAX card.

In some embodiments, a QMAX card reader (or adapter) reads both the bright field signal and fluorescence signal at the same spot of a QMAX card within a time frame of 0.5 to 1.0 second.

In some embodiments, the smartphone LED, mirror 1 and mirror 2 are all replaced by an external LED directly underneath the QMAX card.

In some embodiments, a pair of polarizers are used. The first polarizer was put between the laser diode and the excitation filter, or between the excitation filter and mirror 3, or between mirror 3 and card. The second polarizer is between the lens and the card. The orientation of the polarizer is tuned to make the polarization of the one polarizer is perpendicular to that of the other.

In some embodiments, an optical system observing objects on card using bright field and fluorescence, comprising: a smartphone; and an optical reader. In some embodiments, the optical system of any prior embodiments, wherein the optical reader comprises: a lens; a receptacle slot that is configured to receive and position the QMAX card in a sample slide in the field of view and focal range of the camera of smartphone; a bright-field illumination optics that is configured to capture bright-field images of the sample on QMAX card; a fluorescent illumination optics that is configured to capture fluorescent images of the sample on QMAX card; In some embodiments, the optical system of any prior embodiments, wherein the bright-field illumination optics comprises. In some embodiments, a LED light source, where in the light source can be from the smartphone or an individual light source.

In some embodiments, a pair of 45-degree mirrors, wherein the two 45-degree mirrors which are both underneath the QMAX card, and deflect the light from the LED to illuminate on the observing spot on the QMAX card from its back side;

In some embodiments, the optical system of any prior embodiments, wherein the fluorescence illumination optics comprises: an emission filter; a laser diode light source; an excitation filter; a mirror; a lens; wherein the mirror deflects the laser light beam to illuminate on the observing spots on the QMAX card from its back side with a light incident angle to the card of 5 degree, 10 degree, 15 degree, 20 degree, 25 degree, or in a range between any of the two values.

In some embodiments, the central wavelength of the laser diode can be a 405 nm, 450 nm, 525 nm, 532 nm, 635 nm, 638 nm; and the output optical power can be 10 mW, 20 mW, 30 mW, 50 mW, 100 mW, 150 mW, 200 mW, or in a range between any of the two values.

wherein the excitation filter is at the front of the laser diode to clean up the excitation light;

wherein the emission filter is put between the lens and smartphone camera to block the excitation laser light and to allow the fluorescence signal to go through.

In some embodiments, the optical system of any prior embodiments, wherein the fluorescence illumination optics comprises:
   an emission filter;
   a laser diode light source;
   an excitation filter;
   a mirror;
   a lens;
   a pair of polarizers;
   wherein the mirror deflects the laser light beam to illuminate on the observing spots on the QMAX card from its back side with a light incident angle to the card of 5 degree, 10 degree, 15 degree, 20 degree, 25 degree, or in a range between any of the two values;
   wherein the central wavelength of the laser diode can be a 405 nm, 450 nm, 525 nm, 532 nm, 635 nm, 638 nm; and the output optical power can be 10 mW, 20 mW, 30 mW, 50 mW, 100 mW, 150 mW, 200 mW, or in a range between any of the two values;
   wherein the excitation filter is at the front of the laser diode to clean up the excitation light;
   wherein the emission filter is put between the lens and smartphone camera to block the excitation laser light and to allow the fluorescence signal to go through;
   wherein the first polarizer was put between the laser diode and the excitation filter, or between the excitation filter and mirror, or between mirror and QMAX card, and the second polarizer is between the lens and the QMAX card, and the orientation of the polarizer is tuned to make the polarization of the one polarizer is perpendicular to that of the other.

In some embodiments, the optical system of any prior embodiments, wherein the focal length of the lens can be 1 mm, 2 mm, 4 mm, 6 mm, 10 mm, 20 mm, 30 mm, or in a range between any of the two values.

In some embodiments, the optical system of any prior embodiments, wherein the excitation filter can be a 650 nm short pass filter with the use of a laser diode with central wavelength of 638 nm.

In some embodiments, the optical system of any prior embodiments, wherein the emission filter can be a 670 nm long pass filter with the use of a laser diode with central wavelength of 638 nm.

In some embodiments, a method of imaging objects on QMAX card in bright-filed illumination, comprising:
   a. Insert the QMAX card comprising the sample into the optical reader;
   b. Turn on LED light on the smartphone to illuminate on the observing spot on the QMAX card from its back side;
   c. Turn on the camera of smartphone;
   d. adjust the lens position of camera of the smartphone to make the sample on QMAX card focused;
   e. take an image with proper exposure setting.

In some embodiments, the method of imaging objects on QMAX card in fluorescence illumination, comprising:
   a. Insert the QMAX card comprising the sample into the optical reader;
   b. Turn on the laser diode light source;
   c. Turn on the camera of smartphone;
   d. adjust the lens position of camera of the smartphone to make the sample on QMAX card focused;
   e. take an image with proper exposure setting.

11. A method of imaging objects on QMAX card in both bright-field illumination and fluorescence illumination, comprising:
   a. Insert the QMAX card comprising the sample into the optical reader;
   b. Turn on LED light on the smartphone to illuminate on the observing spot on the QMAX card from its back side;
   c. Turn on the camera of smartphone;
   d. adjust the lens position of camera of the smartphone to make the sample on QMAX card focused;
   e. take an image with proper exposure setting.
   f. Turn off the LED of smartphone and keep smartphone camera on;
   g. Turn on the laser diode;
   h. adjust the lens position of camera of the smartphone to make the sample on QMAX card focused;
   i. take an image with proper exposure setting.

12. The method of embodiment 11, wherein both the bright field signal and fluorescence images are taken within a time frame of 0.5 to 1.0 second 13. The method of any of prior embodiments, wherein the typical fluorescence taking parameters are ISO 800 to 1600, integration time $\frac{1}{3}$ s to 1 s.

14. The method of any of prior embodiments, wherein the typical bright field signal taking parameters are ISO 400 to 800, integration time $\frac{1}{200}$ s to $\frac{1}{50}$ s.

Alternatives to the Setup:

In some embodiments, mirror 1 and mirror 2 are replaced by one mirror with a tilted angle between 20 degree to 40 degree to reflect the LED light on the back of QMAX card.

In some embodiments, mirror 3 can be deleted in the setup, and the laser diode directly illuminate on the QMAX card from its back side with a light incident angle to the card between 5 degree to 20 degree.

In some embodiments, there is a focus lens between the QMAX card and mirror 1 to magnify the field of view of bright field. In an example, the lens has a focus distance of 4 mm to 6 mm and a numerical aperture of 0.1 to 0.3 and 1 to 4 mm away underneath the QMAX card.

In some embodiments, a QMAX card reader (or adapter) reads both the bright field signal and fluorescence signal at the same spot of a QMAX card within a time frame of 0.5 to 1.0 second.

In some embodiments, the smartphone LED, mirror 1 and mirror 2 are all replaced by an external LED directly underneath the QMAX card.

Homogeneous Non-Competitive Assays Using Local Amplification

In certain embodiments, a homogenous non-competitive assay competitive assay can comprise a sample holder that is configured to make a sample suspected having an analyte into a thin layer. In certain embodiments, in a homogenous non-competitive assay competitive assay one capture surface of the sample holder can have a capture agent that specifically captures an analyte in a sample, and one non-capture surface that does not have the capture agent, wherein the capture by the capture agent is by binding to one part of the analyte. In certain embodiments, a homogenous non-competitive assay competitive assay can comprise a labeled detection agent that specifically captures an analyte, wherein the capture by the detection agent is by bingeing to another part of the analyte. In certain embodiments, a homogenous non-competitive assay competitive assay can comprise a capture surface that is to configured to amplify the optical signal of the detection agent, wherein the amplification is by one or any combination of the following: (a) directly amplifying the label optical signal using metallic structures (i.e. plasmonic structures), including micro and nanostructures, or metal/dielectric mixtures; (b) putting a light emitters (e.g. fluorophore) that emit the same or similar wavelength range of light as the labeled detection agent on or near the capture area; or (c) any combination of (a) and (b). The amplification makes the capture area brighter than the non-capture area to overcome some background signal in a homogenous assay.

EXAMPLES

1. Principles and Certain Examples

One objective of the present invention is to perform a homogeneous assay in "one step". The "one step" assay means that in assaying, one drops a sample on the assay and then reads the signal, and there are no other steps in between (e.g. washing). The assays include, but not limited to, protein assays and nucleic acid assays.

Another objective of the present invention is to perform a "one step" assay in a time frame of about 60 seconds or less. The time is defined as the time from a sample touching the assay plate to the signal of the assay being ready to be read.

The present invention is to allow performing a homogeneous assay in "one-step" without using any washing, often being completed in about 60 seconds or less. In the "one-step" assay, it uses two plates that are movable relative to each other, a sample with an analyte is dropped on one or both of the plates, the two plates are pressed against each other to compress at least a portion of the sample into a thin layer, followed by reading the signal from the plate without any washing. Often the time, from the sample touching one of the plates to reading the signal from the plate is about 60 sec or less.

Another important feature of the present invention is that in certain embodiments, the two plates of the assay are pressed by human hands, and by using particular set of the plates and the spacers, as specified herein, at least a portion of the sample have a uniform thickness.

EXAMPLES

According to one embodiment of the present invention, as shown in FIG. 1, a device for a homogeneous assay, comprising:

a first plate, a second plate, spacers, a plurality of particles, and capture agents, wherein:
 i. the first and second plates are movable relative to each other into different configurations, including an open configuration and a closed configuration;
 ii. each of the plates has, on its respective inner surface, a sample contact area for contacting a sample suspected of containing a analyte;
 iii. the first plate comprises the spacers that are fixed on its inner surface, at least one of the spacers is inside the sample contact area, the spacers have a predetermined substantially uniform height that is equal to 100 um or less;
 iv. the plurality of particles has the capture agents immobilized on their surface, wherein the capture agents are capable of specifically binding and immobilizing the analyte; and
 v. the plurality of particles are (a) distributed on the sample contact area of the first plate, except the areas occupied by the spacers, and (b) are temporarily or permanently fixed on the first plate;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

According to one embodiment of the present invention, a device for a homogeneous assay, comprising:

a first plate, a second plate, spacers, a plurality of particles, and capture agents, wherein:
 i. the first and second plates are movable relative to each other into different configurations, including an open configuration and a closed configuration;
 ii. each of the plates has, on its respective inner surface, a sample contact area for contacting a sample suspected of containing a analyte;
 iii. one or both plates comprises the spacers that are fixed on its inner surface, at least one of the spacers is inside the sample contact area, the spacers have a predetermined substantially uniform height that is equal to 100 um or less;
 iv. the plurality of particles has the capture agents immobilized on their surface, wherein the capture agents are capable of specifically binding and immobilizing the analyte; and
 v. the plurality of particles are (a) distributed on a sample contact area of the first, and (b) are temporarily or permanently fixed on the plate;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

Another objective of the present invention is to perform homogenous assays accurately by (1) measuring the total optical signal for an particle area and the total optical signal from its neighboring area, and by (2) averaging several pairs of the particle area and its surrounding area.

According to one embodiment of the present invention, a method of performing a homogeneous assay, comprising the steps of:
  (a) obtaining a sample suspected of containing an analyte;
  (b) obtaining a device of any prior embodiment, wherein the capture agents are capable of specifically binding an binding site of the analyte;
  (c) having optical labels on at least a part of the sample contact areas of the device, wherein the optical labels are capable of binding to the analytes;
  (d) depositing the sample on one or both of the plates when the plates are in an open configuration, wherein in an open configuration;
  (e) after (d), bringing the two plates together and pressing the plates into a closed configuration, at least part of the sample is compressed by the two plates into a layer of highly uniform thickness, the uniform thickness of the layer is confined by the inner surfaces of the plates and is regulated by the plates and the spacers;
  (f) while the plates are in the closed configuration, analyzing the analyte in the layer of uniform thickness, wherein the analyzing comprises:
    i. measuring, from outside of the sample layer, the total light signal from (a) a particle area that is an area of the sample layer that contains one particle and from (b) a surrounding area that is the area of the sample layer which is around the particle area, wherein the surrounding area is 50 D within the edge of the particle, wherein the D is the diameter of the particle; and
    ii. measuring the total light signal from each of the particle area and the surrounding area of at least two different particle areas.

According to one embodiment of the present invention, an apparatus for homogenous assaying an analyte in a sample, comprising:
  i. a device of any prior embodiment,
  ii. an imager or imagers that images at least a part of the sample contact area.

According to one embodiment of the present invention, a smartphone system for homogeneous assay, comprising:
  (a) a device of any prior embodiment;
  (b) a mobile communication device that comprises:
    i. one or a plurality of cameras for detecting and/or imaging the sample;
    ii. electronics, signal processors, hardware and software for receiving and/or processing the detected signal and/or the image(s) of the sample and for remote communication; and
  (c) an adaptor that is configured to accommodate the device that is in the closed configuration and be engageable to the mobile communication device;
  wherein when engaged with the mobile communication device, the adaptor is configured to facilitate the detection and/or imaging of the analyte in the sample.

The device of any prior embodiment, wherein the distribution of the plurality of particles on the plate is random.

The device of any prior embodiment, wherein the plurality of particles are fixed on the plate and has periodic distribution.

The device of any prior embodiment, wherein the spacer has a flat top.

The device of any prior embodiment, wherein the plurality of particles is temporarily fixed on the first plate, and in an open configuration the sample is deposited first on the first plate before the two plates being bought into the closed configuration.

The device of any prior embodiments, wherein the thickness of the spacer is configured, so that in a closed configuration, for a certain concentration of the analytes in the sample, at least one area of the uniform thickness sample that contains one of the particle becomes optically distinguishable, when viewed outside of the sample layer, from its neighboring area that does not contain a particle.

The device of any prior embodiment, the device comprising two plates and spacers, wherein the pressing is by human hand.

The device of any prior embodiment, the device comprising two plates and spacers, wherein at least a portion of the inner surface of one plate or both plate is hydrophilic.

The device of any prior embodiment, the device comprising two plates and spacers, wherein the inter spacer distance is periodic.

The device of any prior embodiment, the device comprising two plates and spacers, wherein the sample is a deposition directly from a subject to the plate without using any transferring devices.

The device of any prior embodiment, the device comprising two plates and spacers, wherein after the sample deformation at a closed configuration, the sample maintains the same final sample thickness, when some or all of the compressing forces are removed.

The device of any prior embodiment, the device comprising two plates and spacers, wherein the spacers have pillar shape and nearly uniform cross-section.

The device of any prior embodiment, the device comprising two plates and spacers, wherein the inter spacer distance (SD) is equal or less than about 120 um (micrometer).

The device of any prior embodiment, the device comprising two plates and spacers, wherein the inter spacer distance (SD) is equal or less than about 100 um (micrometer). The device of any prior embodiment, the device comprising two plates and spacers, wherein the fourth power of the inter-spacer-distance (ISD) divided by the thickness (h) and the Young's modulus (E) of the flexible plate (ISD^4/(hE)) is 5×10^6 um^3/GPa or less. The device of any prior embodiment, the device comprising two plates and spacers, wherein the fourth power of the inter-spacer-distance (ISD) divided by the thickness (h) and the Young's modulus (E) of the flexible plate (ISD^4/(hE)) is 5×10^5 um3/GPa or less.

The device of any prior embodiment, the device comprising two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device of any prior embodiment, the device comprising two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

The device of any prior embodiment, wherein the ratio of the inter-spacing distance of the spacers to the average width of the spacer is 2 or larger, and the filling factor of the spacers multiplied by the Young's modulus of the spacers is 2 MPa or larger.

The method of any prior embodiment, wherein the particle area for the total light signal measurement has substantially the same area as the particle diameter.

The method of any prior embodiment, wherein the particle area for the total light signal measurement is smaller than the area defined by the particle diameter.

The method of any prior embodiment, wherein the analyzing the analyte in the uniform sample layer comprising averaging of the total light signal from each area.

The method of any prior embodiment, wherein the analyzing the analyte in the uniform sample layer comprising (i) taking a ration of the total light signal of each particle area to that of its surrounding area, and (ii) averaging the ratio of all particle area and surround area pairs.

The method of any prior embodiment, wherein the time from the end of the sample deposition to the end of reach a closed configuration is less than 15 seconds.

The method of any prior embodiment, wherein the time from the end of the sample deposition to the end of reach a closed configuration is less than 5 seconds.

The method of any prior embodiment, wherein the surrounding area is 2 D within the edge of the particle.

The method of any prior embodiment, wherein the surrounding area is 5 D within the edge of the particle.

The method of any prior embodiment, wherein the surrounding area is 10 D within the edge of the particle.

The method of any prior embodiment, wherein the surrounding area is 20 D within the edge of the particle.

The method of any prior embodiment, wherein the surrounding area is 50 D within the edge of the particle.

1.1 One Step Assay.

In order to achieve one-step assay that detects an analyte in a sample, a key approach of the present invention is to make the captured analyte "visible" in the sample (i.e. that is distinguishable from the rest of the sample) without any washing. The term "captured analyte" refers to the analyte that is being selectively (i.e. specifically) captured by a capture agent.

A captured analyte can give a signal by (a) being attached to a label that can give a signal, (b) giving a signal on its own, and (c) both (a) and (b). Here we focus on the situation (a), wherein the signal from a captured analyte comes from a light label ("label"), wherein the label is capable of selectively attaching to the analyte using a detection agent, and wherein the detection agent can selectively bind to the analyte. However, the invention equally applies to the situations of (b) and (c).

In a one-step assay for situation (a), the objective is to identify/detect the bound labels that are bound to the analyte (the label is termed "bound label", and the analyte is termed "labeled analyte") from the labels that are not bound to the analyte ("unbound label").

In a one-step assay for situation (b), the objective is to identify/detect the bound analyte (i.e. captured by a capture agent) from the analytes that are not captured by a capture agent ("unbound analyte"). When the principle of situation (a) is used to situation (b), the bond label and unbound label in situation (a) becomes the bound analyte and the unbound analyte in the situation (b).

According to the present invention, the one step assay uses two plates to sandwich a thin layer of a sample that has an analyte between the plates, uses a detector above the sample layer to detect a signal from a label (FIG. 4), and identify bound label from unbound label through one of the following approaches:

(i) concentrating the bound label into a or a plurality of locations in the sample (termed "concentrated location"), while reduce the concentration of the bound label in the other locations of the sample;

(ii) reducing the local background signal at analyte concentration area (C-LBS), wherein the C-LBS is defined as the background signal generate by the sample volume that is in front of the concentration surface (hence the sample volume is equal to the local sample thickness (from the analyte concentration area to the front plate's inner surface) multiplies by the area of the concentration surface at that location. For example, the C-LBS at a location of a concentration protrusion (with only the protrusion top surface has an analyte concentration area) is the background signal in the sample volume, wherein the volume is equal to the distance between the top of the protrusion to the top plate surface multiplying the area of protrusion's top at the interested location. In this example, clearly the higher the protrusion, the smaller the local background volume, and hence the smaller the C-LBS.

(iii) selectively (i.e. only the bound label, not unbound label) attaching the bound label onto an amplification surface, wherein the amplification surface amplifies the signal of a label only when the label is attached to the surface or within a short distance from the surface (e.g. less than 1 um);

(iv) selectively attaching the bound quencher onto an surface with label, wherein the labeling surface reduces the signal only when the quencher is attached to the surface or within a short distance from the surface (e.g. less than 1 um);

(v) a combination of thereof.

A. Concentrating the Labeled Analyte/Bound Label

Example of embodiments of the present invention for concentrating the labeled analyte/bound label are given below.

(1) Concentration surface. A device for concentrating bound label, comprises: two plates (or an enclosed channel) with a sample (that has an analyte) sandwiched between the two plates, wherein one or both of the plates has a analyte concentration area on its inner surface of the plate, wherein the analyte concentration area has an capture agent that selectively binds the bound label directly or indirectly (i.e. the analyte concentration area has a higher affinity to bind the bound label than the rest area of the plate). An indirect binding means that the capture agent captures an analyte, while the analyte is bound to a label (this is most common case).

The term "analyte concentration area" refers to an area of a surface where the area has a higher affinity to bind the labeled analyte/bound label (or to bind an analyte what later binds a label) than the rest area of the surface.

In some embodiments, a concentration surface can be formed by immobilizing capture agent on the concentration surface, wherein the capture agent specifically bind the analyte.

In some embodiments, a concentration surface can be formed by reducing the binding of the analytes in the surfaces other than the concentration surface.

(2) Concentration protrusion (e.g. pillar). A device for concentrating bound label, comprises: two plates (or an enclosed channel) with a sample (that has an analyte) sandwiched between the two plates, wherein one or both of the plates has a or a plurality of protrusions, wherein the protrusion has a analyte concentration area on at least one of the protrusion's surfaces, wherein the analyte concentration area selectively bind the labeled analyte/bound label.

(3) Concentration bead. A device for concentrating labeled analyte/bound label, comprises: two plates (or an enclosed channel) with a sample (that has an analyte) sandwiched between the two plates, wherein one bead or a plurality of beads is placed in the sample, wherein the bead has a analyte concentration area on the bead's surface, wherein the analyte concentration area selectively bind the bound label.

(4) Combination. Any combination of (1)-(3).

B. Making the Captured Analyte (with Label) Visible

When a detector is used to image an optical signal emitting through the front plate of the sample-plate sandwich, a 2D image will be obtained.

In this 2D image, the requirement for making the analyte concentration area (after catching the labeled analyte) visible (i.e. distinguishable) over the background signal from the latera areas that are not analyte concentration area (i.e. non-analyte concentration area local background signal, "NC-LBS") is that the signal from the analyte concentration area plus the C-LBL must be larger than NC-LBS by at least one standard variation of the NC-LBS (This condition is termed "visible condition"). The visible condition can be achieved by (i) increase the signal in the analyte concentration area, (ii) reducing C-LBS, (iii) reducing NC-LBS, or (iv) a combination of thereof.

A visible condition can be achieved by adjusting (i) total label concentration in a sample (since some will form bound label with analyte, and the rest will be unbound become a part of background signal), (ii) the total analyte concentration (i.e. limit of detection), (iii) the area or density of the analyte concentration area, (iv) the distance between the analyte concentration area to the front plate, (v) amplification factor of an amplification surface, (vi) the shape of the concentration/amplification area, (vii) the capture reagent concentration on the concentration/amplification area, (viii) the incubation time, or (ix) a combination thereof.

C. Making Assay Rapid

According to the present invention, an assay can have a short assaying time (i.e. being speeded up) by using the following three approaches: (a) using two plates to sandwich a sample into a thin layer between the plates and by limiting the spacing between the two plates (hence the thickness of at least a port of the sample) into small size (e.g. the spacing is equal to or less than the diffusion parameter (as defined in Definition), since a smaller diffusion parameter will have less diffusion time); (b) making the average lateral distance between two neighboring analyte concentration areas (i.e. inter analyte concentration-area distance (IACD) small (e.g. IACD is equal to or less than 2 times of the diffusion parameter); and (c) (a) and (b).

In certain embodiments, the spacing between the two plate (or the spacer height) is 50 nm, 100 nm, 200 nm, 500 nm, 700 nm, 900 nm, 1 um, 2 um, 3 um, 4 um, 5 um, 6 um, 7 um, 8 um, 9 um, 10 um, 20 um, 30 um, 40 um, 50 um, 60 um, 70 um, 80 um, 90 um, 100 um, 120 um, 150 um, 180 um, 200 um, or in a range between any two of these values.

In some preferred embodiments, the spacing between the two plates (or the spacer height) is 500 nm, 700 nm, 900 nm, 1 um, 2 um, 3 um, 4 um, 5 um, 6 um, 7 um, 8 um, 9 um, 10 um, 20 um, 30 um, 40 um, 50 um, or in a range between any two of these values.

In certain preferred embodiments, the spacing between the two plates (or the spacer height) is 500 nm, 700 nm, 900 nm, 1 um, 2 um, 3 um, 4 um, 5 um, 6 um, 7 um, 8 um, 9 um, 10 um, 20 um, or in a range between any two of these values.

In certain embodiments, the spacing between the two plate (or the spacer height) is 0.01 times of the DP (diffusion parameter), 0.01 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 2.5 times of the DP, 3 times of the DP, 4 times of the DP, 5 times of the DP, or in a range between any two of these values.

In some preferred embodiments, the spacing between the two plate (or the spacer height) is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 2.5 times of the DP, or in a range between any two of these values.

In certain preferred embodiments, the spacing between the two plate (or the spacer height) is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, or in a range between any two of these values.

In certain embodiments, the average IACD is 50 nm, 100 nm, 200 nm, 500 nm, 700 nm, 900 nm, 1 um, 2 um, 3 um, 4 um, 5 um, 6 um, 7 um, 8 um, 9 um, 10 um, 20 um, 30 um, 40 um, 50 um, 60 um, 70 um, 80 um, 90 um, 100 um, 120 um, 150 um, 180 um, 200 um, or in a range between any two of these values.

In some preferred embodiments, the average IACD is 500 nm, 700 nm, 900 nm, 1 um, 2 um, 3 um, 4 um, 5 um, 6 um, 7 um, 8 um, 9 um, 10 um, 20 um, 30 um, 40 um, 50 um, or in a range between any two of these values.

In certain preferred embodiments, the average IACD is 500 nm, 700 nm, 900 nm, 1 um, 2 um, 3 um, 4 um, 5 um, 6 um, 7 um, 8 um, 9 um, 10 um, 20 um, or in a range between any two of these values.

In certain embodiments, the average IACD is 0.01 times of the DP (diffusion parameter), 0.01 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 3 times of the DP, 4 times of the DP, 5 times of the DP, or in a range between any two of these values.

In some preferred embodiments, the average IACD is 0.01 times of the DP (diffusion parameter), 0.01 times of the DP, 0.1 times of the DP, 0.3 times of the DP, 0.5 times of the DP, 0.7 times of the DP, 1 times of the DP, 1.2 times of the DP, 1.5 times of the DP, 1.8 times of the DP, 2 times of the DP, 2.5 times of the DP, or in a range between any two of these values.

In certain preferred embodiments, the average IACD is 0.01 times of the DP (diffusion parameter), 0.01 times of the DP, 0.1 times of the DP, 0.3 times of the DP, 0.7 times of the DP, 1 times of the DP, 1.2 times of the DP, 1.5 times of the DP, or in a range between any two of these values.

In certain preferred embodiments, the average IACD is 500 nm, 700 nm, 900 nm, 1 um, 2 um, 3 um, 4 um, 5 um, 6 um, 7 um, 8 um, 9 um, 10 um, 20 um, or in a range between any two of these values.

In certain embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, 70 sec, 80 sec, 100 sec, 120 sec, 140 sec, 160 sec, 180 sec, 200 sec, 220 sec, 240 sec, or in a range between any two of these values.

In some preferred embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, 70 sec, 80 sec, 100 sec, 120 sec, 140 sec, 160 sec, 180 sec, or in a range between any two of these values.

In certain preferred embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, 70 sec, 80 sec, 100 sec, 120 sec, or in a range between any two of these values.

In certain preferred embodiments, the intended assay time for the DP is 0.01 sec, 0.1 sec, 0.5 sec, 1 sec, 2 sec, 5 sec, 10 sec, 15 sec, 20 sec, 25 sec, 30 sec, 40 sec, 50 sec, 60 sec, or in a range between any two of these values.

In certain embodiments, each of the embodiments has an average IACD and a spacing between the two plate (or a spacer height) that are chosen from the size value or range given in previous paragraphs.

The spacing between the plates can be formed either without using a spacer or with spacers. In some embodiments, the two plates with spacers are parts of a QMAX device (or QMAX card, CROF device, CROF card, which all refer to the same device).

D. Control Plate Spacing and Sample Thickness Using Spacers

According to the present invention, the spacing between the two plates and hence the sample thickness are controlled by using the spacers.

The present invention uses a combination of A to D to achieve a one-step assay.

Spacer Height.

In some embodiments, all spacers have the same pre-determined height. In some embodiments, spacers have different pre-determined heights. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 μm or less, 2 μm or less, 3 μm or less, 5 μm or less, 10 μm or less, 20 μm or less, 30 μm or less, 50 μm or less, 100 μm or less, 150 μm or less, 200 μm or less, 300 μm or less, 500 μm or less, 800 μm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1000 nm in a separate preferred embodiment, 1 μm (i.e. 1000 nm) to 2 μm in another preferred embodiment, 2 μm to 3 μm in a separate preferred embodiment, 3 μm to 5 μm in another preferred embodiment, 5 μm to 10 μm in a separate preferred embodiment, and 10 μm to 50 μm in another preferred embodiment, 50 μm to 100 μm in a separate preferred embodiment.

In some embodiments, the spacer height is controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, or in a range between any of the values.

In some embodiments, the spacer height, the spacing between the plates, and/or sample thickness is: (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

For example, the red blood cell has a disk shape with a minim dimension of 2 μm (disk thickness) and a maximum dimension of 11 μm (a disk diameter). In an embodiment of the present invention, the spacers are selected to make the inner surface spacing of the plates in a relevant area to be 2 μm (equal to the minimum dimension) in one embodiment, 2.2 μm in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 μm and any number between the two values, an undiluted whole blood sample is confined in the spacing; on average, each red blood cell (RBC) does not overlap with others, allowing an accurate counting of the red blood cells visually. (Too many overlaps between the RBC's can cause serious errors in counting).

In some embodiments, the spacer height, the spacing between the plates, and/or sample thickness is: (i) equal to or smaller than the minimum dimension of an analyte, or (ii) equal to or slightly smaller than the maximum dimension of an analyte. The "slightly smaller" means that it is about 1% to 5% smaller and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

In the present invention, in some embodiments, the plates and the spacers are used to regulate not only the thickness of a sample, but also the orientation and/or surface density of the analytes/entity in the sample when the plates are at the closed configuration. When the plates are at a closed configuration, a thinner thickness of the sample results in less analytes/entity per surface area (i.e. less surface concentration).

Spacer lateral dimension. For an open-spacer, the lateral dimensions can be characterized by its lateral dimension (sometimes called width) in the x and y—two orthogonal directions. The lateral dimension of a spacer in each direction is the same or different. In some embodiments, the lateral dimension for each direction (x or y) is 1 nm or less, 3 nm or less, 5 nm or less, 7 nm or less, 10 nm or less, 20 nm or less, 30 nm or less, 40 nm or less, 50 nm or less, 100 nm or less, 200 nm or less, 500 nm or less, 800 nm or less, 1000 nm or less, 1 μm or less, 2 μm or less, 3 μm or less, 5 μm or less, 10 μm or less, 20 μm or less, 30 μm or less, 50 μm or less, 100 μm or less, 150 μm or less, 200 μm or less, 300 μm or less, or 500 μm or less, or in a range between any two of the values.

In some embodiments, the ratio of the lateral dimensions of x to y direction is 1, 1.5, 2, 5, 10, 100, 500, 1000, 10,000, or in a range between any two of the value. In some embodiments, a different ratio is used to regulate the sample flow direction; the larger the ratio, the flow is along one direction (larger size direction).

In some embodiments, different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height of the spacers are substantially the same. In some embodiments, all spacers have the same shape and dimensions. In some embodiments, the spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or in a range between any two of the values.

Inter-spacer distance. The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers is arranged as lattices of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

In some embodiments, the distance between neighboring spacers (i.e. the inter-spacer distance) is 1 μm or less, 5 μm or less, 7 μm or less, 10 μm or less, 20 μm or less, 30 μm or less, 40 μm or less, 50 μm or less, 60 μm or less, 70 μm or less, 80 μm or less, 90 μm or less, 100 μm or less, 200 μm or less, 300 μm or less, 400 μm or less, or in a range between any two of the values.

In certain embodiments, the inter-spacer distance is at 400 μm or less, 500 μm or less, 1 mm or less, 2 mm or less, 3 mm or less, 5 mm or less, 7 mm or less, 10 mm or less, or in any range between the values. In certain embodiments, the inter-spacer distance is a 10 mm or less, 20 mm or less, 30 mm or less, 50 mm or less, 70 mm or less, 100 mm or less, or in any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or in any range between the values; or in certain embodiments, at most 80%, 100%, 200%, 400%, or in a range between any two of the values.

Clearly, for maintaining a given sample thickness variation between two neighboring spacers, when a more flexible plate is used, a closer inter-spacer distance is needed.

In a preferred embodiment, the spacer is a periodic square array, wherein the spacer is a pillar that has a height of 2 to 4 μm, an average lateral dimension of from 1 to 20 μm, and inter-spacer spacing of 1 μm to 100 μm.

In a preferred embodiment, the spacer is a periodic square array, wherein the spacer is a pillar that has a height of 2 to 4 μm, an average lateral dimension of from 1 to 20 μm, and inter-spacer spacing of 100 μm to 250 μm.

In a preferred embodiment, the spacer is a periodic square array, wherein the spacer is a pillar that has a height of 4 to 50 μm, an average lateral dimension of from 1 to 20 μm, and inter-spacer spacing of 1 μm to 100 μm.

In a preferred embodiment, the spacer is a periodic square array, wherein the spacer is a pillar that has a height of 4 to 50 μm, an average lateral dimension of from 1 to 20 μm, and inter-spacer spacing of 100 μm to 250 μm.

The period of spacer array is between 1 nm to 100 nm in one preferred embodiment, 100 nm to 500 nm in another preferred embodiment, 500 nm to 1000 nm in a separate preferred embodiment, 1 μm (i.e. 1000 nm) to 2 μm in another preferred embodiment, 2 μm to 3 μm in a separate preferred embodiment, 3 μm to 5 μm in another preferred embodiment, 5 μm to 10 μm in a separate preferred embodiment, and 10 μm to 50 μm in another preferred embodiment, 50 μm to 100 μm in a separate preferred embodiment, 100 μm to 175 μm in a separate preferred embodiment, and 175 μm to 300 μm in a separate preferred embodiment.

Spacer density. The spacers are arranged on the respective plates at a surface density of greater than one per $\mu m^2$, greater than one per 10 $\mu m^2$, greater than one per 100 $\mu m^2$, greater than one per 500 $\mu m^2$, greater than one per 1000 $\mu m^2$, greater than one per 5000 $\mu m^2$, greater than one per 0.01 $mm^2$, greater than one per 0.1 $mm^2$, greater than one per 1 $mm^2$, greater than one per 5 mm2, greater than one per 10 $mm^2$, greater than one per 100 $mm^2$, greater than one per 1000 mm2, greater than one per 10000 mm2, or in a range between any two of the values. In some embodiments, the spacers have a density of at least $1/mm^2$, at least $10/mm^2$, at least $50/mm^2$, at least $100/mm^2$, at least $1,000/mm^2$, or at least $10,000/mm^2$.

Spacer area filling factor is defined as the ratio of spacer area to the total area or the ratio of spacer period to the width. In some embodiments, the filling factor is at least 1%, 2%, 3%, 4%, 5%, 6%, 7%, 8%, 9%, 10%, 20%, or in the range between any of the two values. In certain embodiments, the filling factor is at least 2.3%.

The device that comprises two plates and spacers, wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the fourth power of the inter-spacer-distance (ISD)

divided by the thickness (h) and the Young's modulus (E) of the flexible plate (ISD^4/(hE)) is 5×10^5 um3/GPa or less.

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the ratio of the inter-spacing distance of the spacers to the average width of the spacer is 2 or larger, and the filling factor of the spacers multiplied by the Young's modulus of the spacers is 2 MPa or larger.

2. Exemplary Embodiments for Rapid Homogeneous Assays (RHA)

2.1 RHA with Concentration Surface.

A device for concentrating bound label, comprises: two plates (or an enclosed channel) with a sample (that has an analyte) sandwiched between the two plates, wherein one or both of the plates has a analyte concentration area on its inner surface of the plate, wherein the analyte concentration area has a capture agent that selectively binds the bound label directly or indirectly (i.e. the analyte concentration area has a higher affinity to bind the bound label than the rest area of the plate).

Figure 4:
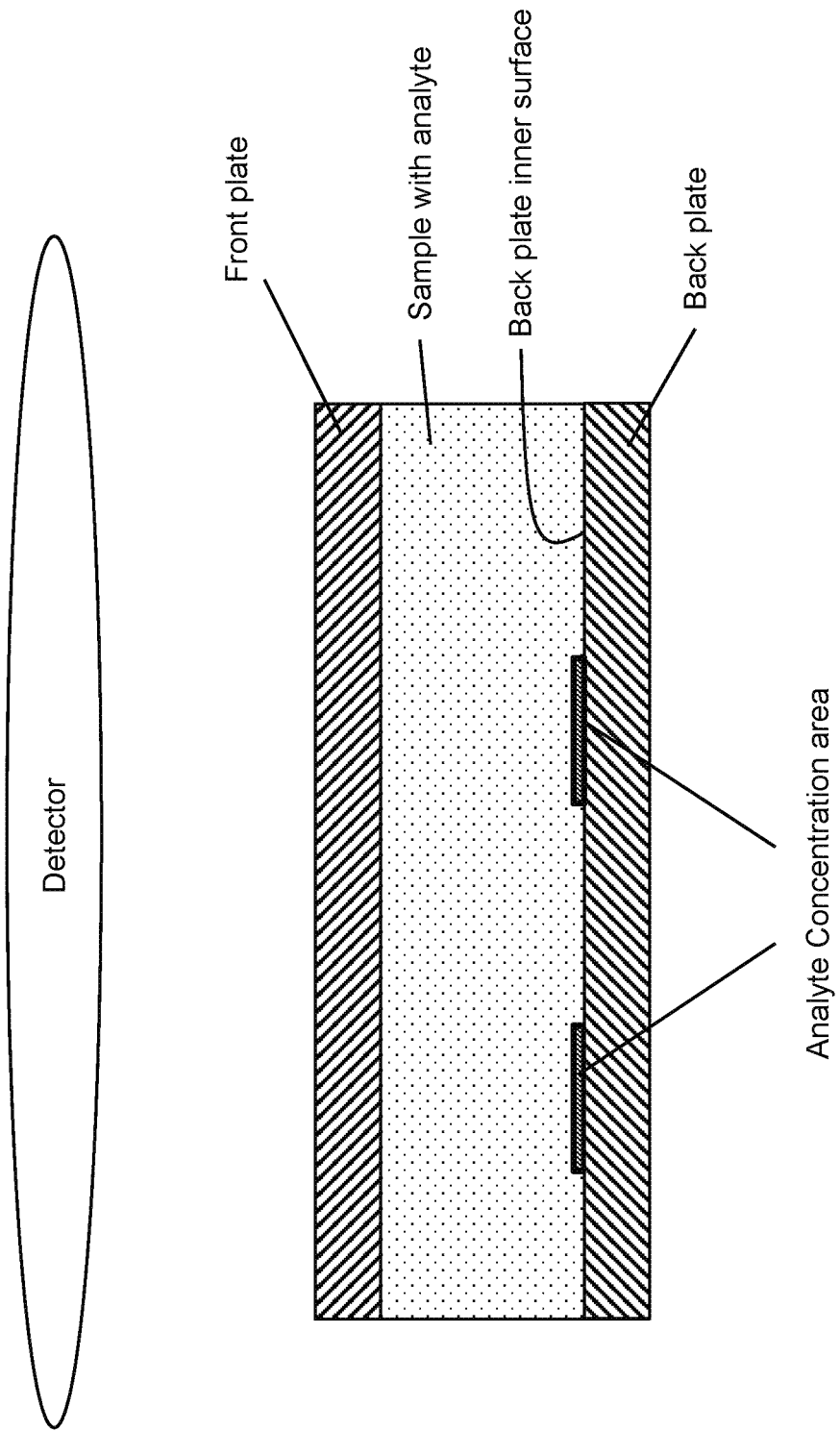
FIG. 4 illustrates a cross-sectional view of an exemplary system for homogeneous assay at its closed configuration, which includes two plates with two analyte concentration areas.

FIG. 4 schematically illustrates a cross-sectional view of an exemplary system for homogeneous assay at its closed configuration, which includes two plates with two analyte concentration areas on one of the plate. As shown in the figure, a sample that contains the analyte is compressed by the two plates (front plate and back plate) into a thin layer. The back plate comprises analyte concentration areas on its inner surface. The analyte concentration areas have surfaces to capture analyte and are configured to have higher affinity to the analyte than other area of the inner surface, thereby concentrating the analyte to the surfaces thereof.

In some embodiments, the concentration of analyte to the analyte concentration areas consequentially significantly reduce the analyte in the surrounding of the analyte concentration areas, therefore each analyte concentration area not only concentrates analyte signal on its surface (higher than the surrounding area), but also reduces the local background signal in the locations that are surrounding the analyte concentration area.

Further, also shown in the figure is the detector on the top side of the two plates. The detector is configured to image the distribution of the signal of the analyte on the plate surface, wherein the signal is indicative of the presence and/or quantity of the analyte.

In some embodiments, the (i) total label concentration in a sample (since some will form bound label with analyte, and the rest will be unbound become a part of background signal), (ii) the total analyte concentration (i.e. limit of detection), or a combination of thereof is configured to achieve the visible condition.

In some embodiments, the (i) total label concentration in a sample (since some will form bound label with analyte, and the rest will be unbound become a part of background signal), (ii) the total analyte concentration (i.e. limit of detection), (iii) the area or density of the analyte concentration area, (iv) the distance between the analyte concentration area to the front plate, or (v) a combination of thereof is configured to achieve the visible condition.

In some embodiments, the amplification factor of an amplification surface is configured to achieve the visible condition.

In some embodiments, the (i) total label concentration in a sample (since some will form bound label with analyte, and the rest will be unbound become a part of background signal), (ii) the total analyte concentration (i.e. limit of detection), (iii) the area or density of the analyte concentration area, (iv) the distance between the analyte concentration area to the front plate, (v) amplification factor of an amplification surface, (vi) the shape of the concentration/amplification area, (vii) the capture reagent concentration on the concentration/amplification area, (viii) the incubation time, or (ix) a combination thereof is configured to achieve the visible condition.

In some embodiments, the analyte concentration area has a pillar shape. The shape of the top surface of the pillar can be round, a point (of a pyramid), polygon, elliptical, elongated bar, polygon, other similar shapes or combinations thereof. The spacing between the pillars in the array can be periodic or aperiodic. In some embodiments, the period (the spacing between adjacent pillars in periodic arrays) is 2 nm or less, 5 nm or less, 10 nm or less, 50 nm or less, 100 nm or less, 500 nm or less, 1000 nm or less, 2000 nm or less, 4000 nm or less, or in a range between any two of these values. In some embodiments, the average spacing between adjacent pillars in aperiodic arrays is 2 nm or less, 5 nm or less, 10 nm or less, 50 nm or less, 100 nm or less, 500 nm or less, 1000 nm or less, 2000 nm or less, 4000 nm or less, or in a range between any two of these values.

In some embodiments, the area density of the analyte concentration areas on the inner surface is 1 per $mm^2$ or less, 2 per $mm^2$ or less, 5 per $mm^2$ or less, 10 per $mm^2$ or less, 50 per mm2 or less, 100 per $mm^2$ or less, 200 per $mm^2$ or less, 500 per $mm^2$ or less, 1000 per mm2 or less, $1\times10^3$ per $mm^2$ or less, $2\times10^3$ per $mm^2$ or less, $3\times10^3$ per $mm^2$ or less, $5\times10^3$ per $mm^2$ or less, $10\times10^3$ per mm2 or less, $2\times10^3$ per $mm^2$ or less, $3\times10^3$ per mm2 or less, $5\times10^3$ per mm2 or less, $10\times10^3$ per $mm^2$ or less, $1\times10^5$ per $mm^2$ or less, $5\times10^5$ per $mm^2$ or less, $1\times10^6$ per $mm^2$ or less, or in a range between any two of these values.

In some embodiments, the analyte concentration area has an average lateral dimension of 10 nm or less, 50 nm or less, 100 nm or less, 200 nm or less, 500 nm or less, or in a range between any two of these values.

In some embodiments, the average lateral dimension of the analyte concentration area is 0.5 um or less, 1 um or less, 2 um or less, 5 um or less, 10 um or less, 50 um or less, 100 um or less, 300 um or less, 500 um or less or in a range between any two of these values.

In some embodiments, the thickness of the analyte concentration area is 10 nm or less, 50 nm or less, 100 nm or less, 200 nm or less, 500 nm or less, or in a range between any two of these values.

In some embodiments, the thickness of analyte concentration area is 0.5 um or less, 1 um or less, 2 um or less, 5 um or less, 10 um or less, 50 um or less, 100 um or less, 300 um or less, 500 um or less, or in a range between any two of these values.

In some embodiments, the ratio of the spacing between two plates at the closed configuration versus the height (thickness) of the analyte concentration area is 1 or less, 1.1 or less, 1.2 or less, 1.5 or less, 2 or less, 3 or less, 5 or less, 10 or less, 15 or less, 20 or less, 30 or less, 40 or less, 50 or less, 60 or less, 80 or less, 100 or less, 200 or less, 300 or less, 400 or less, 500 or less, 600 or less, 800 or less, 1000 or less, or in a range between any two of these values.

In some embodiments, the height (thickness) of the analyte concentration area is 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, 300 um or more, 500 um or more, or in a range between any two of these values.

2.2 RHA with Concentration Protrusion (e.g. Pillar)

A device for concentrating bound label, comprises: two plates (or an enclosed channel) with a sample (that has an analyte) sandwiched between the two plates, wherein one or both of the plates has a protrusion, wherein the protrusion has a analyte concentration area on at least one of the protrusion's surfaces, wherein the analyte concentration area has a capture agent that selectively binds to the labeled analyte/bound label and/or the analyte to be labeled.

Figure 5:
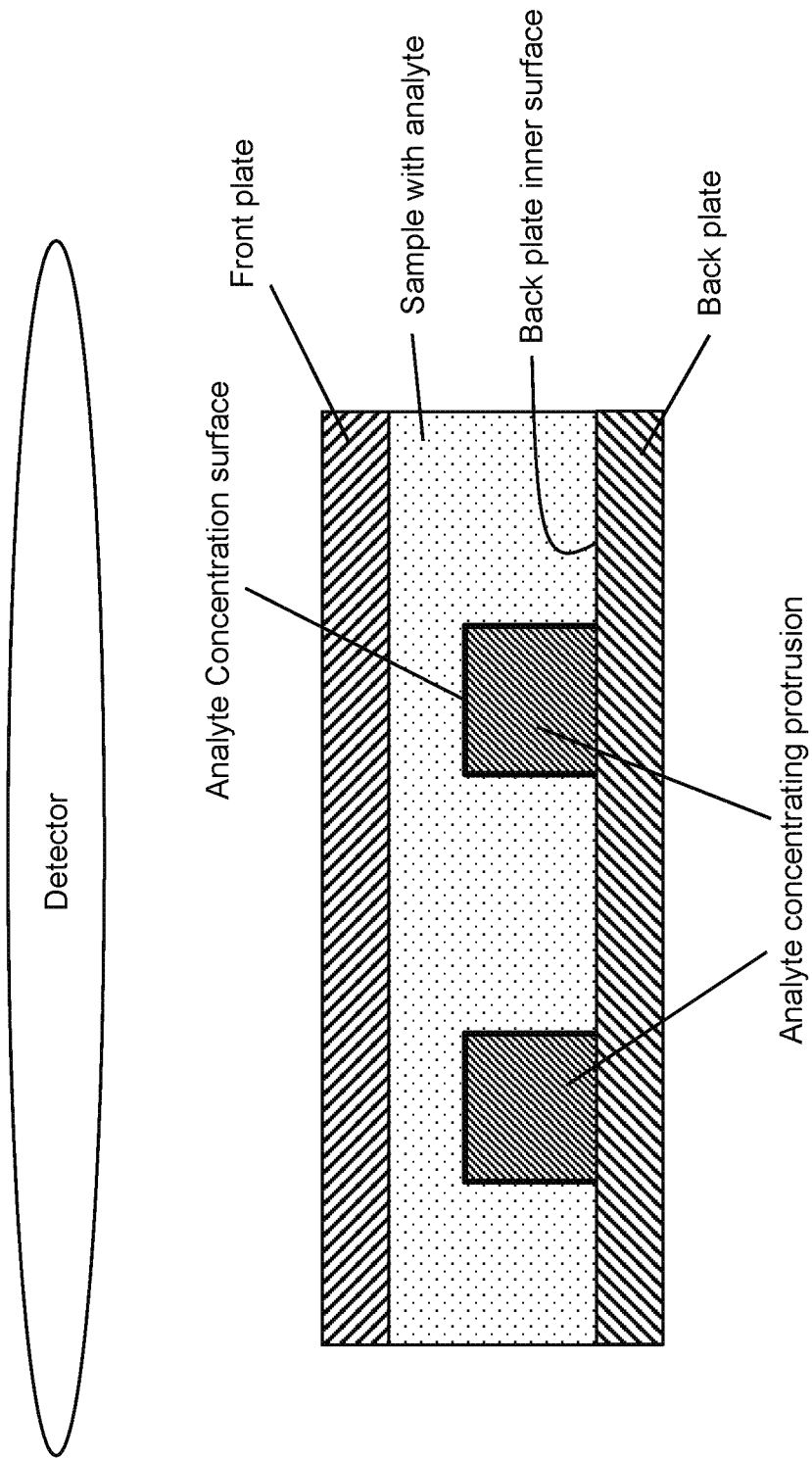
FIG. 5 illustrates a cross-sectional view of another exemplary system for homogeneous assay at its closed configuration, which includes two plates with two analyte concentrating protrusions.

FIG. 5 schematically illustrates a cross-sectional view of another exemplary system for homogeneous assay at its closed configuration, which includes two plates with two analyte concentrating protrusions. Similar as FIG. 4, the sample is compressed by the two plates (front plate and back plate) into a thin layer. The back plate comprises the two analyte concentrating protrusions that extending from its inner surface. Each of the concentrating protrusions has a concentration surface to capture the analyte. In addition to the analyte signal enhancing effect and background reduction effect, each protrusion further reduces the local background signal on top of it, by reducing the sample thickness on top of it. Similar to FIG. 4, the system also includes the detector that detects the signal of the analyte.

Figure 10:
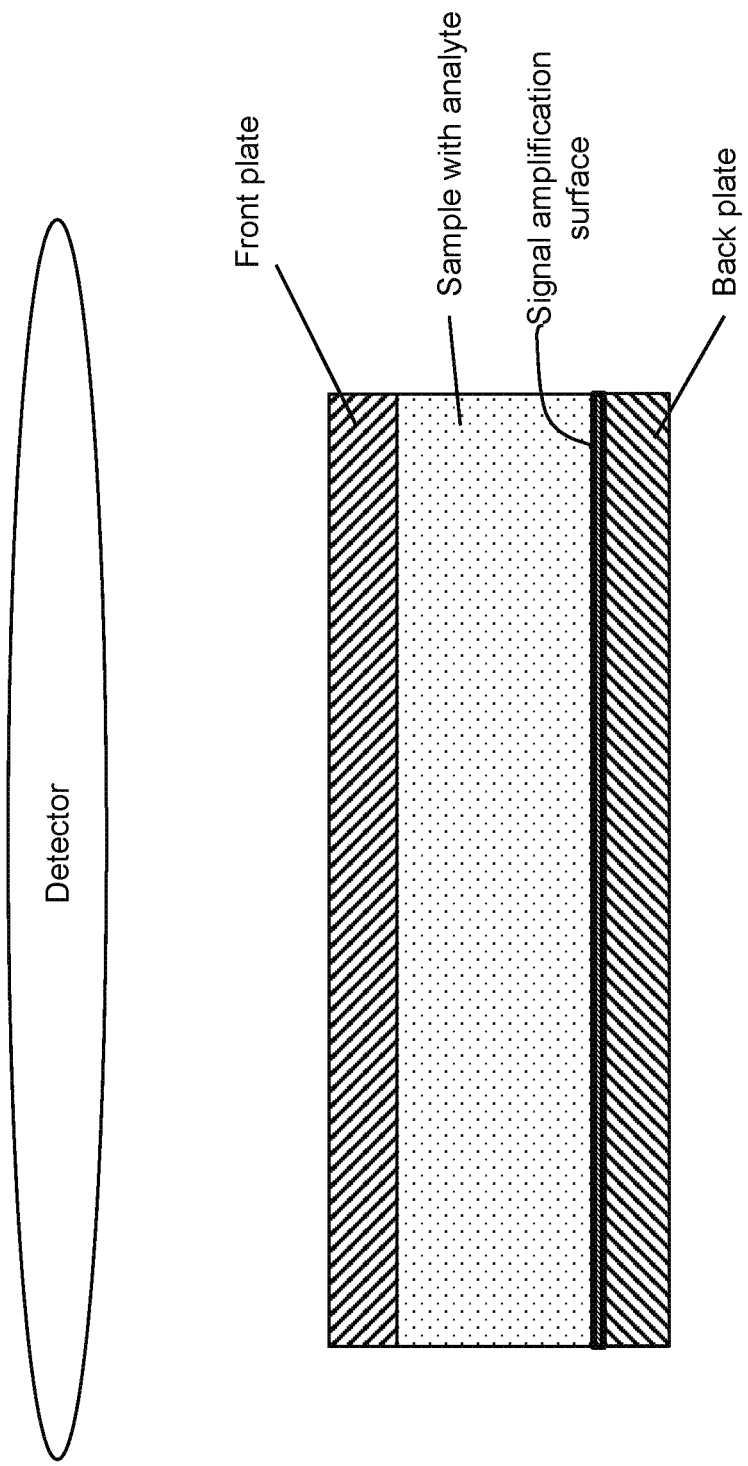
FIG. 10 illustrates a cross-sectional view of another exemplary system for homogeneous assay at its closed configuration, which includes a signal amplification surface on one of the two plates.

FIG. 10 schematically illustrates a cross-sectional view of another exemplary system for homogeneous assay at its closed configuration, which includes a signal amplification surface on one of the two plates. As shown in the figure, the back plate comprises a signal amplification surface on its inner surface. When the labeled analyte is bound to the signal amplification surface, the signal amplification surface is configured to amplify the signal of the bound analyte to a level that is distinguishable from the background.

The spacing between the pillars (analytes concentration area) in the array can be periodic or aperiodic. In many embodiments, a periodic array are preferred. In some embodiments, the period (the spacing between adjacent pillars in periodic arrays) is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, 25 um or less, 30 um or less, 40 um or less, 50 um or less, 60 um or less, 70 um or less, or in a range between any two of these values.

In some embodiments, the average spacing between adjacent pillars in aperiodic arrays is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, 25 um or less, 30 um or less, 40 um or less, 50 um or less, 60 um or less, 70 um or less, or in a range between any two of these values.

In certain preferred embodiments, the average lateral dimension of the protrusion is 0.5 um, 1 um, 3 um, 5 um, 10 um, 20 um, 50 um, 100 um, 150 um, 200 um, or in a range between any two of these values.

In certain preferred embodiments, the average height of the protrusion is 0.5 um, 1 um, 3 um, 5 um, 10 um, 20 um, 50 um, 100 um, 150 um, 200 um, or in a range between any two of these values.

In certain preferred embodiments, the average spacing between adjacent pillars is 1 um, 2 um, 5 um, 10 um, 20 um, 50 um, 100 um, 150 um, 200 um, 500 um, or in a range between any two of these values.

In certain preferred embodiments, the average lateral dimension of the protrusion is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, 2 times of the DP, 3 times of the DP or in a range between any two of these values.

In certain preferred embodiments, the average height of the protrusion is 0.01 times of the DP (diffusion parameter), 0.05 times of the DP, 0.1 times of the DP, 0.3 times of the DP, 0.5 times of the DP, 0.7 times of the DP, 1 times of the DP, 1.2 times of the DP, 1.5 times of the DP, 2 times of the DP, 3 times of the DP or in a range between any two of these values.

In certain preferred embodiments, the average spacing between adjacent pillars is 0.01 times of the DP, 0.1 times of the DP, 0.3 times of the DP, 0.5 times of the DP, 0.7 times of the DP, 1 times of the DP, 1.2 times of the DP, 1.5 times of the DP, 2 times of the DP, 5 times of the DP or in a range between any two of these values.

Spacing between the top surface of the protrusion and the plate above (i.e. protrusion-surface to plate surface distance (PsPsD)). In certain embodiments, the PsPsD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, or in a range between any two of these values.

In certain preferred embodiments, the PsPsD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, or in a range between any two of these values.

In some preferred embodiments, the PsPsD is 2 nm or less, 5 nm or less, 10 nm or less, 50 nm or less, 100 nm or less, 500 nm or less, 1 um or less, 2 um or less, 3 um or less, 4 um or less, 5 um or less, or in a range between any two of these values.

Difference between protrusion height and spacer height (i.e. Protrusion and Spacer Height Difference (PSHD)). In certain embodiments, the PSHD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, 15 um or less, 20 um or less, or in a range between any two of these values.

In certain preferred embodiments, the PSHD is 2 nm or less, 5 nm or less, 10 nm or less, 50 nm or less, 100 nm or less, 500 nm or less, 1 um or less, 2 um or less, 3 um or less, 4 um or less, 5 um or less, 10 um or less, or in a range between any two of these values.

In some preferred embodiments, the PSHD is 2 nm or less, 5 nm or less, 10 nm or less, 50 nm or less, 100 nm or less, 500 nm or less, 1 um or less, 2 um or less, 3 um or less, 4 um or less, 5 um or less, or in a range between any two of these values.

Protrusion also served as spacers. In certain embodiments, the protrusion for analyte concentration also served as the spacer that regulate the spacing between the two plates. The protrusion then can have the similar characteristics of the spacer specified herein, such as the flat top, significantly uniform height. In these cases, the analyte concentration area on the sidewall of the protrusion (which also serves as the spacer) can catch the analytes.

In some embodiments, the area density of the concentrating protrusions on the inner surface is 1 per $mm^2$ or less, 2 per $mm^2$ or less, 5 per $mm^2$ or less, 10 per $mm^2$ or less, 50 per mm2 or less, 100 per $mm^2$ or less, 200 per $mm^2$ or less, 500 per $mm^2$ or less, 1000 per mm2 or less, $1 \times 10^3$ per $mm^2$ or less, $2 \times 10^3$ per $mm^2$ or less, $3 \times 10^3$ per $mm^2$ or less, $5 \times 10^3$ per $mm^2$ or less, $10 \times 10^3$ per mm2 or less, $2 \times 10^3$ per $mm^2$ or less, $3 \times 10^3$ per mm2 or less, $5 \times 10^3$ per mm2 or less, $10 \times 10^3$ per $mm^2$ or less, $1 \times 10^5$ per $mm^2$ or less, $5 \times 10^5$ per $mm^2$ or less, $1 \times 10^6$ per $mm^2$ or less, or in a range between any two of these values.

In some embodiments, the protrusion (nano or micro islands) has an average lateral dimension of 10 nm or less, 50 nm or less, 100 nm or less, 200 nm or less, 500 nm or less, or in a range between any two of these values.

In some embodiments, the average lateral dimension of the protrusion (nano or micro islands) is 0.5 um or less, 1 um or less, 2 um or less, 5 um or less, 10 um or less, 50 um or less, 100 um or less, 300 um or less, 500 um or less or in a range between any two of these values.

In some embodiments, the height of the protrusion (nano or micro islands) is 10 nm or less, 50 nm or less, 100 nm or less, 200 nm or less, 500 nm or less, or in a range between any two of these values.

In some embodiments, the height of protrusion (nano or micro islands) is 0.5 um or less, 1 um or less, 2 um or less, 5 um or less, 10 um or less, 50 um or less, 100 um or less, 300 um or less, 500 um or less, or in a range between any two of these values.

In some embodiments, the ratio of the spacing between two plates at the closed configuration versus the height of the concentrating protrusion is 1 or less, 1.1 or less, 1.2 or less, 1.5 or less, 2 or less, 3 or less, 5 or less, 10 or less, 15 or less, 20 or less, 30 or less, 40 or less, 50 or less, 60 or less, 80 or less, 100 or less, 200 or less, 300 or less, 400 or less, 500 or less, 600 or less, 800 or less, 1000 or less, or in a range between any two of these values.

In some embodiments, the height of the concentrating protrusion is 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, 300 um or more, 500 um or more, or in a range between any two of these values.

Additional Embodiments

Figure 6:
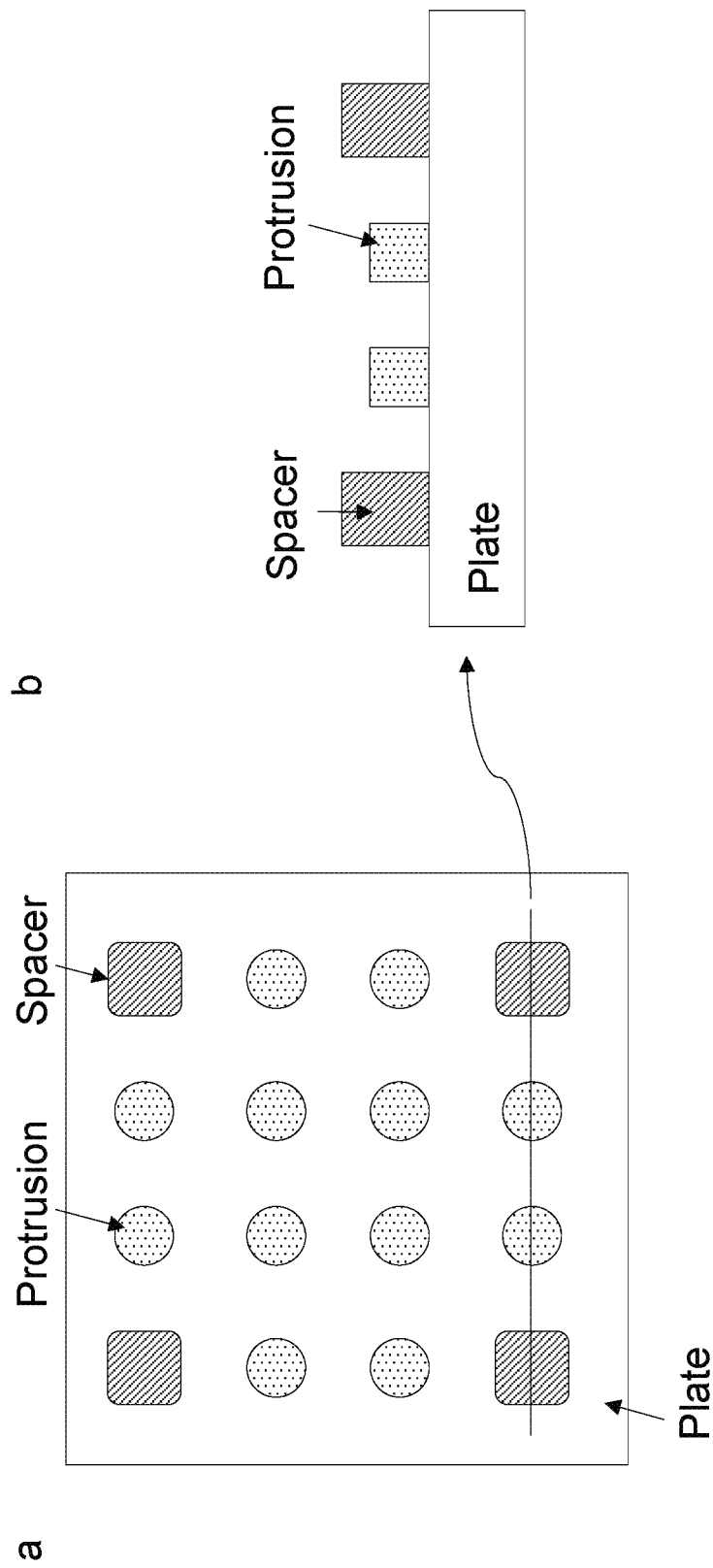
FIG. 6 illustrates schematic drawings for exemplary embodiments of the device for homogeneous assay with "protrusion" pillars and "spacer" pillars on the plate. (a) Top view and (b) cross sectional view.

FIG. 6 shows schematic drawings for exemplary embodiments of the device for homogeneous assay with "protrusion" pillars and "spacer" pillars on the plate. (a) Top view and (b) cross sectional view. As shown in the figure, protrusion pillars have a smaller height than the spacers in the device. In some embodiments, the protrusions and the spacers have similar shapes, while in other embodiments, their shapes are different.

In some embodiments, only the top surface of the protrusions has the concentrating area. In some embodiments, only the side surface(s) of the protrusions has/have the concentrating area. In some embodiments, there are 1, 2, 3, 4, 5, 6, 7 or more side surfaces of the protrusions have the concentrating area. In some embodiments, both the top surface and a number of the protrusions have the concentrating area. In some embodiments, all the surfaces of the protrusions have the concentrating area. The exact number and location of the surfaces having the concentrating area (i.e. coated with capture agent) determines the concentrating efficiency, therefore is subject to empirical test and adjustment.

In some embodiments, the protrusion on the plate have analyte concentration area (ACA) on one or several of its surfaces. In some embodiments, the analyte concentration area (ACA) on the protrusion is created by the surface coating.

Figure 7:
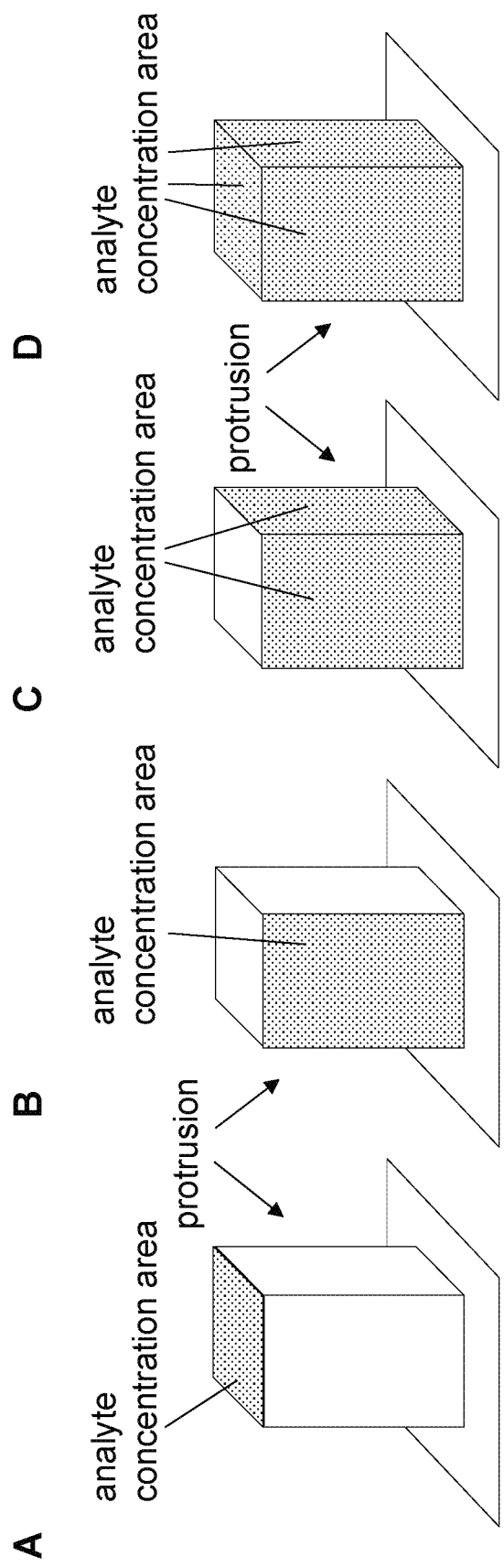
FIG. 7 illustrates schematic drawings for exemplary embodiments of analyte concentration area (ACA) created by surface coating on the protrusions: (a) coating on the top surface of the protrusion; (b) coating on one side or several side surfaces of the protrusion; (c) coating on all the side surfaces of the protrusion; and (d) coating on all the surfaces of the protrusion, to create the analyte concentration area (ACA).

FIG. 7 shows schematic drawings for exemplary embodiments of analyte concentration area (ACA) created by surface coating on the protrusions: (a) coating on the top surface of the protrusion; (b) coating on one side or several side surfaces of the protrusion; (c) coating on all the side surfaces of the protrusion; and (d) coating on all the surfaces of the protrusion.

The methods of selectively coating a surface or several surfaces of the protrusion include, but not limited to, (a) touching the one or several surfaces of the protrusion with a reagent on a surface of a coating device, wherein the reagent comprises the capture agent that is configured to selectively bind to the labeled analyte/bound label and/or the analyte to be labeled;

(b) evaporating the one or several surfaces of the protrusion with a binding layer, wherein the binding layer binds the capture agent when immersing the device in the reagent;

(c) evaporating the one or several surfaces of the protrusion and/or back plane with a binding-prohibition layer, wherein the surfaces with the binding-prohibition layer are prevented by the from binding the capture agent, while the surfaces without the binding-prohibition layer are capable of binding the capture agent; and (d) combination of above methods.

Figure 8:
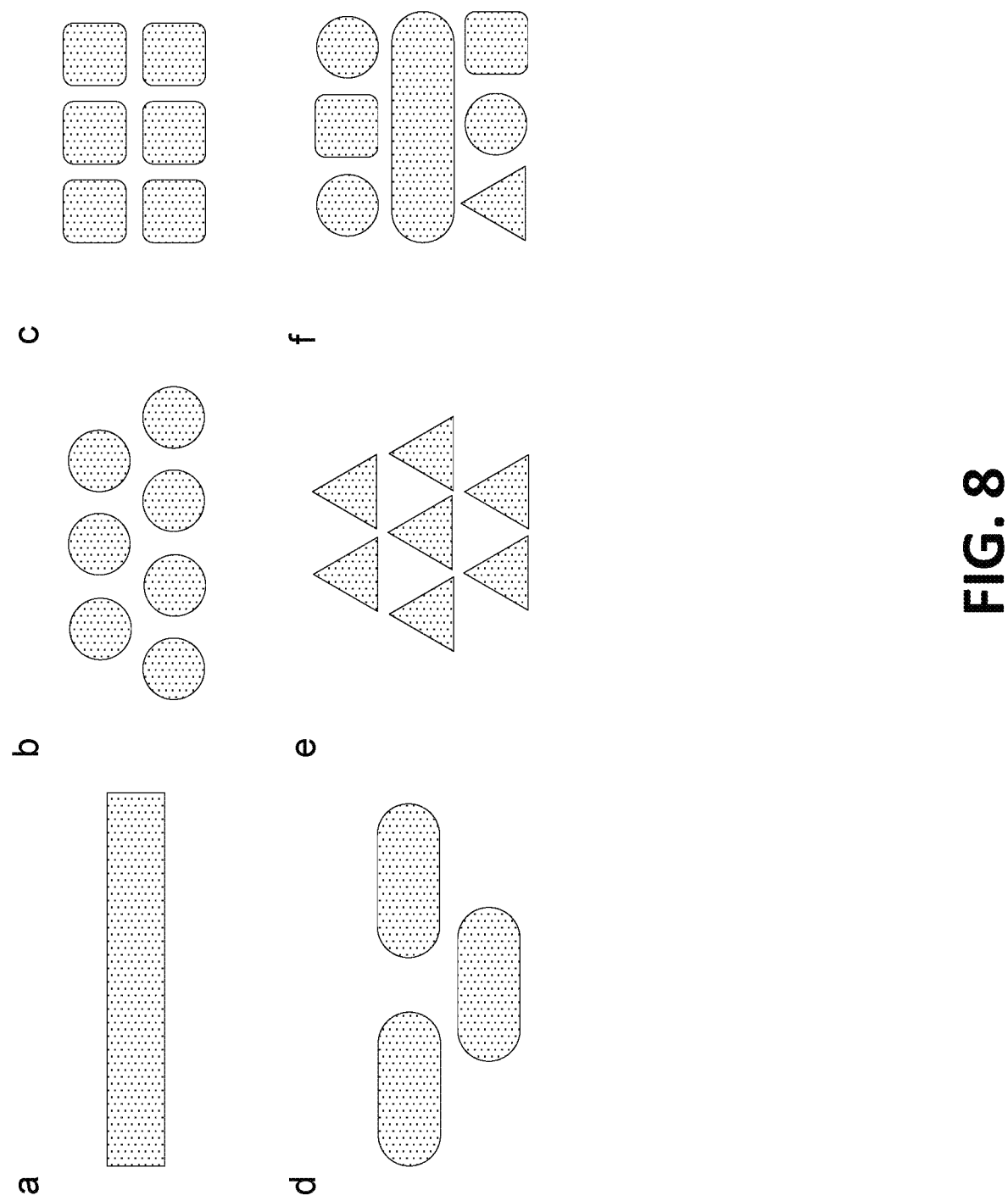
FIG. 8 illustrates schematic drawings for exemplary embodiments of the shapes of the protrusions from the top view: (a) line shape protrusion; (b) circle dots shape protrusion; (c) square dots shape protrusion; (d) bar shape protrusion; (e) triangular shape protrusion; and (f) combination of the above.

In some embodiments, the protrusion (nano or micro islands) have a pillar shape. The shape of the top surface of the pillar can be round, a point (of a pyramid), polygon, elliptical, elongated bar, polygon, other similar shapes or combinations thereof. FIG. 8 shows schematic drawings for exemplary embodiments of the shapes of the protrusions from the top view: (a) line shape protrusion; (b) circle dots shape protrusion; (c) square dots shape protrusion; (d) bar shape protrusion; (e) triangular shape protrusion; and (f) combination of the above.

Figure 9:
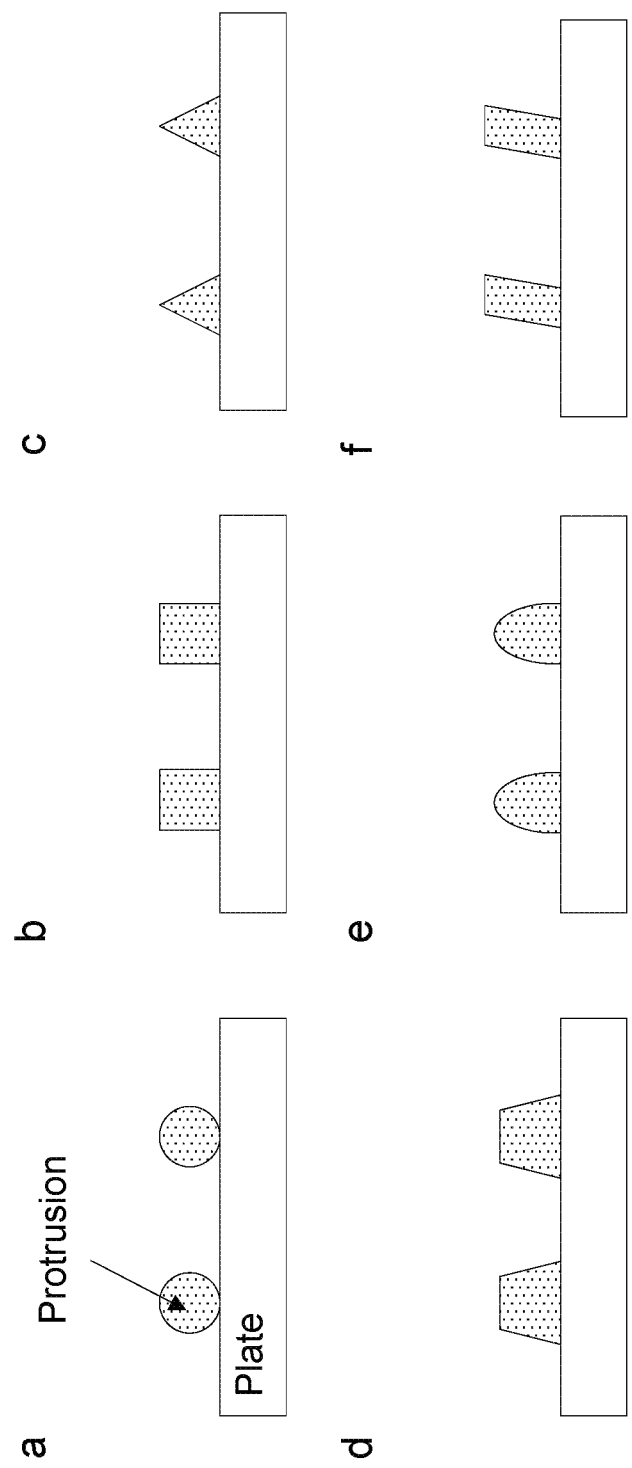
FIG. 9 illustrates schematic drawings for exemplary embodiments of the shapes of protrusions from the side view: (a) circle shape protrusion; (b) square shape protrusion; (c) pyramid shape protrusion; (d) trapezoid shape protrusion; (e) ellipse shape protrusion; and (f) parallelogram shape protrusion.

In some embodiments, the shape of the side surface of the protrusion can be round, a point (of a pyramid), polygon, elliptical, elongated bar, polygon, other similar shapes or combinations thereof. FIG. 9 shows schematic drawings for exemplary embodiments of the shapes of protrusions from the side view: (a) circle shape protrusion; (b) square shape protrusion; (c) pyramid shape protrusion; (d) trapezoid shape protrusion; (e) ellipse shape protrusion; and (f) parallelogram shape protrusion.

2.3 RHA with Concentration Beads

A device for concentrating labeled analyte/bound label, comprises: two plates (or an enclosed channel) with a sample (that has an analyte) sandwiched between the two plates, wherein one bead or a plurality of beads is placed in the sample, wherein the bead has an analyte concentration area on the bead's surface, wherein the analyte concentration area has a capture agent selectively binds the labeled analyte/bound label and/or the analyte to be labeled.

In some embodiments, the beads, the ratio of the spacing between the two plate and the diameter of the beads is 1, 1.1, 1.2, 1.3, 1.5, 2, 5, 10, 20, 30, 50, 100, or in a range between any two of these values.

One aspect of the present invention provides a device for homogeneous assay with concentration beads. In some embodiments, the device comprises: a first plate, a second plate, and spacers. In some embodiments, the plates are movable relative to each other into different configurations, including an open configuration and a closed configuration. In some embodiments, each of the plates has, on its respective inner surface, a sample contact area for contacting a sample suspected of comprising an analyte. In some embodiments, one or both of the plates comprise the spacers, at least one of the spacers is inside the sample contact area, and the spacers have a predetermined substantially uniform height. In some embodiments, one or both of the plates comprise, on the respective inner surface, a plurality of beads that have capture agent immobilized thereon, wherein the capture agent is capable of binding to and immobilizing the analyte. In some embodiments, one or both of the plates comprise, on the respective inner surface, detection agent that is configured to, upon contacting the sample, be dissolved in the sample and bind to the analyte.

In some embodiments, in the open configuration, the two plates are partially or entirely separated apart, the spacing between the plates is not regulated by the spacers, and the sample is deposited on one or both of the plates.

In some embodiments, in the closed configuration, which is configured after deposition of the sample in the open configuration: at least part of the sample is compressed by the two plates into a layer of highly uniform thickness, and the uniform thickness of the layer is confined by the inner surfaces of the plates and is regulated by the plates and the spacers.

In some embodiments, the capture agent and the detection agent are configured to bind to the analyte at different locations thereof and to form a capture agent-analyte-detection agent sandwich that is immobilized to the bead.

In some embodiments, the analyte in the layer of uniform thickness is concentrated by the beads so that signal of the captured analyte on the beads is distinguishable from signal emanating from other area in the layer of uniform thickness.

In some embodiments, the beads have a spherical shape. In some embodiments, the beads have a shape of tube, sphere, cylinder, cube, ellipsoid, cone, tetrahedron, dodecahedron, octahedron, triangular prism, torus, pyramid, or any other shapes, or any combination thereof.

In some embodiments, the bead size, capture agent density on the beads, the detection agent concentration are the factors that are among the important factors that affect the distinguishability of the signal of the bound detection agent from the free detection agent.

In some embodiments, the beads are made of a material selected from the group consisting of: polystyrene, polypropylene, polycarbonate, PMMA, PC, COC, COP, glass, resin, aluminum, gold or other metal or any other material whose surface can be modified to be associated with the capture agent.

In some embodiments, the beads are the spacers that regulate the thickness of the layer at the closed configuration.

In some embodiments, the beads and the detection agent are on the same plate. In some embodiments, the beads and the detection agent are on different plates.

In some embodiments, the beads are micro- or nano-particles. In some embodiments, the beads have an average diameter of 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, or in a range between any two of these values. In some preferred embodiments, the beads have an average diameter of 0.1 um or more, 0.2 um or more, 0.5 um or more, 1 um or more, 2 um or more, 3 um or more, 5 um or more, 10 um or more, or in a range between any two of these values.

In some embodiments, the beads have an area density of 1 per $mm^2$ or more, 2 per $mm^2$ or more, 5 per mm2 or more, 10 per mm2 or more, 50 per mm2 or more, 100 per mm2 or more, 200 per mm2 or more, 500 per mm2 or more, 1000 per mm2 or more, $2 \times 10^3$ per $mm^2$ or more, $3 \times 10^3$ per $mm^2$ or more, $5 \times 10^3$ per $mm^2$ or more, $10 \times 10^3$ per $mm^2$ or more, $1 \times 10^5$ per $mm^2$ or more, $5 \times 10^5$ per $mm^2$ or more, $1 \times 10^6$ per $mm^2$ or more, or in a range between any two of these values.

In some embodiments, the beads are aligned on the plate inner surface in periodic or aperiodic arrays. In some embodiments, the period (the spacing between adjacent beads in periodic arrays) is 2 nm or less, 5 nm or less, 10 nm or less, 50 nm or less, 100 nm or less, 500 nm or less, 1000 nm or less, 2000 nm or less, 4000 nm or less, or in a range between any two of these values. In some embodiments, the average spacing between adjacent beads in aperiodic arrays is 2 nm or less, 5 nm or less, 10 nm or less, 50 nm or less, 100 nm or less, 500 nm or less, 1000 nm or less, 2000 nm or less, 4000 nm or less, or in a range between any two of these values.

In some embodiments, the beads are configured to have a concentration in the layer of uniform thickness of $1 \times 10^3$/uL or more, $5 \times 10^3$/uL or more, $1 \times 10^4$/uL or more, $5 \times 10^4$/uL or more, $1 \times 10^5$/uL or more, $5 \times 10^5$/uL or more, $1 \times 10^6$/uL or more, $5 \times 10^6$/uL or more, $1 \times 10^7$/uL or more, $5 \times 10^7$/uL or more, $1 \times 10^8$/uL or more, $5 \times 10^8$/uL or more, $1 \times 10^9$/uL or more, or in a range between any two of these values.

In some embodiments, it is preferable to have the beads forming one single layer in the layer of uniform thickness. In some embodiments, the product of beads concentration, top area size of one bead and spacing size between plates is 1 or less, 0.9 or less, 0.8 or less, 0.7 or less, 0.6 or less, 0.5 or less, 0.4 or less, 0.3 or less, 0.2 or less, 0.1 or less, 0.08 or less, 0.06 or less, 0.04 or less, 0.01 or less, 0.008 or less, 0.006 or less, 0.004 or less, 0.002 or less, 0.001 or less, or in a range between any two of these values.

In some embodiments, the ratio of the spacing between two plates at the closed configuration versus the height (thickness) of the beads is 1 or less, 1.1 or less, 1.2 or less, 1.5 or less, 2 or less, 3 or less, 5 or less, 10 or less, 15 or less, 20 or less, 30 or less, 40 or less, 50 or less, 60 or less, 80 or less, 100 or less, 200 or less, 300 or less, 400 or less, 500 or less, 600 or less, 800 or less, 1000 or less, or in a range between any two of these values.

In some embodiments, the height (thickness) of the beads is 1 nm or more, 5 nm or more, 10 nm or more, 50 nm or more, 100 nm or more, 200 nm or more, 500 nm or more, 1 um or more, 2 um or more, 5 um or more, 10 um or more, 30 um or more, 50 um or more, 100 um or more, 150 um or more, 200 um or more, 300 um or more, 500 um or more, or in a range between any two of these values.

In some embodiments, the beads have signal amplification properties. In some embodiments, the beads are configured to amplify a signal of the analyte and/or the detection agent in proximity of the beads. In some embodiments, the beads amplify the signal that is at a distance of 0-1 um from the bead surface. In some embodiments, the distance is very small (e.g. 20 nm, 50 nm, or 100 nm). In some embodiments, the beads have a signal amplification factor of 1 or more, 2 or more, 5 or more, 10 or more, 20 or more, 30 or more, 50 or more, 100 or more, 200 or more, 500 or more, 1000 or more, 5000 or more, 10000 or more, or in a range between any two of these values.

Another aspect of the present invention provides a method of homogeneous assay. In some embodiments, the method comprises the steps of:

(a) obtaining a sample suspected of containing an analyte;

(b) obtaining a first and second plates that are movable relative to each other into different configurations, including an open configuration and a closed configuration, wherein:
  i. each of the plates has, on its respective inner surface, a sample contact area for contacting the sample,
  ii. one or both of the plates comprise the spacers, and at least one of the spacers is inside the sample contact area;
  iii. one or both of the plates comprise, on the respective inner surface, a plurality of beads that have capture agent immobilized thereon, wherein the capture agent is capable of binding to and immobilizing the analyte; and
  iv. one or both of the plates comprise, on the respective inner surface, detection agent that is configured to, upon contacting the sample, be dissolved in the sample and bind to the analyte;
  wherein the spacers have a predetermined substantially uniform height;

(c) depositing the sample on one or both of the plates when the plates are in an open configuration, wherein in the open configuration the two plates are partially or entirely separated apart and the spacing between the plates is not regulated by the spacers;

(d) after (c), bringing the two plates together and pressing the plates into a closed configuration, wherein in the closed configuration: at least part of the sample is compressed by the two plates into a layer of highly uniform thickness, the uniform thickness of the layer is confined by the inner surfaces of the two plates and is regulated by the spacers and the plates; and (e) while the plates are at the closed configuration, detecting the analyte in the layer of uniform thickness,
  wherein the capture agent and the detection agent are configured to bind to the analyte at different locations thereof and to form a capture agent-analyte-detection agent sandwich that is immobilized to the bead; and
  wherein the beads, the capture agent, and the detection agent are configured to render signal from the bead-associated capture agent-analyte-detection agent sandwich distinguishable from signal of free detection agent in the layer of uniform thickness.

In some embodiments, the sample contact sites are not washed before the imaging step (e).

In some embodiments, the method further comprises washing the sample contact area before the imaging step (e).

In some embodiments, the method further comprises determining the presence of the analyte and/or measuring the amount of the analyte.

Figure 13:
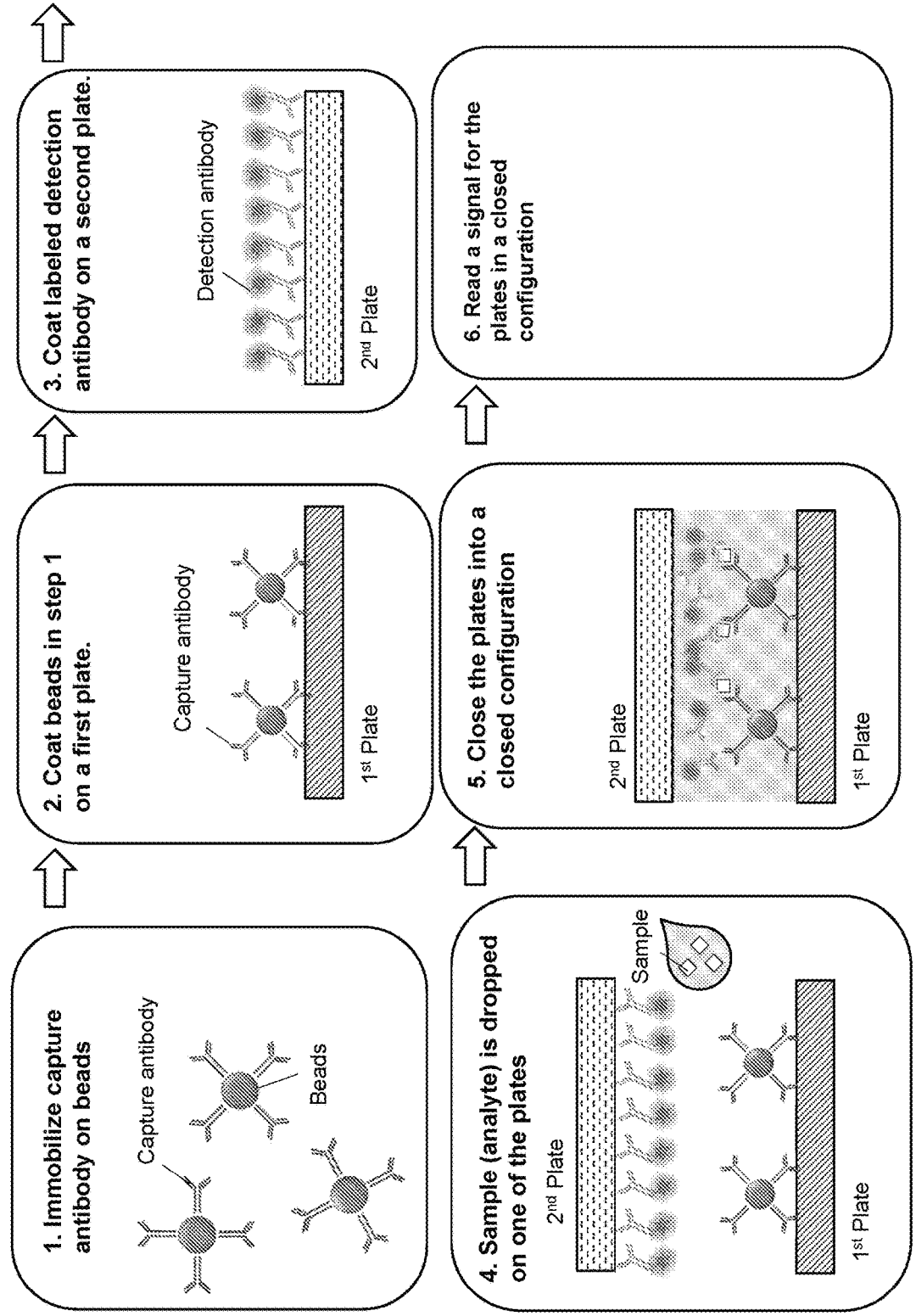
FIG. 13 illustrates schematic illustrations showing some of the exemplary processes of the present invention.

FIG. 13 illustrates some of the exemplary processes according to the present invention. As shown in the figure, the first plate and the second plate are obtained for a homogeneous assay. Before starting the assay, the two plates are pre-treated as follows: capture antibody is first immobilized on the beads, and then these beads are coated on the first plate; while labeled detection antibody is coated on the second plate. For the assay, when the two plates are separated apart (in the open configuration), a sample suspected of containing the analyte is deposited on one of the plates (the first or second plate) or both plates (not shown). After the sample deposition, the two plates are then brought together and pressed against each other to enter the closed configuration. As discussed above, the detection antibody, upon contacting the sample, is dissolved in the sample. And in the closed configuration, at least part of the sample is compressed into a layer of uniform thickness. In such a layer of uniform thickness, the capture antibody on the beads and the diffusing detection antibody both bind to the analyte, but at different locations thereof, thereby forming a capture antibody-analyte-detection antibody sandwich. As the detection antibody is labeled with fluorophore (red asterisks), the attraction of the analyte and labeled antibody around the surface of the beads due to antibody-antigen interactions renders the local concentration of fluorescent signal surrounding the beads significantly higher than the ambient background. Imaging is performed 30 seconds after closing the two plates without washing.

Another aspect of the present invention provides a method of analyzing the image for a rapid homogeneous assay. In some embodiments, the method comprises the steps of:

(a) obtaining an image of the signal in the device of embodiment AB1 at the closed configuration, wherein the image is selected from the group consisting of bright field image, dark field image, fluorescence image, and phosphorescence image;

(b) analyzing the image, identifying beads in the image, and extracting information of beads size, signal intensity of beads, distance between beads, distribution of beads, and number of beads;

(c) deducing analyte concentration by analyzing the extracted information from step (b) and calculating parameters of the beads.

In some embodiments, calculated parameter is the average signal intensity from all the tested bead in the device;

In some embodiments, calculated parameter is the highest signal intensity from all the tested bead in the device;

In some embodiments, calculated parameter is the signal intensity distribution from all the tested bead in the device;

In some embodiments, calculated parameter is the counting number of all the tested bead in the device with signal intensity larger than a threshold;

In some embodiments, calculated parameter is the average signal intensity from all the tested bead in a certain area on the device;

In some embodiments, calculated parameter is the highest signal intensity from all the tested bead in a certain area on the device;

In some embodiments, calculated parameter is the signal intensity distribution from all the tested bead in a certain area on the device;

In some embodiments, calculated parameter is the counting number of all the tested bead in a certain area on the device with signal intensity larger than a threshold.

Plate with Significantly Periodically Arranged Beads and Method of Making the Same In certain embodiments, periodically arrangement of the concentrating beads on the plate is advantageous in that: 1) periodicity reduces the chance of bead aggregation; 2) carefully designed inter-bead spacing ensures maximal concentration efficiency when the concentrating space (the space surrounding the bead in which all analytes can be absorbed by the individual bead within a certain period of time, e.g. assay incubation time) of each bead does not significantly overlap with one another, therefore making the maximal use of each individual bead.

Figure 14:
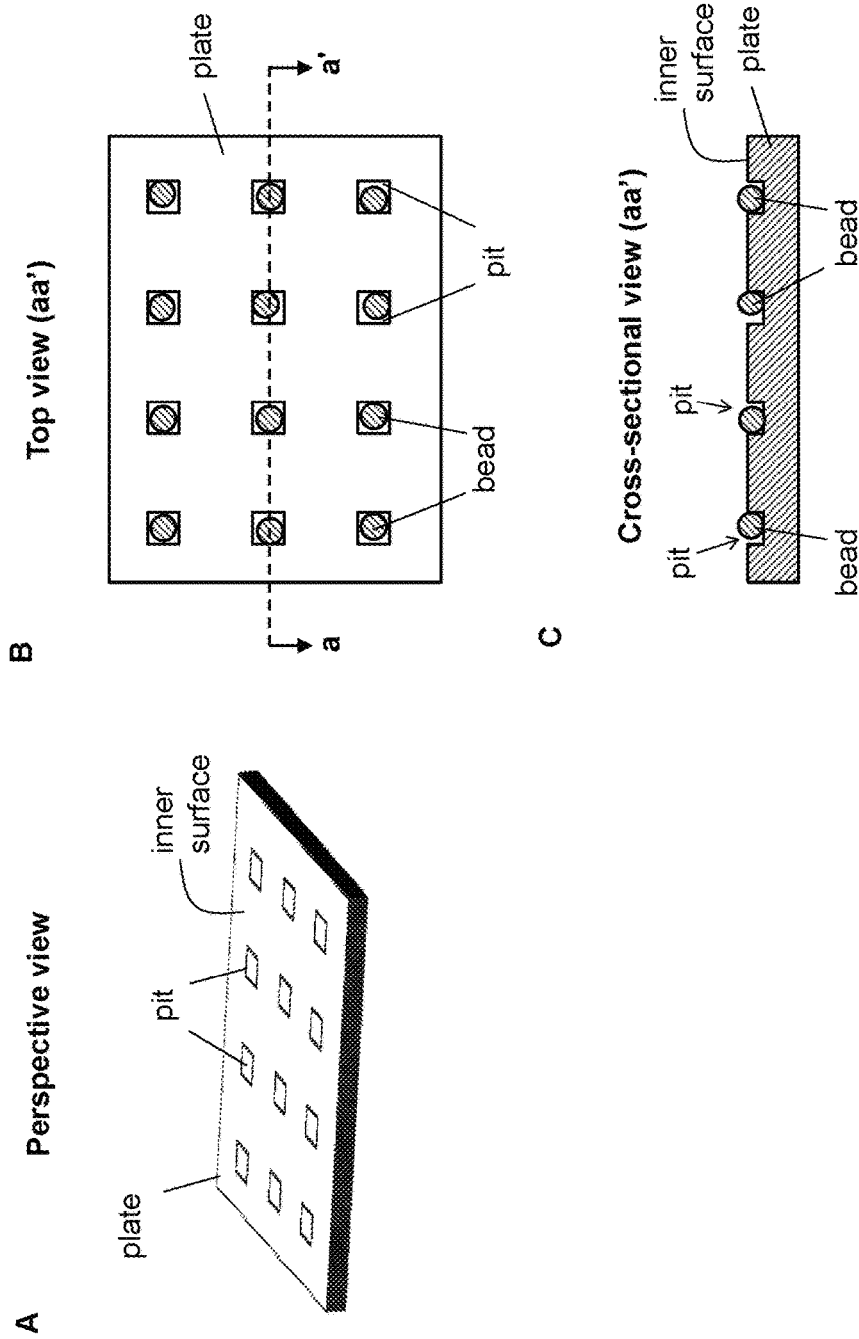
FIG. 14 illustrates one embodiment of the device which have periodically arranged beads on one plate.

FIG. 14 provides schematic illustrations of one embodiment of the device which have periodically arranged beads on one plate. As shown in the figure, the plate comprises a plurality of pits periodically arranged on the inner surface. The plurality of pits have a depth and a lateral shape that are configured to contain one bead per each pit, thereby making the beads periodically arranged on the inner surface of the plate as well.

In some embodiments, the shape of the pits is round, a point (of a pyramid), polygon, elliptical, elongated bar, polygon, other similar shapes or combinations thereof.

In some embodiments, the pits' diameter is 10 nm, 50 nm, 100 nm, 500 nm, 1 um, 2 um, 3 um, 5 um, 10 um, 20 um, 30 um, 50 um, 100 um, 200 um, 500 um or in a range between any of the two values.

In some embodiments, the preferred pits' diameter is 1 um, 2 um, 3 um, 5 um, 10 um, 20 um, 30 um, 50 um, 100 um or in a range between any of the two values.

In some embodiments, the pits' depth is 10 nm, 50 nm, 100 nm, 500 nm, 1 um, 2 um, 3 um, 5 um, 10 um, 20 um, 30 um, 50 um, 100 um, 200 um, 500 um or in a range between any of the two values.

In some embodiments, the preferred pits' depth is 500 nm, 1 um, 2 um, 3 um, 5 um, 10 um, 20 um, 30 um, 50 um or in a range between any of the two values.

In some embodiments, the inter-pit spacing is 10 nm, 50 nm, 100 nm, 500 nm, 1 um, 2 um, 3 um, 5 um, 10 um, 20 um, 30 um, 50 um, 100 um, 200 um, 500 um or in a range between any of the two values.

In some embodiments, the preferred inter-pit spacing is 1 um, 5 um, 10 um, 20 um, 30 um, 50 um, 100 um, 150 um, 200 um or in a range between any of the two values.

In some embodiments, it is preferred that the pits are hydrophilic. In some embodiments, the liquid contact angle (wetting property) of the pits plate is 5 degree, 10 degree, 20 degree, 30 degree, 60 degree, 80 degree, or in a range between any of the two values. In some embodiments, the liquid contact angles of the pits and other area on the plate are different, where the difference is 0 degree, 20 degree, 30 degree, 60 degree, 80 degree, or in a range between any of the two values.

Another aspect of the present invention is to provide a method of making a plate with beads significantly periodically arranged thereon. The method provides a self-assembly process for the beads to be distributed into each individual pit on the plate.

Figure 15:
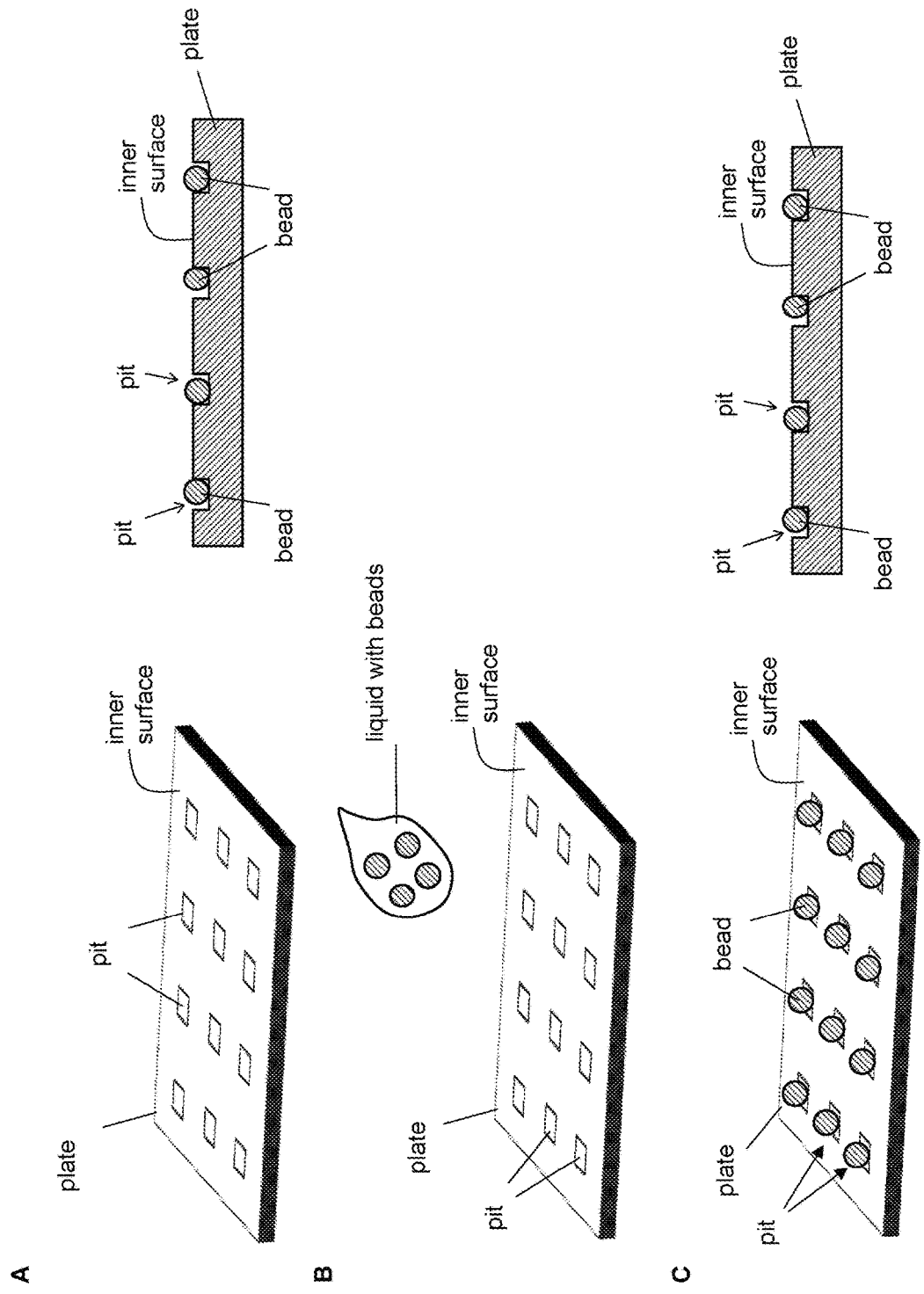
FIG. 15 illustrates an exemplary process of making beads significantly periodically arranged on a plate.

FIG. 15 provides schematic illustration of an exemplary process of making beads significantly periodically arranged on a plate. As shown in the figure, the first step is to have a plate that has a plurality of pits periodically arranged on the plate's inner surface. Next, depositing a liquid that contains a plurality of beads on the inner surface of the plate. Last, drying the plate.

In some embodiments, the plate (pit plate) is hydrophilic. In some embodiments, the pits are hydrophilic. Initially during the drying process, due to capillary force on the ridge of the pit holding the liquid, the liquid film on the plate inner surface starts to dry out and shrink from the non-pit flat area of the inner surface, while the liquid inside the pits remains. Later, as the liquid continues to dry out, the film breaks into droplets that are either on the non-pit flat area, inside the pits, or partially covering both pit and the neighboring flat area. The droplets inside the pits have a low surface energy compared with the droplets on the flat area and the droplets partially covering both pit and the neighboring flat area. As a result of a combinatory action of the capillary force, the difference in surface energy, and potentially many other factors, the beads that are randomly distributed on the plate inner surface (mostly on the non-put flat area) are pushed into their neighboring pits. As the liquid continues to dry, the pits eventually become dry as well, while the beads are now located inside the periodically arranged pits.

In some embodiments, the beads are significantly periodically arranged. The term "significantly" as used herein in reference to the arrangement of the beads on the plate means that the percentage of the bead that are periodically arranged over the total number of beads on the plate is 50% or more, 60% or more, 70% or more, 80% or more, 90% or more, 95% or more, 96% or more, 97% or more, 98% or more, 99% or more, or 100%. In some embodiments, there are a certain number of pits that do not have beads therein. In some embodiments, the percentage of pits that do not have beads therein over the total number of pits on the sample contact area is 90% or less, 80% or less, 70% or less, 60% or less, 50% or less, 40% or less, 30% or less, 20% or less, 10% or less, 5% or less, 4% or less, 3% or less, 2% or less, 1% or less, or 0. In some embodiments, there are beads that are not inside the pits, but rather on the non-pit flat area of the plate. In some embodiments, the percentage of the beads that are not inside the pits, but on the non-pit flat area of the sample contact area of the plate is 50% or less, 40% or less, 30% or less, 20% or less, 10% or less, 5% or less, 4% or less, 3% or less, 2% or less, 1% or less, or 0.

2.4 Homogeneous Nucleic Acid Hybridization Assay

In addition to immunoassays, the present invention also finds use in homogeneous nucleic acid hybridization assays.

In some embodiments, in nucleic acid hybridization assays, the capture agent is oligonucleotide or oligomimetics capture probe. In some embodiments of the present invention, the concentration surface, protrusions, or beads are coated with the capture probes. The capture probes are complementary to one part of the nucleic acid analyte, therefore capturing the analyte to the surface. Further, the analyte is bound with a labeled detection probe that is complementary to another part of the analyte.

Figure 16:
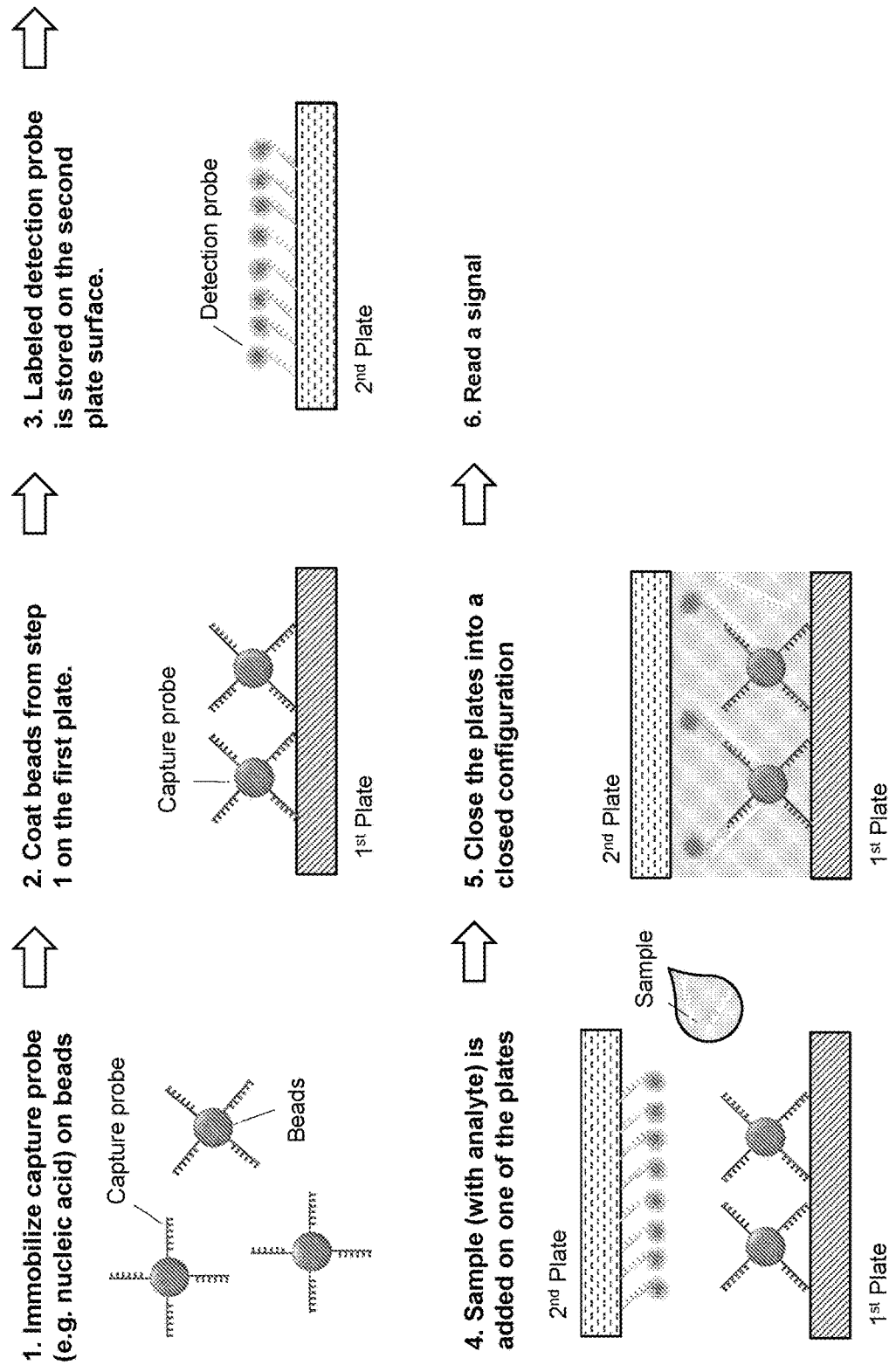

FIG. 16 provides schematic illustrations showing some of the exemplary processes of the beads-enhanced speed test (BEST) for homogeneous nucleic acid hybridization assay, according to some embodiments of the present invention. As shown in the figure, the first plate and the second plate are obtained for a homogeneous nucleic acid hybridization assay. Before starting the assay, the two plates are pretreated as follows: capture probe is first immobilized on the beads, and then these beads are coated on the first plate; while labeled detection probe is coated on the second plate. For the assay, when the two plates are separated apart (in the open configuration), a sample suspected of containing the nucleic acid analyte is deposited on one of the plates (the first or second plate) or both plates (not shown). After the sample deposition, the two plates are then brought together and pressed against each other to enter the closed configuration. As discussed above, the detection probe, upon contacting the sample, is dissolved in the sample. And in the closed configuration, at least part of the sample is compressed into a layer of uniform thickness. In such a layer of uniform thickness, the capture probe on the beads and the diffusing detection probe both hybridize to the analyte, but at different locations thereof, thereby forming a capture probe-analyte-detection probe sandwich. As the detection probe is labeled with fluorophore (red asterisks), the attraction of the analyte and labeled probe around the surface of the beads due to base-pair interactions renders the local concentration of fluorescent signal surrounding the beads significantly higher than the ambient background. Imaging is performed after closing the two plates without washing.

In some embodiments, for the nucleic acid hybridization assays, the beads have a diameter of 100 nm, 500 nm, 1 µm, 5 µm, 50 µm, 500 µm, 1 mm or in a range between any two of the values. In some preferred embodiments, the beads have a diameter of in a range of 1 µm to 10 µm, or 10 µm to 50 µm.

In some embodiments, for the nucleic acid hybridization assays, the beads are made of polysteryne, polypropylene, polycarbonate, glass, metal or any other material whose surface can be modified to bind capture antibody, or any combination thereof.

In some embodiments, the concentration surface, protrusion, or beads are blocked by blocking agent that is configured to reduce the non-specific binding to the concentration surface, protrusion, or beads. In some embodiments, the blocking agent comprises bovine serum albumin (BSA), milk, sodium caseinate, or any other reagent that can block the non-specific binding, or any combination thereof.

Below is an exemplary procedure for homogeneous nucleic acid hybridization assay using the BEST technology according to some embodiments of the present invention:

1. Conjugation of capture probe to beads. Biotinylated capture probes are coated on streptavidin coated beads (Piece, 10 µm in diameter);
2. Blocking of beads. The capture probe coated beads are blocked by 4% BSA in PBS at 4° C. over night and washed by PBST for 6 times prior to use;
3. Coating first plate. 1 µL of beads from Step 2 (beads concentration $10^7$-$10^8$/mL) are dropped on glass slide (Fisher Scientific) and air dried at room temperature;
4. Homogeneous assay. 1 µL of sample containing target nucleic acid of interest and 1 µL of Cy5-labeled detection probe are dropped onto the area of coated beads on the glass slide. The mix is immediately covered by X-plate (second plate) with 10 µm pillars and incubated for 1 min;
5. Imaging. Without washing, the fluorescent images are taken by fluorescence microscope.

2.5 RHA for Homogeneous Competitive Assay

According to some embodiments of the present invention, the RHA also can be used for competitive assays, where the certain area (e.g. analyte concentration area, concentrating protrusion, or beads) capture the unlabeled analyte. In these cases, the unlabeled analyte competes with the labeled detection agent to bind to the capture agent. The signal of the capture analyte is distinguishable from the background signal in that the certain area with the capture agent (e.g. analyte concentration area, concentrating protrusion, or beads) exhibits lower signal level as compared to the unbound labeled detection agent in the background. The homogeneous does not use the step of washing. The homogeneous assay is also one step: drop the sample on one plate and close the plates, ready for reading the signal.

2.6. Hand Pressing

For the devices, apparatus, systems, and methods herein disclosed, human hands can be used for manipulating or handling of the plates and/or samples. In some embodiments, human hands can be used to press the plates into a closed configuration. In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in US Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, the plates are movable relative to each other into different configurations, including an open configuration and a closed configuration. In the open configuration, the two plates are partially or completely separated apart, the spacing between the plates is not regulated by the spacers, and the sample is deposited on one or both of the plates. In the closed configuration, at least part of the sample is compressed by the two plates into a layer of highly uniform thickness and is substantially stagnant relative to the plates, wherein the uniform thickness of the layer is confined by the sample contact areas of the two plates and is regulated by the plates and the spacers. In some embodiments, the force that presses the two plates into the closed configuration is an imprecise pressing force provided by human hand.

In some embodiments, the plates are conformably pressed. Conformable pressing refers to pressing, in certain embodiments by human hand, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers. In certain embodiments, a conformable pressing is a method that makes the pressure applied over an area is substantially constant regardless the shape variation of the outer surfaces of the plates. In certain embodiments, parallel pressing applies the pressures on the intended area at the same time, and a sequential pressing applies the pressure on a part of the intended area and gradually move to other area.

In some embodiments, the plates are pressed into a closed configuration by an imprecise force. In certain embodiments, the imprecise force is applied by human hand. In some embodiments, the force is an imprecise force that has a magnitude which is, at the time that the force is applied, either (a) unknown and unpredictable, or (b) cannot be known and cannot be predicted within an accuracy equal or better than 30% of the force applied. In some embodiments, the force is an imprecise force that has a magnitude which cannot, at the time that the force is applied, be determined within an accuracy equal or better than 30%, 40%, 50%, 70%, 100%, 200%, 300%, 500%, 1000%, 2000%, or any range between the two values.

3. Multiplexed Assays

It is another aspect of the present invention to provide devices and methods with multiplexing capability for homogeneous assays.

In some embodiments, the sample comprises more than one analyte of interest, and there is need to detect the more than one analytes simultaneously using the same device ("multiplexing").

In some embodiments, the device for multiplexed homogeneous assays comprises: a first plate, a second plate, and spacers. In some embodiments, the plates are movable relative to each other into different configurations, including an open configuration and a closed configuration. In some embodiments, each of the plates has, on its respective inner surface, a sample contact area for contacting a sample suspected of containing a first analyte and a second analyte. In some embodiments, one or both of the plates comprise the spacers, at least one of the spacers is inside the sample contact area, and the spacers have a predetermined substantially uniform height. In some embodiments, one or both of the plates comprise, on the respective inner surface, a plurality of first beads and second beads, wherein the first and second beads have first and second capture agents immobilized thereon, respectively. In some embodiments, the first and second capture agents are capable of binding to and immobilizing the first and second analytes, respectively.

In some embodiments, in the open configuration of the device for multiplexed assays, the two plates are partially or entirely separated apart, the spacing between the plates is not regulated by the spacers, and the sample is deposited on one or both of the plates.

In some embodiments, in the closed configuration of the device for multiplexed assays, at least part of the sample is compressed by the two plates into a layer of highly uniform thickness, the uniform thickness of the layer is confined by the inner surfaces of the plates and is regulated by the plates and the spacers, the analytes in the layer of uniform thickness are concentrated by the beads so that signal of the captured analytes on the beads is distinguishable from signal emanating from other area in the layer of uniform thickness.

In some embodiments, the assay is designed to detect analytes of two different species. In some embodiments, the number of analyte species the assay is designed to detect is 3, 4, 5, 6, 7, 8, 10 or more, 20 or more, 30 or more, 100 or more, or an integral number in a range between any two of these values.

In multiplexed assays, it is often critical to distinguish the signals from different assays. In some embodiments of the present invention, the signals of the captured first and second analytes are distinguishable from one another by one of the following designs or methods:

(1) different types of labels are attached to the analytes of different species directly or the different detection agents that bind to the analytes of corresponding species;

(2) different types of beads are used to capture analytes of different species, and the bead types are distinguishable by the detection methods; and (3) a combination of (1) and (2).

In some embodiments, the beads for different analytes (e.g. the first and second beads) are different in their sizes.

In some embodiments, the beads for different analytes (e.g. the first and second beads) are different in their optical properties selected from the group consisting of: photoluminescence, electroluminescence, and electrochemiluminescence, light absorption, reflection, transmission, diffraction, scattering, diffusion, surface Raman scattering, and any combination thereof.

In some embodiments, the beads for different analytes (e.g. the first and second beads) are different in their electric densities, and a detector that can detect electric density is used.

FIGS. 17A-C provide schematic illustrations showing three different exemplary processes of multiplexed homogeneous assays, respectively, according to some embodiments of the present invention.

FIG. 17A shows the case where beads of different colors are used to capture analytes of different species (symbolized by the different shapes in the sample). In this case, a detector with the capability of visualizing or imaging the sample under bright-field illumination is used to facilitate the virtual separation of signals from analytes of different species. For instance, in some embodiments, the bright-field images are superimposed with the fluorescent images to sort out the signals, when the assay signals (signal of the analytes or the bound detection agents) are fluorescent.

FIG. 17B shows the case where beads of different sizes are used to capture analytes of different species (symbolized by the different shapes in the sample). In this case, a detector with the capability of detecting the geometric distribution of the signal of the capture analytes or visualizing or imaging the beads under bright-field illumination is used to facilitate the virtual separation of signals from analytes of different species. For instance, in some embodiments, the assay signals are fluorescent, a detector that can image the fluorescent signals is able to record the geometric distribution of the fluorescent signal on the surface of the beads. A skilled artisan can separate beads of different sizes based on the fluorescent images. In other cases, bright-field images of the beads are used to aid the separation of the signals.

FIG. 17C shows the case where different labels are used to separate analyte of different species (symbolized by the different shapes in the sample). In this exemplary case, different fluorophores are attached to the detection agents that bind to analytes of different species. A detector that can image the sample under fluorescent mode and is equipped with emission filters with different wavelengths of light should be used to distinguish the signals of different analytes.

FIGS. 18A-C provide schematic illustrations showing three different exemplary processes of multiplexed homogeneous nucleic acid hybridization assays, respectively, according to some embodiments of the present invention.

FIG. 18A shows the case where beads of different colors are used to capture analytes of different species (symbolized by the different colors in the sample). In this case, a detector with the capability of visualizing or imaging the sample under bright-field illumination is used to facilitate the virtual separation of signals from analytes of different species. For instance, in some embodiments, the bright-field images are superimposed with the fluorescent images to sort out the signals, when the assay signals (signal of the analytes or the bound detection agents) are fluorescent.

FIG. 18B shows the case where beads of different sizes are used to capture analytes of different species (symbolized by the different colors in the sample). In this case, a detector with the capability of detecting the geometric distribution of the signal of the capture analytes or visualizing or imaging the beads under bright-field illumination is used to facilitate the virtual separation of signals from analytes of different species. For instance, in some embodiments, the assay signals are fluorescent, a detector that can image the fluorescent signals is able to record the geometric distribution of the fluorescent signal on the surface of the beads. A skilled artisan can separate beads of different sizes based on the fluorescent images. In other cases, bright-field images of the beads are used to aid the separation of the signals.

FIG. 18C shows the case where different labels are used to separate analyte of different species (symbolized by the different color in the sample). In this exemplary case, different fluorophores are attached to the detection agents that bind to analytes of different species. A detector that can image the sample under fluorescent mode and is equipped with emission filters with different wavelengths of light should be used to distinguish the signals of different analytes.

4. Assays, Capture Agent, and Detection Agent

In some embodiments, the assay is a sandwich assay, in which capture agent and detection agent are configured to bind to analyte at different locations thereof, forming capture agent-analyte-detection agent sandwich.

In some embodiments, the assay is a competitive assay, in which analyte and detection agent compete with each other to bind to the capture agent.

In some embodiments, the assay is an immunoassay, in which protein analyte is detected by antibody-antigen interaction. In some embodiments, the assay is a nucleic acid assay, in which nucleic acids (e.g. DNA or RNA) are detected by hybridization with complementary oligonucleotide probes.

In some embodiments, the assay utilizes light signals as readout. In some embodiments, the assay utilizes magnetic signals as readout. In some embodiments, the assay utilizes electric signals as readout. In some embodiments, the assay utilizes signals in any other form as readout.

In some embodiments, the light signal from the assay is luminescence selected from photoluminescence, electroluminescence, and electrochemiluminescence. In some embodiments, the light signal is light absorption, reflection, transmission, diffraction, scattering, or diffusion. In some embodiments, the light signal is surface Raman scattering. In some embodiments, the electrical signal is electrical impedance selected from resistance, capacitance, and inductance. In some embodiments, the magnetic signal is magnetic relaxivity. In some embodiments, the signal is any combination of the foregoing signal forms.

Figure 11:
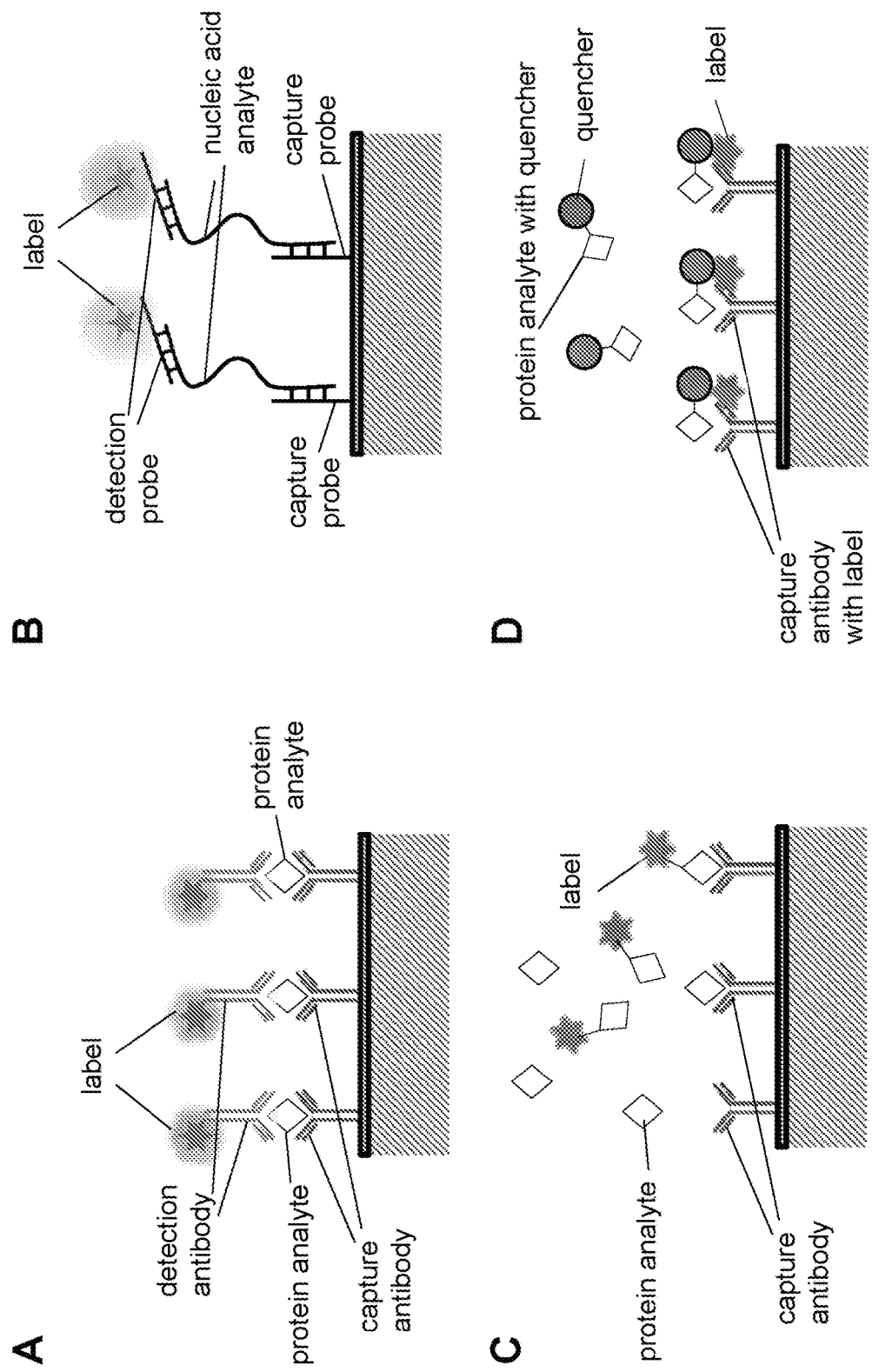
FIG. 11 illustrates examples of analyte concentration surfaces that capture analyte using a capture agent, and the captured analyte are further bound with a label. Panel (A) shows a protein concentration surface, where the capture agent is the capture antibody; panel (B) shows a nucleic acid concentration surface, where the capture agent is the capture probe; panel (C) shows a protein concentration surface, where the protein analyte is directly labeled; panel (D) shows a protein concentration surface, where the protein analyte is labeled with a quencher that quenches signal of the label associated with the capture antibody.

FIG. 11 illustrates examples of analyte concentration surfaces that capture analyte using a capture agent, and the captured analyte are further bound with a label. Panel (A) shows a protein concentration surface, which is coated with capture antibodies. The capture antibodies capture the protein analyte in a sample, which is further bound with labeled detection antibodies. In this case, the capture antibody and detection antibody are configured to bind to the protein analyte at its different locations, therefore forming a capture antibody-protein analyte-detection antibody sandwich. Panel (B) shows a nucleic acid concentration surface, which is coated with oligonucleotide capture probes. The capture probes are complementary to one part of the nucleic acid analyte, therefore capturing the analyte to the surface. Further, the analyte is bound with a labeled detection probe that is complementary to another part of the analyte. Panel (C) shows another case of protein concentration surface, where protein analyte is directly labeled by an optical label and captured by the capture antibodies that are coated on the concentration surface. Panel (D) shows another case of protein concentration surface, where protein analyte is bound with a quencher, which quenches the signal emitted by the label that is associated with the capture antibodies on the concentration surface. In this case, the concentration of the protein analyte to the concentration surface reduces the signal emanating from the concentration surface.

Figure 12:
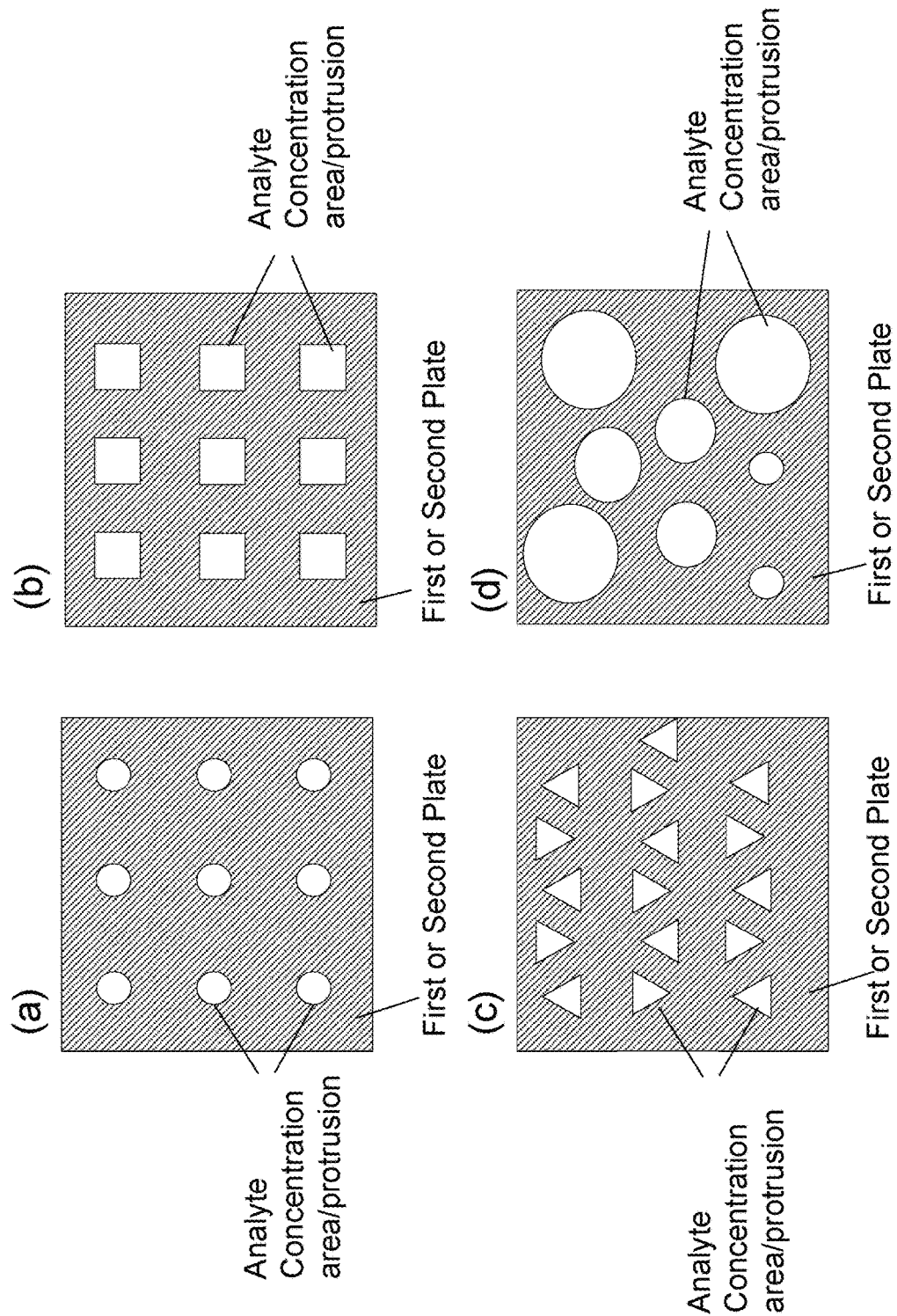
FIG. 12 illustrates a top view of the analyte concentration area/protrusion that are separated nano-/micro-islands on one or both of the plates with (i) round shape with square lattice (ii) rectangle shape with square lattice (iii) triangle shape with hexagonal lattice (iv) round shape with aperiodicity.

In some embodiments, the capture agent and the detection agent are configured to bind to the analyte at different locations thereof and to form a capture agent-analyte-detection agent sandwich that is immobilized to the separated nano-/micro-islands on one or both of the plates; wherein the shape of nano- or micro-islands are selected from the group consisting of sphere, rectangle, hexagon, and/or any other polyhedron, with lattice of square, hexagon, and/or any other lattices. FIG. 12 illustrates top views of separated nano/micro islands on one or both of the plates with (i) round shape with square lattice (ii) rectangle shape with square lattice (iii) triangle shape with hexagonal lattice (iv) round shape with aperiodicity.

In some embodiments, the material of protrusions that are nano or micro islands are selected from the group consisting of plastic as polystyrene, polypropylene, polycarbonate, PMMA, PET; metals as gold, aluminum, silver, copper, tin and/or their combinations; or any other material whose surface can be modified to be associated with the capture agent.

As discussed above, in some embodiments, the beads, the capture agent, and the detection agent are configured to render signal of the bead-captured analyte distinguishable from signal of free detection agent in the layer of uniform thickness. In some embodiments, it is critical to achieve the foregoing configuration, in that only if the signal from the sandwich structure is distinguishable from the "background" signal of the free detection agent in the layer of uniform thickness, one can use the detected signals as a readout of the presence and/or quantity of the analyte in the sample, thereby realizing the assay.

In some embodiments, the target analyte competes with the detection agent on the capture locations on beads. When more target analyte appears, beads become relative dark.

In some embodiments, the beads are associated with a label, and the detection agent is a quencher that is configured to quench signal of the beads-associated label when the detection agent is in proximity of the label. When beads capture the target analyte, the label on beads become quenched or dimed.

In some embodiments, the capture agent includes, but not limited to, protein, peptide, peptidomimetics, streptavidin, biotin, oligonucleotide, oligonucleotide mimetics, any other affinity ligand and any combination thereof. In some embodiments, the capture agent is an antibody. In some embodiments, the capture antibody is an anti-C Reactive Protein (CRP) antibody.

In some embodiments, the capture agent has a concentration that is sufficient to detect the presence and/or measure the amount of the analyte. In some embodiments, the capture agent has a concentration that is sufficient to immobilize the analyte.

In some embodiments, the detection agent includes, but not limited to, protein, peptide, peptidomimetics, streptavidin, biotin, oligonucleotide, oligonucleotide mimetics, any other affinity ligand and any combination thereof. In some embodiments, the detection agent is an antibody. In some embodiments, the detection antibody is an anti-CRP antibody.

In some embodiments, the detection antibody is configured to have a concentration in the layer of uniform thickness that is higher than analyte concentration in the sample. In some embodiments, the ratio of the detection antibody concentration over the analyte concentration is 1 or more, 2 or more, 5 or more, 10 or more, 20 or more, 30 or more, 50 or more, 100 or more, 200 or more, 300 or more, 500 or more, 1000 or more, or in a range between any two of these values.

In some embodiments, the detection antibody is labeled. In some embodiments, the label can be fluorescent, colorimetric or luminescent. In some embodiments, the detection antibody is labeled with a fluorophore. In some embodiments, the fluorophores include, but are not limited to, IRDye8000 W, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; combinations thereof; and the like.

In some embodiments, the beads are treated with a protein stabilizer. In some embodiments, the beads can be deposited on the plate and dried (e.g. air-dried), further simplifying the process. In some embodiments, the detection antibody is placed on one of the plates and dried. In some embodiments, the plate with the detection antibody is treated with protein stabilizer. In some embodiments, the detection antibody with protein stabilizer is pre-printed on one of the plates and air dried.

In some embodiments, wherein the beads are prepared by:
(a) activating with N-Hydroxysuccinimide (NHS);
(b) blocking with a BSA solution; and
(c) incubating with a capture agent solution.

5. Detector, System and Smartphone-Based System

Another aspect of the present invention provides a system for homogeneous assay. In some embodiments, the system comprises the device as discussed above and a detector that detects the analyte in the layer of uniform thickness.

In some embodiments, detector detects a signal from the capture agent-analyte-detection agent sandwich indicative of the presence and/or quantity of the analyte.

In some embodiments, the signal is:
i. luminescence selected from photoluminescence, electroluminescence, and electrochemiluminescence;
ii. light absorption, reflection, transmission, diffraction, scattering, or diffusion;
iii. surface Raman scattering;
iv. electrical impedance selected from resistance, capacitance, and inductance;
v. magnetic relaxivity; or
vi. any combination of i-v.

Another aspect of the present invention provides a smartphone system for homogeneous assay. In some embodiments, the smartphone system comprises:
(a) a device of any aforementioned embodiment;
(b) a mobile communication device that comprises:
 i. one or a plurality of cameras for detecting and/or imaging the sample;
 ii. electronics, signal processors, hardware and software for receiving and/or processing the detected signal and/or the image of the sample and for remote communication; and
(c) an adaptor configured to hold the closed device and engageable to mobile communication device;
wherein when engaged with the mobile communication device, the adaptor is configured to facilitate the detection and/or imaging of the analyte in the sample at the closed configuration.

In some embodiments, the mobile communication device is configured to communicate test results to a medical professional, a medical facility or an insurance company.

In some embodiments, the mobile communication device is further configured to communicate information on the subject with the medical professional, medical facility or insurance company.

In some embodiments, the mobile communication device is configured to receive a prescription, diagnosis or a recommendation from a medical professional.

In some embodiments, the mobile communication device communicates with the remote location via a wifi or cellular network.

In some embodiments, the mobile communication device is a mobile phone.

In some embodiments, the images can be taken by a camera that is part of a mobile device. In some embodiments, the mobile device is a smart phone.

Figure 1A:
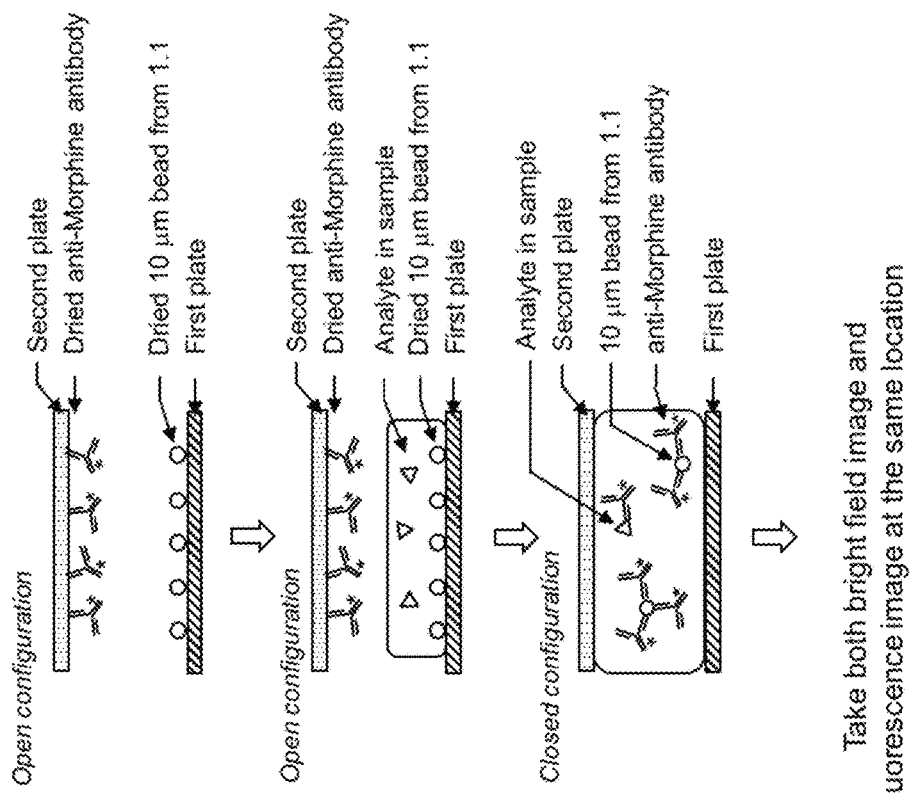
FIG. 1 illustrates an exemplary procedure for a morphine QMAX BEST competitive immunoassay, and QMAX card with two moving plates.
Figure 1A:
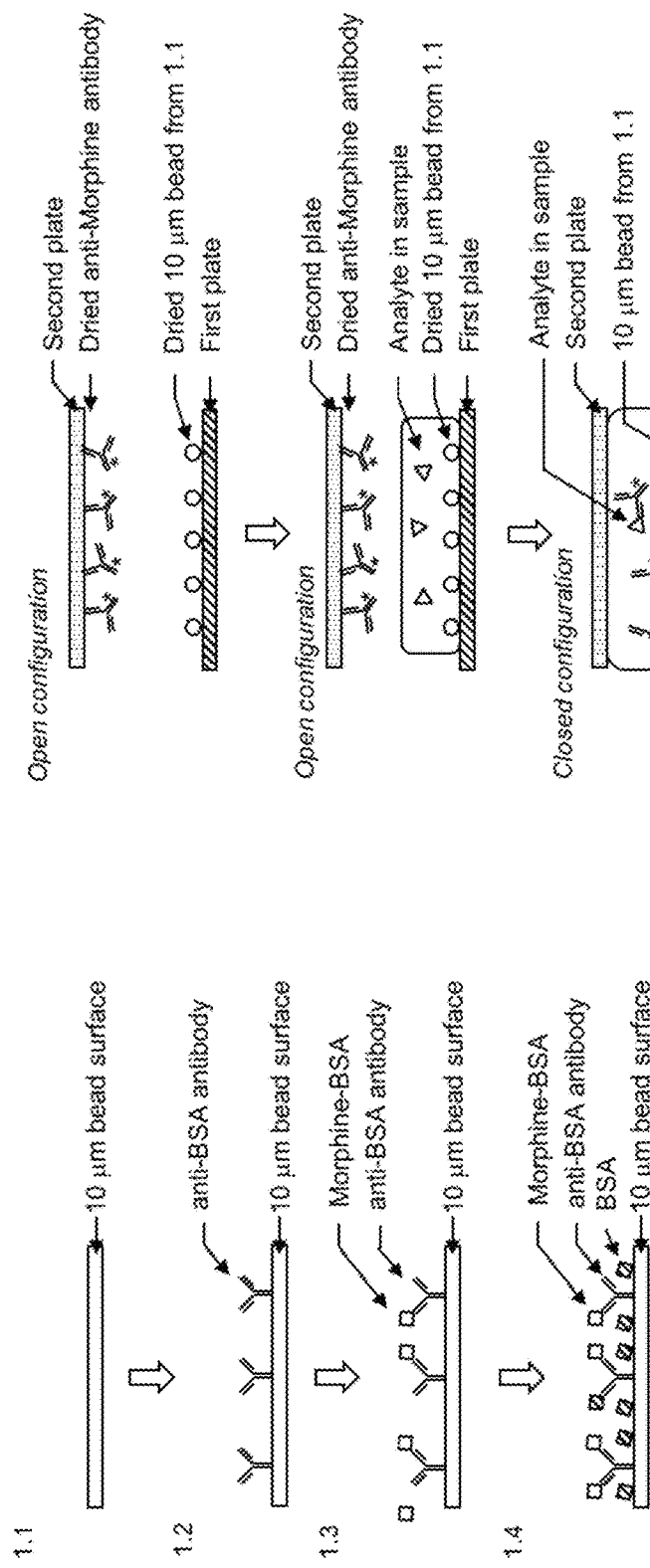
Figure 1B:
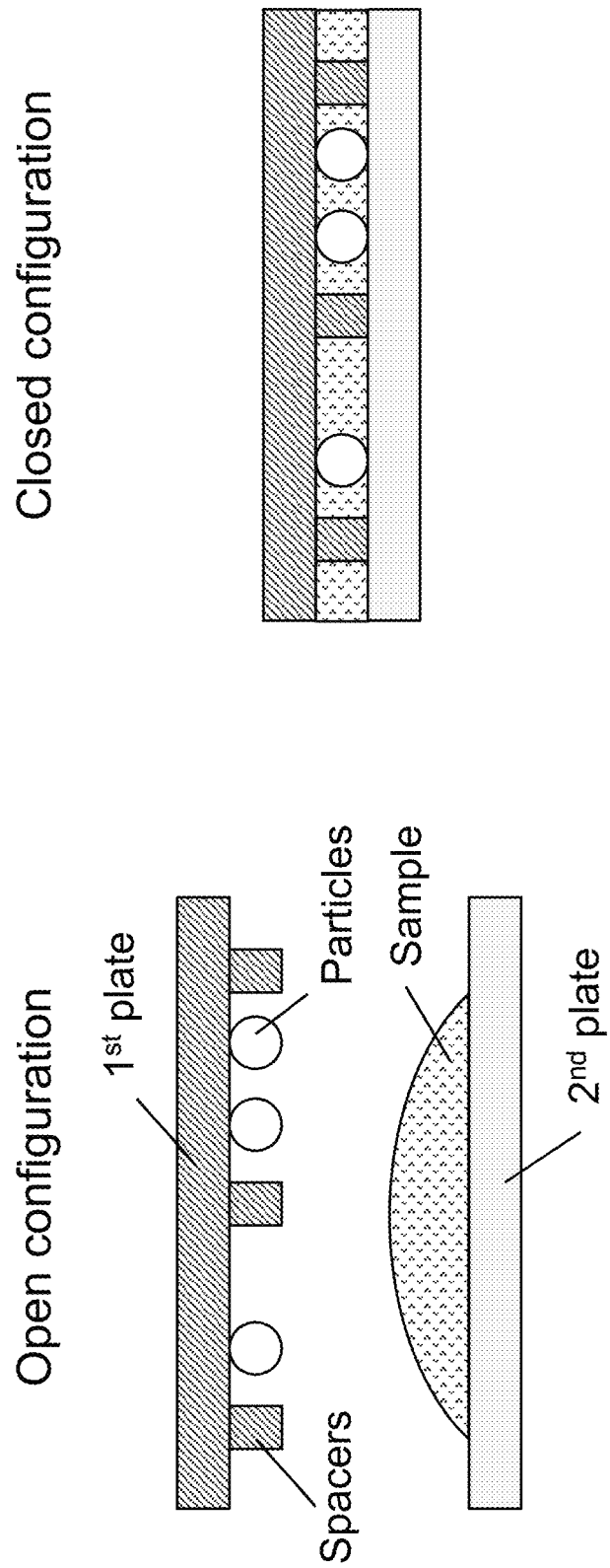
Figure 1C:
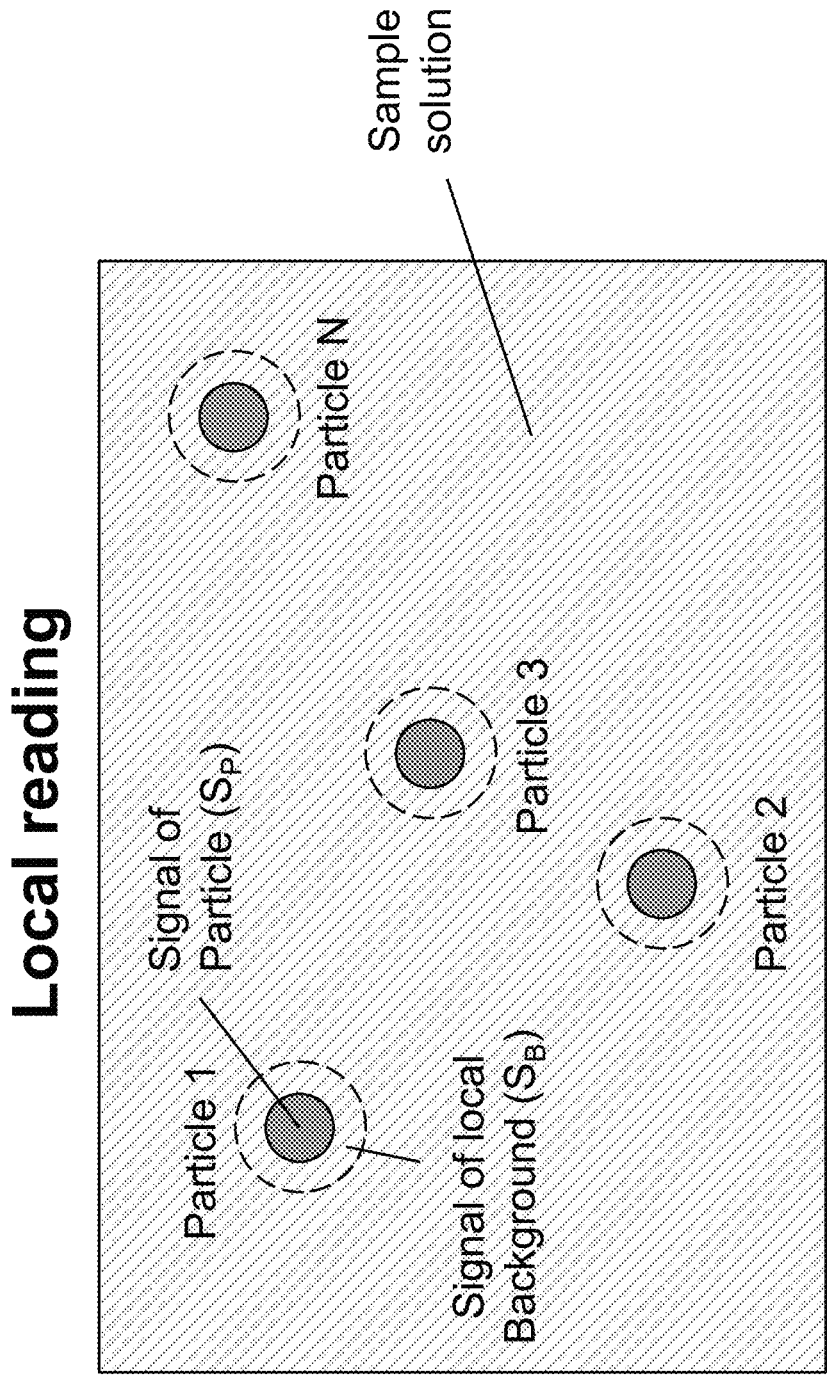

In the local reading approach, as shown in FIG. 1B, one or more than one particles will be measured for the following two measurements: (a) the signal from the particle region ($S_P$). It can be from the whole particle region or a designated area of the particle region; and (b) the signal of area around the particle (local background $S_B$). It can be from the whole area around the particle or a designated area. The definition of "around" can be a distance of 0.01D, 0.1D, 0.2D, 0.5D, 1D, 2D, 5D, 10D, 50D or a range between any two of the values to the outer surface of the particle, in which "D" is the average diameter of the particle. The true Signal of Assay ($S_A$) for each particle can be determined as $S_A = S_P - S_B$. The assay signal from each CROF ($S_{CROF}$) can be the average of multiple particles. It can be all particles on a whole CROF or particles in a designated region of a CROF (e.g., $S_{CROF}$=Average ($S_{A1}, S_{A2}, S_{A3} \ldots S_{An}$))

6. Analyte, Sample and Application

In some embodiments, the analyte to be detected in the homogeneous assay includes, but not limited to, cells, viruses, proteins, peptides, DNAs, RNAs, oligonucleotides, and any combination thereof.

In some embodiments, the present invention finds use in detecting biomarkers for a disease or disease state. In certain instances, the present invention finds use in detecting biomarkers for the characterization of cell signaling pathways and intracellular communication for drug discovery and vaccine development. For example, the present invention may be used to detect and/or quantify the amount of biomarkers in diseased, healthy or benign samples. In certain embodiments, the present invention finds use in detecting biomarkers for an infectious disease or disease state. In some cases, the biomarkers can be molecular biomarkers, such as but not limited to proteins, nucleic acids, carbohydrates, small molecules, and the like. The present invention find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The present invention has applications in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

In some embodiments, the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

In some embodiments, the sample is an environmental gaseous sample from a source selected from the group consisting of: the air, underwater heat vents, industrial exhaust, vehicular exhaust, and any combination thereof.

In some embodiments, the sample is a foodstuff sample selected from the group consisting of: raw ingredients, cooked food, plant and animal sources of food, preprocessed food, and partially or fully processed food, and any combination thereof.

7. Examples of Present Invention

Multiplexed BEST

NA1. A device for a homogeneous assay, comprising:
a first plate, a second plate, spacers, a plurality of particles, and capture agents, wherein:
  vi. the first and second plates are movable relative to each other into different configurations, including an open configuration and a closed configuration;
  vii. each of the plates has, on its respective inner surface, a sample contact area for contacting a sample suspected of containing an analyte;
  viii. the first plate comprises the spacers that are fixed on its inner surface, at least one of the spacers is inside the sample contact area, the spacers have a predetermined substantially uniform height that is equal to 100 um or less;
  ix. the plurality of particles has the capture agents immobilized on their surface, wherein the capture agents are capable of specifically binding and immobilizing the analyte; and
  x. the plurality of particles are (a) distributed on the sample contact area of the first plate, except the areas occupied by the spacers, and (b) are temporarily or permanently fixed on the first plate;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

NB1. A device for a homogeneous assay, comprising:
a first plate, a second plate, spacers, a plurality of particles, and capture agents, wherein:
  vi. the first and second plates are movable relative to each other into different configurations, including an open configuration and a closed configuration;
  vii. each of the plates has, on its respective inner surface, a sample contact area for contacting a sample suspected of containing a analyte;
  viii. one or both plates comprises the spacers that are fixed on its inner surface, at least one of the spacers is inside the sample contact area, the spacers have a predetermined substantially uniform height that is equal to 100 um or less;
  ix. the plurality of particles has the capture agents immobilized on their surface, wherein the capture agents are capable of specifically binding and immobilizing the analyte; and
  x. the plurality of particles are (a) distributed on a sample contact area of the first, and (b) are temporarily or permanently fixed on the plate;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

NC1. The device of any prior embodiment, wherein the distribution of the plurality of particles on the plate is random.

NC2. The device of any prior embodiment, wherein the plurality of particles is fixed on the plate and has periodic distribution.

NC3. The device of any prior embodiment, wherein the spacer has a flat top.

NC4. The device of any prior embodiment, wherein the plurality of particles is temporarily fixed on the first plate, and in an open configuration the sample is deposited on the first plate before the two plates are brought into the closed configuration.

NC5. The device of any prior embodiment, wherein the thickness of the spacer is configured such that, in a closed configuration, for a certain concentration of the analytes in the sample, at least one area of the uniform thickness sample that contains one of the particle becomes optically distinguishable, when viewed outside of the sample layer, from its neighboring area that does not contain a particle.

NC6. The device of any prior embodiment, the device comprising two plates and spacers, wherein the pressing is by human hand.

NC7. The device of any prior embodiment, wherein the diameter of one or more of the plurality of particles is equal to the height of the spacers.

NC8. The device of any prior embodiment, wherein the spacer height is about 10 um.

NC9. The device of any prior embodiment, wherein the spacer height is about 5 um.

NC10. The device of any prior embodiment, wherein the spacer height is between about 0.1 um and about 15 um.

NC11. The device of any prior embodiment, wherein the spacer height is between about 0.1 um and about 3 um.

NC12. The device of any prior embodiment, wherein at least a portion of the inner surface of one plate or both plate is hydrophilic.

NC13. The device of any prior embodiment, wherein the inter spacer distance is periodic.

NC14. The device of any prior embodiment, wherein the sample is a deposition directly from a subject to the plate without using any transferring devices.

NC15. The device of any prior embodiment, wherein after the sample deformation at a closed configuration, the sample maintains the same final sample thickness, when some or all of the compressing forces are removed.

NC16. The device of any prior embodiment, wherein the spacers have pillar shape and nearly uniform cross-section.

NC17. The device of any prior embodiment, wherein the inter spacer distance (SD) is equal or less than about 120 um (micrometer).

NC18. The device of any prior embodiment, wherein the inter spacer distance (SD) is equal or less than about 100 um (micrometer).

NC19. The device of any prior embodiment, wherein the fourth power of the inter-spacer-distance (ISD) divided by the thickness (h) and the Young's modulus (E) of the flexible plate (ISD^4/(hE)) is 5×10^6 um^3/GPa or less.

NC20. The device of any prior embodiment, wherein the fourth power of the inter-spacer-distance (ISD) divided by the thickness (h) and the Young's modulus (E) of the flexible plate (ISD^4/(hE)) is 5×10^5 um3/GPa or less.

NC21. The device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

NC22. The device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

NC23. The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.

ND1. A method of performing a homogeneous assay, comprising the steps of:
  (a) obtaining a sample suspected of containing an analyte;
  (b) obtaining a device of any prior embodiment, wherein the capture agents are capable of specifically binding an binding site of the analyte;
  (c) having optical labels on at least a part of the sample contact areas of the device, wherein the optical labels are capable of binding to the analytes;
  (d) depositing the sample on one or both of the plates when the plates are in an open configuration, wherein in an open configuration;
  (e) after (d), bringing the two plates together and pressing the plates into a closed configuration, at least part of the sample is compressed by the two plates into a layer of highly uniform thickness, the uniform thickness of the layer is confined by the inner surfaces of the plates and is regulated by the plates and the spacers;
  (f) while the plates are in the closed configuration, analyzing the analyte in the layer of uniform thickness, wherein the analyzing comprises:
    i. measuring, from outside of the sample layer, the total light signal from (a) a particle area that is an area of the sample layer that contains one particle and from (b) a surrounding area that is the area of the sample layer which is around the particle area, wherein the surrounding area is 50 D within the edge of the particle, wherein the D is the diameter of the particle; and
    ii. measuring the total light signal from each of the particle area and the surrounding area of at least two different particle areas.

ND2. The method of any prior embodiment, wherein the particle area for the total light signal measurement has substantially the same area as the particle diameter.

ND3. The method of any prior embodiment, wherein the particle area for the total light signal measurement is smaller than the area defined by the particle diameter.

ND4. The method of any prior embodiment, wherein the analyzing the analyte in the uniform sample layer comprises averaging of the total light signal from each area.

ND5. The method of any prior embodiment, wherein the analyzing the analyte in the uniform sample layer comprises (i) taking a ratio of the total light signal of each particle area to that of its surrounding area, and (ii) averaging the ratio of all particle area and surround area pairs.

ND6. The method of any prior embodiment, wherein the time from the end of the sample deposition to the end of the plates being pressed into the closed configuration is less than 15 seconds.

ND7. The method of any prior embodiment, wherein the time from the end of the sample deposition to the end of the plates being pressed into the closed configuration is less than 5 seconds.

NE1. An apparatus for homogenous assaying an analyte in a sample, comprising:
  i. a device of any prior embodiment; and
  ii. one or more imagers that image at least a part of the sample contact area.

A device for rapid multiplexed homogeneous assay, comprising:
  a first plate, a second plate, and spacers, wherein:
    xi. the plates are movable relative to each other into different configurations, including an open configuration and a closed configuration;
    xii. each of the plates has, on its respective inner surface, a sample contact area for contacting a sample suspected of containing a first analyte and a second analyte;
    xiii. one or both of the plates comprise the spacers, at least one of the spacers is inside the sample contact area, and the spacers have a predetermined substantially uniform height;
    xiv. one or both of the plates comprise, on the respective inner surface, a plurality of first beads and second beads, wherein the first and second beads have first and second capture agents immobilized thereon, respectively; and
    xv. the first and second capture agents are capable of binding to and immobilizing the first and second analytes, respectively;
      wherein in the open configuration, the two plates are partially or entirely separated apart, the spacing between the plates is not regulated by the spacers, and the sample is deposited on one or both of the plates; and
      wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers, the analytes in the layer of uniform thickness are concentrated by the beads so that signal of the captured analytes on the beads is distinguishable from signal emanating from other area in the layer of uniform thickness.

NB1. A smartphone system for rapid multiplexed homogeneous assay, comprising:
  (a) a device of embodiment NA1;

A method of performing a rapid homogeneous assay, comprising the steps of:
  (a) obtaining a sample suspected of containing a first analyte of one species and a second analyte of a different species;
  (b) obtaining a first plate and a second plate, wherein:
    i. the plates are movable relative to each other into different configurations, including an open configuration and a closed configuration;
    ii. each of the plates has, on its respective inner surface, a sample contact area for contacting the sample;
    iii. one or both of the plates comprise spacers, at least one of the spacers is inside the sample contact area, and the spacers have a predetermined substantially uniform height;
    iv. one or both of the plates comprise, on the respective inner surface, a plurality of first beads and second beads, wherein the first and second beads have first and second capture agents immobilized thereon, respectively; and
    v. the first and second capture agents are capable of binding to and immobilizing the first and second analyte, respectively;
  (c) depositing the sample on one or both of the plates when the plates in the open configuration, wherein in the open configuration, the two plates are partially or entirely separated apart and the spacing between the plates is not regulated by the spacers;
  (d) after (c), bringing the two plates together and pressing the plates into the closed configuration, wherein in the closed configuration: at least part of the sample is compressed by the two plates into a layer of highly uniform thickness, the uniform thickness of the layer is confined by the inner surfaces of the two plates and is regulated by the spacers and the plates; and (e) while the plates are at the closed configuration, detecting and analyzing the analytes in the layer of uniform thickness.

NA2. The device, smartphone system, and method of any prior embodiments, wherein the first and second beads are different.

NA3. The device, smartphone system, and method of any prior embodiments, wherein the first and second beads are different in their sizes.

NA4. The device, smartphone system, and method of any prior embodiments, wherein the first and second beads are different in their optical properties selected from the group consisting of: photoluminescence, electroluminescence, and electrochemiluminescence, light absorption, reflection, transmission, diffraction, scattering, diffusion, surface Raman scattering, and any combination thereof.

NA5. The device, smartphone system, and method of any prior embodiments, wherein the first and second beads are different in their electric densities.

NA4. The device, smartphone system, and method of any prior embodiments, wherein the first and second beads are the same, and wherein the signals from the first and second analytes are different making plate with periodically arranged beads ND1. A method of making a plate with periodically arranged beads, comprising the steps of:
(1) having a plate that comprises a plurality of pits on its inner surface, wherein the pits are periodically arranged;
(2) depositing a liquid that contains a plurality of beads on the inner surface of the plate; and
(3) drying the plate, during which process the beads are re-distributed inside the pits due to at least the capillary force on the ridge of the pits.

Analyte Concentration Area:

AA1-1. A device for rapid homogeneous assay, comprising:
a first plate, a second plate, and spacers, wherein:
  i. the plates are movable relative to each other into different configurations, including an open configuration and a closed configuration;
  ii. each of the plates has, on its respective inner surface, a sample contact area for contacting a sample suspected of comprising an analyte;
  iii. one or both of the plates comprise the spacers, at least one of the spacers is inside the sample contact area, and the spacers have a predetermined substantially uniform height; and
  iv. one or both of the plates comprise, on the respective inner surface, one or a plurality of analyte concentration areas that have capture agent immobilized thereon, wherein the capture agent is capable of binding to and immobilizing the analyte;
    wherein in the open configuration, the two plates are partially or entirely separated apart, the spacing between the plates is not regulated by the spacers, and the sample is deposited on one or both of the plates; and
    wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers, the analyte in the layer of uniform thickness is concentrated in the analyte concentration area so that signal of captured analyte in the analyte concentration areas is distinguishable from signal emanating from non-analyte concentration area in the layer of uniform thickness.

Concentration Protrusion:

AA2. The device of any prior embodiment, wherein one or both of the plates comprise one or a plurality of protrusions extending from the respective inner surface, and wherein each protrusion has a height smaller than the spacers and comprises the analyte concentration area on at least one of its surfaces.

Beads:

AB1. A device for rapid homogeneous assay, comprising:
a first plate, a second plate, and spacers, wherein:
  i. the plates are movable relative to each other into different configurations, including an open configuration and a closed configuration;
  ii. each of the plates has, on its respective inner surface, a sample contact area for contacting a sample suspected of comprising an analyte;
  iii. one or both of the plates comprise the spacers, at least one of the spacers is inside the sample contact area, and the spacers have a predetermined substantially uniform height; and
  iv. one or both of the plates comprise, on the respective inner surface, a plurality of beads that have capture agent immobilized thereon, wherein the capture agent is capable of binding to and immobilizing the analyte;
    wherein in the open configuration, the two plates are partially or entirely separated apart, the spacing between the plates is not regulated by the spacers, and the sample is deposited on one or both of the plates; and
    wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers, the analyte in the layer of uniform thickness is concentrated by the beads so that signal of the captured analyte on the beads is distinguishable from signal emanating from other area in the layer of uniform thickness.

System:

C1. A system for rapid homogeneous assay, comprising:
  (a) a device of any prior embodiment; and
  (b) a detector that detects signals from the capture agent-bound analyte indicative of the presence and/or quantity of the analyte in the layer of uniform thickness Smartphone System:

D1. A smartphone system for rapid homogeneous assay, comprising:
  (a) a device of any prior embodiment;
  (b) a mobile communication device that comprises:
    i. one or a plurality of cameras for detecting and/or imaging the sample;
    ii. electronics, signal processors, hardware and software for receiving and/or processing the detected signal and/or the image of the sample and for remote communication; and
  (c) an adaptor that is configured to hold the closed device and engageable to mobile communication device;
    wherein when engaged with the mobile communication device, the adaptor is configured to facilitate the detection and/or imaging of the analyte in the sample at the closed configuration.

Method:

AE1. A method of performing a rapid homogeneous assay, comprising the steps of:
(a) obtaining a sample suspected of containing an analyte;
(b) obtaining a device of any prior embodiment;
(c) depositing the sample on one or both of the plates when the plates are in the open configuration;
(d) after (c), bringing the two plates together and pressing the plates into the closed configuration; and
(e) while the plates are at the closed configuration, detecting and analyzing the analyte in the layer of uniform thickness.

AE2. A method of analyzing the image for a rapid homogeneous assay, comprising the steps of:
(a) obtaining an image of the signal in any prior embodiment at the closed configuration, wherein the image is selected from the group consisting of bright field image, dark field image, fluorescence image, and phosphorescence image;
(b) analyzing the image, identifying beads in the image, and extracting information of beads size, signal intensity of beads, distance between beads, distribution of beads, and number of beads; and
(c) deducing analyte concentration by analyzing the extracted information from step (b) and calculating parameters of the beads.

E1. A method of performing a homogeneous assay, comprising the steps of:
(a) obtaining a sample suspected of containing an analyte;
(b) obtaining a first and second plates that are movable relative to each other into different configurations, including an open configuration and a closed configuration, wherein:
v. each of the plates has, on its respective inner surface, a sample contact area for contacting the sample,
vi. one or both of the plates comprise the spacers, and at least one of the spacers is inside the sample contact area;
vii. one or both of the plates comprise, on the respective inner surface, a plurality of beads that have capture agent immobilized thereon, wherein the capture agent is capable of binding to and immobilizing the analyte; and
viii. one or both of the plates comprise, on the respective inner surface, detection agent that is configured to, upon contacting the sample, be dissolved in the sample and bind to the analyte;
wherein the spacers have a predetermined substantially uniform height;
(c) depositing the sample on one or both of the plates when the plates are in an open configuration, wherein in the open configuration the two plates are partially or entirely separated apart and the spacing between the plates is not regulated by the spacers;
(d) after (c), bringing the two plates together and pressing the plates into a closed configuration, wherein in the closed configuration: at least part of the sample is compressed by the two plates into a layer of highly uniform thickness, the uniform thickness of the layer is confined by the inner surfaces of the two plates and is regulated by the spacers and the plates; and
(e) while the plates are at the closed configuration, detecting and analyzing the analyte in the layer of uniform thickness,
wherein the capture agent and the detection agent are configured to bind to the analyte at different locations thereof and to form a capture agent-analyte-detection agent sandwich that is immobilized to the bead; and
wherein the beads, the capture agent, and the detection agent are configured to render signal from the bead-associated capture agent-analyte-detection agent sandwich distinguishable from signal of free detection agent in the layer of uniform thickness.

Embodiments Defining Diffusion Parameters

AA1-2. A device for rapid homogenous assay, comprising: a first plate, a second plate, and spacers, wherein:
i. the plates are movable relative to each other into different configurations, including an open configuration and a closed configuration;
ii. each of the plates has, on its respective inner surface, a sample contact area for contacting a sample suspected of comprising an analyte;
iii. one or both of the plates comprise the spacers, at least one of the spacers is inside the sample contact area, and the spacers have a predetermined substantially uniform height of 200 um or less; and
iv. one or both of the plates comprise, on the respective inner surface, one or a plurality of analyte concentration areas that has capture agent immobilized thereon, wherein the capture agent is capable of binding the analyte;
wherein the spacers have a height that is equal to or less than 4 times of a diffusion parameter, wherein the diffusion parameter is square root of the intended assay time multiplying diffusion constant of the analyte in the sample and wherein the intended assay time is equal to or less than 240 seconds;
wherein the average distance between two neighboring analyte concentration areas is equal to or less than 4 times of the diffusion parameter;
wherein in the open configuration, the two plates are partially or entirely separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers and the analyte in the layer of uniform thickness is concentrated in the concentration area so that signal of captured analyte in the concentration areas is distinguishable from signal emanating from non-concentration area in the layer of uniform thickness.

AA2-2. The device of any prior embodiment, wherein one or both of the plates comprise one or a plurality of protrusions extending from the respective inner surface, and wherein each protrusion has a height smaller than the spacers and comprises the analyte concentration area on at least one of its surfaces.

AB1-2. A device for rapid homogeneous assay, comprising: a first plate, a second plate, and spacers, wherein:
i. the plates are movable relative to each other into different configurations, including an open configuration and a closed configuration;
ii. each of the plates has, on its respective inner surface, a sample contact area for contacting a sample suspected of comprising an analyte;
iii. one or both of the plates comprise the spacers, at least one of the spacers is inside the sample contact area, and the spacers have a predetermined substantially uniform height; and iv. one or both of the plates comprise, on the respective inner surface, a plurality of beads that have capture agent immobilized thereon, wherein the capture agent is capable of binding to and immobilizing the analyte;

wherein the spacers have a height that is equal to or less than 3 times of a diffusion parameter, wherein the diffusion parameter is square root of the intended assay time multiplying diffusion constant of the analyte in the sample and wherein the intended assay time is equal to or less than 240 seconds;

wherein the average distance between two neighboring beads is equal to or less than 2 times of the diffusion parameter;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers and the analyte in the layer of uniform thickness is concentrated in the concentration area so that signal of captured analyte in the concentration areas is distinguishable from signal emanating from non-concentration area in the layer of uniform thickness.

AE1-2. A method of performing a rapid homogeneous assay, comprising the steps of:

(a) obtaining a sample suspected of containing an analyte;

(b) obtaining a device of any prior embodiment;

(c) depositing the sample on one or both of the plates when the plates are in the open configuration;

(d) after (c), bringing the two plates together and pressing the plates into the closed configuration; and (e) after step (d), incubating the assay for a time equal to or longer than the intended assay time, detecting and analyzing the analyte in the layer of uniform thickness.

DP1. The device, kit, system, smartphone system, and method of any prior embodiments, wherein the intended assay time is in the range of 0.1-240 sec.

DP2-1. The device, kit, system, smartphone system, and method of any prior embodiments, wherein the intended assay time is in the range of 1-60 sec.

DP2-2. The device, kit, system, smartphone system, and method of any prior embodiments, wherein the intended assay time is equal to or less than 30 sec.

DP2-3. The device, kit, system, smartphone system, and method of any prior embodiments, wherein the intended assay time is equal to or less than 10 sec.

DP2-4. The device, kit, system, smartphone system, and method of any prior embodiments, wherein the intended assay time is equal to or less than 5 sec.

DP-5. The device, kit, system, smartphone system, and method of any prior embodiments, wherein the intended assay time is equal to or less than 1 sec.

DP3. The device, kit, system, smartphone system, and method of any prior embodiments, wherein the average distance between two neighboring analyte concentration areas or beads is in the range of 50 nm-200 um.

DP4-1. The device, kit, system, smartphone system, and method of any prior embodiments, wherein the average distance between two neighboring analyte concentration areas or beads is in the range of 500 nm-20 um.

DP4-2. The device, kit, system, smartphone system, and method of any prior embodiments, wherein the average distance between two neighboring analyte concentration areas or beads is in the range of 500 nm-10 um.

DP4-3. The device, kit, system, smartphone system, and method of any prior embodiments, wherein the average distance between two neighboring analyte concentration areas or beads is in the range of 500 nm-5 um.

DP5. The device, kit, system, smartphone system, and method of any prior embodiments, wherein the ratio of the spacers' height versus the diffusion parameter is in the range of 0.01-2.

DP6-1. The device, kit, system, smartphone system, and method of any prior embodiments, wherein the ratio of the spacers' height versus the diffusion parameter is in the range of 0.1-1.5.

DP6-2. The device, kit, system, smartphone system, and method of any prior embodiments, wherein the ratio of the spacers' height versus the diffusion parameter is in the range of 0.01-0.5.

DP6-3. The device, kit, system, smartphone system, and method of any prior embodiments, wherein the ratio of the spacers' height versus the diffusion parameter is in the range of 0.01-0.2.

DP6-4. The device, kit, system, smartphone system, and method of any prior embodiments, wherein the ratio of the spacers' height versus the diffusion parameter is in the range of 0.01-0.1.

DP7. The device, kit, system, smartphone system, and method of any prior embodiments, wherein the ratio of the average distance between two neighboring analyte concentration areas or beads versus the diffusion parameter is in the range of 0.01-5.

DP8-1. The device, kit, system, smartphone system, and method of any prior embodiments, wherein the ratio of the average distance between two neighboring analyte concentration areas or beads versus the diffusion parameter is in the range of 0.01-1.5.

DP8-2. The device, kit, system, smartphone system, and method of any prior embodiments, wherein the ratio of the average distance between two neighboring analyte concentration areas or beads versus the diffusion parameter is in the range of 0.01-1.

DP8-3. The device, kit, system, smartphone system, and method of any prior embodiments, wherein the ratio of the average distance between two neighboring analyte concentration areas or beads versus the diffusion parameter is in the range of 0.01-0.5.

DP8-4. The device, kit, system, smartphone system, and method of any prior embodiments, wherein the ratio of the average distance between two neighboring analyte concentration areas or beads versus the diffusion parameter is in the range of 0.01-0.2.

DP8-5. The device, kit, system, smartphone system, and method of any prior embodiments, wherein the ratio of the average distance between two neighboring analyte concentration areas or beads versus the diffusion parameter is in the range of 0.01-0.1.

DP9-1. The device, kit, system, smartphone system, and method of any prior embodiments, wherein the ratio of the average distance between two neighboring analyte concentration areas or beads versus the diffusion parameter is in the range of 0.01-0.5, and the ratio of the spacers' height versus the diffusion parameter is in the range of 0.01-0.2.

DP9-2. The device, kit, system, smartphone system, and method of any prior embodiments, wherein the ratio of the average distance between two neighboring analyte concentration areas or beads versus the diffusion parameter is in the range of 0.01-1, and the ratio of the spacers' height versus the diffusion parameter is in the range of 0.01-0.5.

DP9-3. The device, kit, system, smartphone system, and method of any prior embodiments, wherein the ratio of the average distance between two neighboring analyte concentration areas or beads versus the diffusion parameter is in the range of 0.01-2, and the ratio of the spacers' height versus the diffusion parameter is in the range of 0.01-1.

DP9-4. The device, kit, system, smartphone system, and method of any prior embodiments, wherein the ratio of the average distance between two neighboring analyte concentration areas or beads versus the diffusion parameter is in the range of 0.01-4, and the ratio of the spacers' height versus the diffusion parameter is in the range of 0.01-1.

DP10-1. The device, kit, system, smartphone system, and method of any prior embodiments, wherein the ratio of the average distance between two neighboring analyte concentration areas or beads versus the diffusion parameter is in the range of 0.01-0.5, the ratio of the spacers' height versus the diffusion parameter is in the range of 0.01-0.2, and the intended assay time is equal to or less than 120 sec.

DP10-2. The device, kit, system, smartphone system, and method of any prior embodiments, wherein the ratio of the average distance between two neighboring analyte concentration areas or beads versus the diffusion parameter is in the range of 0.01-1; the ratio of the spacers' height versus the diffusion parameter is in the range of 0.01-0.5, and the intended assay time is equal to or less than 60 sec.

DP10-3. The device, kit, system, smartphone system, and method of any prior embodiments, wherein the ratio of the average distance between two neighboring analyte concentration areas or beads versus the diffusion parameter is in the range of 0.01-2; the ratio of the spacers' height versus the diffusion parameter is in the range of 0.01-1; and the intended assay time is equal to or less than 30 sec.

DP10-4. The device, kit, system, smartphone system, and method of any prior embodiments, wherein the ratio of the average distance between two neighboring analyte concentration areas or beads versus the diffusion parameter is in the range of 0.01-4; the ratio of the spacers' height versus the diffusion parameter is in the range of 0.01-1; and the intended assay time is equal to or less than 30 sec.

More:

(Sandwich Assay)

AA1 The device, kit, system, smartphone system, and method of any prior embodiments, wherein the analyte is labeled by detection agent that selectively binds to the analyte and is associated with a label.

AA1.1 The device, kit, system, smartphone system, and method of any prior embodiments, wherein the detection agent is coated on the inner surface(s) of one or both of the plates, and is configured to, upon contacting the sample, be dissolved and diffuse in the sample.

AA1.2 The device, kit, system, smartphone system, and method of any prior embodiments, wherein the detection agent is pre-loaded into the sample before the sample is deposited on the plate(s).

AA1.3 The device, kit, system, smartphone system, and method of any prior embodiments, wherein the capture agent and the detection agent are configured to bind to the analyte at different locations thereof and form capture agent-analyte-detection agent sandwich.

(Competitive Assay)

AA2 The device, kit, system, smartphone system, and method of any prior embodiments, wherein the analyte competes with a detection agent to bind to the capture agent, and wherein the detection agent is labeled.

AA3 The device, kit, system, smartphone system, and method of any prior embodiments, wherein one or both of the plates comprise, on the respective inner surface, a signal amplification surface that amplify the signal in proximity to the amplification surface.

A2 The device, kit, system, smartphone system, and method of any prior embodiments, wherein the beads are the spacers that regulate the thickness of the layer at the closed configuration.

A2.1 The device, kit, system, smartphone system, and method of any prior embodiments, wherein the beads are micro- or nano-particles having an average diameter in the range of 1 nm to 200 um.

AA2.1 The device, kit, system, smartphone system, and method of any prior embodiments, wherein the analyte concentration areas have an average diameter in the range of 1 nm to 200 um.

AAA2.1 The device, kit, system, smartphone system, and method of any prior embodiments, wherein the concentrating protrusions have an average diameter in the range of 1 nm to 200 um.

A2.1.1 The device, kit, system, smartphone system, and method of any prior embodiments, wherein the beads have an average diameter in the range of 0.1 μm to 10 μm.

A2.1.2 The device, kit, system, smartphone system, and method of any prior embodiments, wherein the beads have an average diameter in the range of 1 nm to 500 nm.

A2.1.3 The device, kit, system, smartphone system, and method of any prior embodiments, wherein the beads have an average diameter in the range of to 0.5 μm to 30 μm.

A2.1.4 The device, kit, system, smartphone system, and method of any prior embodiments, wherein ratio between the spacing between the plates at the closed configuration and average diameter of the beads is in the range of 1-100.

AA2.1.4 The device, kit, system, smartphone system, and method of any prior embodiments, wherein ratio between the spacing between the plates at the closed configuration and height of the analyte concentration area is in the range of 1-100.

AAA2.1.4 The device, kit, system, smartphone system, and method of any prior embodiments, wherein ratio between the spacing between the plates at the closed configuration and height of the concentrating protrusion is in the range of 1-100.

A2.2 The device, kit, system, smartphone system, and method of any prior embodiments, wherein the beads have an area density of 1 to $10^6$ per $mm^2$.

AA2.2 The device, kit, system, smartphone system, and method of any prior embodiments, wherein the analyte concentration areas have an area density of 1 to $10^6$ per $mm^2$.

AAA2.2 The device, kit, system, smartphone system, and method of any prior embodiments, wherein the concentrating protrusions have an area density of 1 to $10^6$ per $mm^2$.

A2.2.1 The device, kit, system, smartphone system, and method of any prior embodiments, wherein the beads have an area density of 1 to 1000 per $mm^2$.

A2.3 The device, kit, system, smartphone system, and method of any prior embodiments, wherein the beads are configured to amplify the signal in proximity to the beads, and have a signal amplification factor in the range of 1 to 10000.

A2.4 The device, kit, system, smartphone system, and method of any prior embodiments, wherein the detection antibody is configured to have a concentration in the layer of uniform thickness that is 1 to 1000 times higher than analyte concentration in the sample.

A3 The device, kit, system, smartphone system, and method of any prior embodiments, wherein the beads and the detection agent are on the same plate.

A3.1 The device, kit, system, smartphone system, and method of any prior embodiments, wherein the beads and the detection agent are on different plates.

A4 The device, kit, system, smartphone system, and method of any prior embodiments, wherein the analyte is selected from the group consisting of: cells, viruses, proteins, peptides, DNAs, RNAs, oligonucleotides, and any combination thereof.

A4.1 The device, kit, system, smartphone system, and method of any prior embodiments, wherein the analyte is C Reactive Protein (CRP).

A5.1 The device, kit, system, smartphone system, and method of any prior embodiments, wherein the capture agent is selected from the group consisting of: protein, peptide, peptidomimetics, streptavidin, biotin, oligonucleotide, oligonucleotide mimetics, any other affinity ligand and any combination thereof.

A5.1.1 The device, kit, system, smartphone system, and method of any prior embodiments, wherein the capture agent is an antibody.

A5.1.2 The device, kit, system, smartphone system, and method of any prior embodiments, wherein the capture antibody is an anti-C Reactive Protein (CRP) antibody.

A5.1.3 The device, kit, system, smartphone system, and method of any prior embodiments, wherein the capture agent has a concentration that is sufficient to detect the presence and/or measure the amount of the analyte.

A5.1.4 The device, kit, system, smartphone system, and method of any prior embodiments, wherein the capture agent has a concentration that is sufficient to immobilize the analyte.

A5.2 The device, kit, system, smartphone system, and method of any prior embodiments, wherein the detection agent is selected from the group consisting of: protein, peptide, peptidomimetics, streptavidin, biotin, oligonucleotide, oligonucleotide mimetics, any other affinity ligand and any combination thereof.

A5.2.1 The device, kit, system, smartphone system, and method of any prior embodiments, wherein the detection agent is an antibody.

A5.2.2 The device, kit, system, smartphone system, and method of any prior embodiments, wherein the detection antibody is an anti-CRP antibody.

A6 The device, kit, system, smartphone system, and method of any prior embodiments, wherein the beads are made of a material selected from the group consisting of: polysteryne, polypropylene, polycarbonate, PMMG, PC, COC, COP, glass, resin, aluminum, gold or other metal or any other material whose surface can be modified to be associated with the capture agent.

A6.1 The device, kit, system, smartphone system, and method of any prior embodiments, wherein the beads are treated with a protein stabilizer.

A6.2 The device, kit, system, smartphone system, and method of any prior embodiments, wherein the capture agent are conjugated with the beads.

A6.3 The device, kit, system, smartphone system, and method of any prior embodiments, wherein the beads are prepared by:

(d) activating with N-Hydroxysuccinimide (NHS);
(e) blocking with a BSA solution; and
(f) incubating with a capture agent solution.

A7 The device, kit, system, smartphone system, and method of any prior embodiments, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

A7.1 The device, kit, system, smartphone system, and method of any prior embodiments, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

A7.2 The device, kit, system, smartphone system, and method of any prior embodiments, wherein the sample is an environmental gaseous sample from a source selected from the group consisting of: the air, underwater heat vents, industrial exhaust, vehicular exhaust, and any combination thereof.

A7.3 The device, kit, system, smartphone system, and method of any prior embodiments, wherein the sample is a foodstuff sample selected from the group consisting of: raw ingredients, cooked food, plant and animal sources of food, preprocessed food, and partially or fully processed food, and any combination thereof.

A8. The device, kit, system, smartphone system, and method of any prior embodiments, wherein the detection agent is a labeled agent.

A8.1 The device, kit, system, smartphone system, and method of any prior embodiments, wherein the detection agent is labeled with a fluorophore.

A8.1.1 The device, kit, system, smartphone system, and method of any prior embodiments, wherein the fluorophore is Cy5.

(Quencher)

A8.2 The device, kit, system, smartphone system, and method of any prior embodiments, wherein the beads are associated with a label, and wherein the detection agent is a quencher that is configured to quench signal of the beads-associated label when the detection agent is in proximity of the label.

A9. The device, kit, system, smartphone system, and method of any prior embodiments, wherein the detector detects the signal emanating from the analyte concentration areas or beads indicative of the presence and/or quantity of the analyte.

A9.1 The device, kit, system, smartphone system, and method of any prior embodiments, wherein the signal is:
  i. luminescence selected from photoluminescence, electroluminescence, and electrochemiluminescence;
  ii. light absorption, reflection, transmission, diffraction, scattering, or diffusion;
  iii. surface Raman scattering;
  iv. electrical impedance selected from resistance, capacitance, and inductance;
  v. magnetic relaxivity; or
  vi. any combination of i-v.

D2. The smartphone system of any prior embodiments, wherein the mobile communication device is configured to communicate test results to a medical professional, a medical facility or an insurance company.

D3. The smartphone system of any prior embodiments, wherein the mobile communication device is further configured to communicate information on the subject with the medical professional, medical facility or insurance company.

D4. The smartphone system of any prior embodiments, wherein the mobile communication device is configured to receive a prescription, diagnosis or a recommendation from a medical professional.

D5. The smartphone system of any prior embodiments, wherein the mobile communication device communicates with the remote location via a wifi or cellular network.

D6. The smartphone system of any prior embodiments, wherein the mobile communication device is a mobile phone.

E2 The method of any prior embodiments, wherein the sample contact sites are not washed before the imaging step (e).

E3 The method of any of embodiments 1-5, further comprising washing the sample contact area before the imaging step (e).

E4 The method of any prior embodiments, further comprising determining the presence of the analyte and/or measuring the amount of the analyte.

AE2.1 The method of embodiment AE2, wherein the calculated parameters comprise average signal intensity from all the beads that are analyzed.

AE2.2 The method of embodiment AE2, wherein the calculated parameters comprise highest signal intensity from all the beads that are analyzed.

AE2.3 The method of embodiment AE2, wherein the calculated parameters comprise signal intensity distribution from all the beads that are analyzed.

AE2.4 The method of embodiment AE2, wherein the calculated parameters comprise number of all the beads that are analyzed with signal intensity larger than a threshold;

AE2.5 The method of embodiment AE2, wherein the calculated parameters comprise average signal intensity from all the beads that are analyzed in a first area of the image.

AE2.6 The method of embodiment AE2, wherein the calculated parameters comprise highest signal intensity from all the beads that are analyzed in a first area of the image.

AE2.7 The method of embodiment AE2, wherein the calculated parameters comprise signal intensity distribution from all the beads that are analyzed in a first area of the image.

AE2.8 The method of embodiment AE2, wherein the calculated parameters comprise number of all the beads that are analyzed in a first area of the image with signal intensity larger than a threshold.

F1 The device that comprises two plates and spacers, wherein the pressing is by human hand.

F2 The device that comprises two plates and spacers, wherein at least a portion of the inner surface of one plate or both plate is hydrophilic.

F3 The device that comprises two plates and spacers, wherein the inter spacer distance is periodic.

F4 The device that comprises two plates and spacers, wherein the sample is a disposition directly from a subject to the plate without using any transferring devices.

F5 The device that comprises two plates and spacers, wherein after the sample deformation at a closed configuration, the sample maintains the same final sample thickness, when some or all of the compressing forces are removed.

F6 The device that comprises two plates and spacers, wherein the spacers have pillar shape and nearly uniform cross-section.

F7 The device that comprises two plates and spacers, wherein the inter space distance (SD) is equal or less than about 120 um (micrometer).

F8 The device that comprises two plates and spacers, wherein the inter space distance (SD) is equal or less than about 100 um (micrometer).

F9 The device that comprises two plates and spacers, wherein the fourth power of the inter-spacer-distance (ISD) divided by the thickness (h) and the Young's modulus (E) of the flexible plate (ISD$^4$/(hE)) is 5×10$^6$ um$^3$/GPa or less.

F10 The device that comprises two plates and spacers, wherein the fourth power of the inter-spacer-distance (ISD) divided by the thickness (h) and the Young's modulus (E) of the flexible plate (ISD$^4$/(hE)) is 5×10$^5$ um3/GPa or less.

F11 The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

F12 The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is 5×10$^6$ um$^3$/GPa or less.

F13 The device that comprises two plates and spacers, wherein the ratio of the inter-spacing distance of the spacers to the average width of the spacer is 2 or larger, and the filling factor of the spacers multiplied by the Young's modulus of the spacers is 2 MPa or larger.

F14 The device, kit, system, smartphone system, and method of any prior embodiments wherein the analytes is the analyte in 5 detection of proteins, peptides, nucleic acids, synthetic compounds, and inorganic compounds.

F15 The device, kit, system, smartphone system, and method of any prior embodiments wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

F16 The device, kit, system, smartphone system, and method of any prior embodiments wherein the spacers have a shape of pillars and a ratio of the width to the height of the pillar is equal or larger than one.

F17 The method of any prior claim, wherein the sample that is deposited on one or both of the plates has an unknown volume.

F18 The device, kit, system, smartphone system, and method of any prior embodiments wherein the spacers have a shape of pillar, and the pillar has substantially uniform cross-section.

F19 The device, kit, system, smartphone system, and method of any prior embodiments wherein the samples are for the detection, purification and quantification of chemical compounds or biomolecules that correlates with the stage of certain diseases.

F20 The device, kit, system, smartphone system, and method of any prior embodiments wherein the samples is related to infectious and parasitic disease, injuries, cardiovascular disease, cancer, mental disorders, neuropsychiatric disorders, pulmonary diseases, renal diseases, and other and organic diseases.

F21 The device, kit, system, smartphone system, and method of any prior embodiments wherein the samples are related to the detection, purification and quantification of microorganism.

F22 The device, kit, system, smartphone system, and method of any prior embodiments wherein the samples is related to virus, fungus and bacteria from environment, e.g., water, soil, or biological samples.

F23 The device, kit, system, smartphone system, and method of any prior embodiments wherein the samples is related to the detection, quantification of chemical compounds or biological samples that pose hazard to food safety or national security, e.g. toxic waste, anthrax.

F24 The device, kit, system, smartphone system, and method of any prior embodiments wherein the samples are related to quantification of vital parameters in medical or physiological monitor.

F25 The device, kit, system, smartphone system, and method of any prior embodiments wherein the samples are related to glucose, blood, oxygen level, total blood count.

F26 The device, kit, system, smartphone system, and method of any prior embodiments wherein the samples are related to the detection and quantification of specific DNA or RNA from biosamples.

F27 The device, kit, system, smartphone system, and method of any prior embodiments wherein the samples are related to the sequencing and comparing of genetic sequences in DNA in the chromosomes and mitochondria for genome analysis.

F28 The device, kit, system, smartphone system, and method of any prior embodiments wherein the samples are related to detect reaction products, e.g., during synthesis or purification of pharmaceuticals.

F29 The device, kit, system, smartphone system, and method of any prior embodiments wherein the samples are cells, tissues, bodily fluids, and stool.

F30 The device, kit, system, smartphone system, and method of any prior embodiments wherein the sample is the sample in the detection of proteins, peptides, nucleic acids, synthetic compounds, inorganic compounds.

F31 The device, kit, system, smartphone system, and method of any prior embodiments wherein the sample is the sample in the fields of human, veterinary, agriculture, foods, environments, and drug testing.

F32 The method or device of any prior claim, wherein the sample is a biological sample. is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, or bone.

Example-1

Homogeneous QMAX Immunoassay—for Human CRP (C-Reactive Protein)

Here we describe an experiment of homogeneous QMAX immunoassay for human CRP according to one embodiment of the present invention.

In this experiment, the device for the immunoassay comprises a first plate and a second plate. Conventional glass slide was used as the first plate and X-plate with 10 μm spacer as the second plate. Similar as shown in FIG. 13, microbeads were coated on the first plate, and the microbeads (Pierce, 10 μm in diameter) were NHS activated and conjugated to capture antibody (anti-CRP mouse monoclonal, Fitzgerald). A fluorescence microscope was used as the detector. The average distance between two neighboring beads is about 30 um to 50 um.

The experiment was conducted according to the following procedures:

1. Conjugation of capture antibody to beads. NHS activated beads (Pierce, 10 μm in diameter) were conjugated to anti-CRP mouse monoclonal capture antibody (Fitzgerald) according to manufacturer's protocol.
2. Blocking of beads. The antibody conjugated beads were blocked by 4% BSA in PBS at 4° C. over night and washed by PBST for 6 times prior to use.
3. Coating first plate. 1 μL of beads from Step 2 (beads concentration $10^7$-$10^8$/mL) were dropped on glass slide (Fisher Scientific) and air dried at room temperature.
4. Homogeneous QMAX assay. 1 μL of CRP analyte (Fitzgerald) at the concentration of 10 μg/mL and 1 μL of Cy5-labeled anti-CRP mouse monoclonal detection antibody (Fitzgerald) were dropped onto the area of coated beads on the glass slide. Different concentrations of Cy5 labeled anti-CRP detection antibody (A, 800 μg/mL; B, 100 μg/mL; C, 50 μg/mL; D, 25 μg/mL and E, 0 μg/mL) were tested separately. The mixture was immediately covered by X-plate (second plate) with 10 μm spacer and incubated for 30 seconds at room temperature.
5. Imaging. Without washing, the fluorescent images were taken by the fluorescence microscope (Ex 640 nm, Em 670-690 nm).

FIG. 19 shows exemplary pictures of the fluorescent signals with the QMAX device and the conjugated beads, as well as their corresponding bright-field images.

As shown in the figure, we found that, in this exemplary experiment, the concentration of the fluorophore-labeled detection antibody is critical for the homogeneous assay. When it is high enough to create a high fluorescence background (FIG. 19A, detection antibody concentration: 800 ug/mL), the true assay signal from the beads, although locally concentrated around the beads, is not distinguishable from the background in liquid.

In contrast, when the detection antibody is at relatively low concentrations (FIGS. 19B-D, 100 ug/mL, 50 ug/mL, 25 ug/mL, respectively), the background created by the free (unbound) fluorophore labeled antibody in liquid is low enough so that the assay signals on the beads are distinguishable. It is worth noting that when the concentration of detection antibody is too low, there will be not enough detection antibody to be captured onto the beads, which may result in poor contrast to the background.

Example-2

Beads-Enhanced Speedy Test (BEST) Structure Examples

1. Exemplary Embodiments of Beads-Enhanced Speedy Test (BEST)—Beads Based:

One exemplary device comprises a first plate, a second plate, an array of spacers on the second plate, beads and concentration areas.

First plate: 24 mm×32 mm size, 1 mm thick plastic (as acrylic or polystyrene) or glass Second plate: 22 mm×25 mm size, 175 um thick plastic (as acrylic or polystyrene) with an array of pillar spacers on one side. The pillar spacers are 30×40 um in lateral size, and 10 um in height, and the inter-spacer distance is 80 um for the array.

Beads: 10 um in diameter plastic beads (as acrylic or polystyrene) with an area concentration of 100/mm2 to 1000/mm2, which are uniformly pre-dried on the second plate.

Concentration areas: on the surface of all the beads

2. Exemplary Embodiments of Beads-Enhanced Speedy Test (BEST)—Beads Based:

Another exemplary device comprises a first plate, a second plate, spacer array on the second plate, beads and concentration areas.

First plate: 24 mm×32 mm size, 1 mm thick plastic (as acrylic or polystyrene) or glass Second plate: 22 mm×25 mm size, 50 um thick plastic (as acrylic or polystyrene) with an array of pillar spacers on one side. The pillar spacers are 20×20 um in lateral size, and 20 um in height, and the inter-spacer distance is 150 um for the array.

Beads: 20 um in diameter beads with metal surface (as gold or silver) with an area concentration of 100/mm2 to 1000/mm2, which are uniformly pre-dried on the second plate.

Concentration area: on the surface of all the beads

3. Exemplary Embodiments of Beads-Enhanced Speedy Test (BEST)—Beads Based:

Another exemplary device comprises a first plate, a second plate, a pit array on the first plate, an array of spacers on the second plate, beads and concentration areas.

First plate: 24 mm×32 mm size, 1 mm thick plastic (as acrylic or polystyrene) or glass with pit array on one side. The pits are 12 um×12 um in lateral size, and 6 um in depth, and the inter-pit distance is 50 um.

Second plate: 22 mm×25 mm size, 175 um thick plastic (as acrylic or polystyrene) with an array of pillar spacers on one side. The pillar spacers are 20×20 um in lateral size, and 10 um in height, and the inter-spacer distance is 100 um.

Beads: 10 um in diameter beads with or without metal surface (gold or silver) with an area concentration of 100/mm2 to 1000/mm2, which are uniformly pre-dried on the first plate and mostly inside the pits.

Concentration area: on the surface of all the beads

4. Exemplary Embodiments of Beads-Enhanced Speedy Test (BEST)—Protrusions Based:

Another exemplary device comprises a first plate, a second plate, an array of first type of pillars (spacers) and an array of second type of pillars (protrusions) on the first plate, and concentration areas.

First plate: 24 mm×32 mm size, 1 mm thick plastic (as acrylic or polystyrene) or glass with the two pillar arrays on one side. The first type of pillars are 20×20 um in lateral size, and 10 um in height, and the inter-pillar distance is 150 um. The second type of pillars are 10 um in lateral diameter, and 8 um in height, and the inter-pillar distance is 50 um. The two pillar arrays are intermingled with one another.

Second plate: 22 mm×25 mm size, 150 um thick plastic (as acrylic or polystyrene) with flat surface.

Concentration area: on the top surface of the protrusions. Or on the side surfaces of the protrusions. Or on all the surfaces of the protrusions.

5. Exemplary Embodiments of Beads-Enhanced Speedy Test (BEST)—Protrusions Based:

Another exemplary device comprises a first plate, a second plate, an array of first type of pillars (spacers) and an array of second type of pillars (protrusions) on the first plate, and concentration areas.

First plate: 24 mm×32 mm size, 1 mm thick plastic (as acrylic or polystyrene) or glass with the two pillar arrays on one side. The first type pillars are 30×30 um in lateral size, and 15 um in height, and the inter-pillar distance is 120 um. The second type pillars are 15 um in lateral diameter, and 10 um in height, and the inter-pillar distance is 60 um. The two pillar arrays are intermingled with one another The second type pillars are coated with gold on all the surfaces.

Second plate: 22 mm×25 mm size, 100 um thick plastic (as acrylic or polystyrene) with flat surface.

Concentration area: on the top surface of the protrusions. Or on the side surfaces of the protrusions. Or on all the surfaces of the protrusions.

6. Exemplary Embodiments of Beads-Enhanced Speedy Test (BEST)—Protrusions Based:

Another exemplary device comprises a first plate, a second plate, an array of first type of pillars (protrusions) on the first plate, an array of second type of pillars (spacers) on the second plate, and concentration areas.

First plate: 24 mm×32 mm size, 1 mm thick plastic (as acrylic or polystyrene) or glass with the protrusion pillar array on one side. The protrusion pillars are 10 um pillar in lateral diameter, and 5 um in height, and the inter-pillar distance is 50 um.

Second plate: 22 mm×25 mm size, 50 um thick plastic (as acrylic or polystyrene) with flat surface. The spacer pillars are 20×20 um in lateral size, and 10 um in height, and the inter-pillar distance is 150 um.

Concentration area: on the top surface of the protrusions. Or on the side surfaces of the protrusions. Or on all the surfaces of the protrusions.

In all the above exemplary devices of this section, the side wall(s) of the protrusion pillars has/have a slope of 90°, 80°, 70°, 60°, 50°, 40°, 30°, 20°, or in a range between any of these two values.

CROF Flow and QMAX-CARD)

A) QMAX Card

Details of the QMAX card are described in detail in a variety of publications including International Application No. PCT/US2016/046437 (Essenlix Docket No. ESSN-028WO), which is hereby incorporated by reference herein for all purposes.

I. Plates

In present invention, generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) are used for the plate to achieve certain objectives.

In certain embodiments, the two plates have the same or different parameters for each of the following parameters: plate material, plate thickness, plate shape, plate area, plate flexibility, plate surface property, and plate optical transparency.

(i) Plate Materials. The plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1: The inorganic materials for the plates include, not limited to, glass, quartz, oxides, silicon-dioxide, silicon-nitride, hafnium oxide (HfO), aluminum oxide (AlO), semi-conductors: (silicon, GaAs, GaN, etc.), metals (e.g. gold, silver, coper, aluminum, Ti, Ni, etc.), ceramics, or any combinations of thereof.

Mat-2: The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In certain embodiments, the plates are each independently made of at least one of glass, plastic, ceramic, and metal. In certain embodiments, each plate independently includes at least one of glass, plastic, ceramic, and metal.

In certain embodiments, one plate is different from the other plate in lateral area, thickness, shape, materials, or surface treatment. In certain embodiments, one plate is the same as the other plate in lateral area, thickness, shape, materials, or surface treatment.

The materials for the plates are rigid, flexible or any flexibility between the two. The rigid (e.g., stiff) or flexibility is relative to a give pressing forces used in bringing the plates into the closed configuration.

In certain embodiments, a selection of rigid or flexible plate are determined from the requirements of controlling a uniformity of the sample thickness at the closed configuration.

In certain embodiments, at least one of the two plates are transparent (to a light). In certain embodiments at least a part or several parts of one plate or both plates are transparent.

In certain embodiments, the plates are non-transparent.

(ii) Plate Thickness. In certain embodiments, the average thicknesses for at least one of the pates are 2 nm or less, 10 nm or less, 100 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, or a range between any two of the values.

In certain embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In certain embodiments, the thickness of a plate is not uniform across the plate. Using a different plate thickness at different location can be used to control the plate bending, folding, sample thickness regulation, and others.

(iii) Plate Shape and Area. Generally, the plates can have any shapes, as long as the shape allows a compress open flow of the sample and the regulation of the sample thickness. However, in certain embodiments, a particular shape can be advantageous. The shape of the plate can be round, elliptical, rectangles, triangles, polygons, ring-shaped, or any superpositions of these shapes.

In certain embodiments, the two plates can have the same size or shape, or different. The area of the plates depend on the application. The area of the plate is at most 1 mm2 (millimeter square), at most 10 mm2, at most 100 mm2, at most 1 cm2 (centimeter square), at most 5 cm2, at most 10 cm2, at most 100 cm2, at most 500 cm2, at most 1000 cm2, at most 5000 cm2, at most 10,000 cm2, or over 10,000 cm2, or any arrange between any of the two values. The shape of the plate can be rectangle, square, round, or others.

In certain embodiments, at least one of the plates is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or a range between any two of the values. The length can be as long it needed. The belt can be rolled into a roll.

(iv) Plate Surface Flatness. In many embodiments, an inner surface of the plates are flat or significantly flat, planar. In certain embodiments, the two inner surfaces are, at the closed configuration, parallel with each other. Flat inner surfaces facilitates a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

A flatness of the plate surface is relative to the final sample thickness (the final thickness is the thickness at the closed configuration), and is often characterized by the term of "relative surface flatness" is the ratio of the plate surface flatness variation to the final sample thickness.

In certain embodiments, the relative surface is less than 0.01%, 0.1%, less than 0.5%, less than 1%, less than 2%, less than 5%, less than 10%, less than 20%, less than 30%, less than 50%, less than 70%, less than 80%, less than 100%, or a range between any two of these values.

(v) Plate Surface Parallelness. In certain embodiments, the two surfaces of the plate is significantly parallel with each other. In certain embodiments, the two surfaces of the plate is not parallel with each other.

(vi) Plate Flexibility. In certain embodiments, a plate is flexible under the compressing of a CROF process. In certain embodiments, both plates are flexible under the compressing of a CROF process. In certain embodiments, a plate is rigid and another plate is flexible under the compressing of a CROF process. In certain embodiments, both plates are rigid. In certain embodiments, both plate are flexible but have different flexibility.

(vii) Plate Optical Transparency. In certain embodiments, a plate is optical transparent. In certain embodiments, both plates are optical transparent. In certain embodiments, a plate is optical transparent and another plate is opaque. In certain embodiments, both plates are opaque. In certain embodiments, both plate are optical transparent but have different optical transparency. The optical transparency of a plate can refer to a part or the entire area of the plate.

(viii) Surface Wetting Properties. In certain embodiments, a plate has an inner surface that wets (e.g., contact angle is less 90 degree) the sample, the transfer liquid, or both. In certain embodiments, both plates have an inner surface that wets the sample, the transfer liquid, or both; either with the same or different wettability. In certain embodiments, a plate has an inner surface that wets the sample, the transfer liquid, or both; and another plate has an inner surface that does not wet (e.g., the contact angle equal to or larger than 90 degree). The wetting of a plate inner surface can refer to a part or the entire area of the plate.

In certain embodiments, the inner surface of the plate has other nano or microstructures to control a lateral flow of a sample during a CROF. The nano or microstructures include, but not limited to, channels, pumps, and others. Nano and microstructures are also used to control the wetting properties of an inner surface.

II. Spacers (i) Spacers' Function. In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

(ii) Spacer Architectures and Shapes. To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Certain embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (e.g., the sample flows around and pass the spacer. For example, a post as the spacer.), and the enclosed spacer is the spacer that stop the sample flow (e.g., the sample cannot flow beyond the spacer. For example, a ring shape spacer and the sample is inside the ring.). Both types of spacers use their height to regular the final sample thickness at a closed configuration.

In certain embodiments, the spacers are open-spacers only. In certain embodiments, the spacers are enclosed-spacers only. In certain embodiments, the spacers are a combination of open-spacers and enclosed-spacers.

The term "pillar spacer" means that the spacer has a pillar shape and the pillar shape can refer to an object that has height and a lateral shape that allow a sample to flow around it during a compressed open flow.

In certain embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In certain embodiments, the spacers can be and/or can include posts, columns, beads, spheres, and/or other suitable geometries. The lateral shape and dimension (e.g., transverse to the respective plate surface) of the spacers can be anything, except, in certain embodiments, the following restrictions: (i) the spacer geometry will not cause a significant error in measuring the sample thickness and volume; or (ii) the spacer geometry would not prevent the out-flowing of the sample between the plates (e.g., it is not in enclosed form). But in certain embodiments, they require some spacers to be closed spacers to restrict the sample flow.

In certain embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In certain embodiments, the spacers are pillars of various lateral shapes, sidewalls, and pillar-height to pillar lateral area ratio. In a preferred embodiment, the spacers have shapes of pillars for allowing open flow.

(iii) Spacers' Materials. In the present invention, the spacers are generally made of any material that is capable of being used to regulate, together with the two plates, the thickness of a relevant volume of the sample. In certain embodiments, the materials for the spacers are different from that for the plates. In certain embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

(iv) Spacers' Mechanical Strength and Flexibility. In certain embodiments, the mechanical strength of the spacers are strong enough, so that during the compression and at the closed configuration of the plates, the height of the spacers is the same or significantly same as that when the plates are in an open configuration. In certain embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

(v) Spacers Inside Sample. To achieve desired sample thickness reduction and control, particularly to achieve a good sample thickness uniformity, in certain embodiments, the spacers are placed inside the sample, or the relevant volume of the sample. In certain embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" can be determined by a sample thickness uniformity or a required sample flow property during a CROF.

(vi) Spacer Height. In certain embodiments, all spacers have the same pre-determined height. In certain embodiments, spacers have different pre-determined height. In certain embodiments, spacers can be divided into groups or regions, wherein each group or region has its own spacer height. And in certain embodiments, the predetermined height of the spacers is an average height of the spacers. In certain embodiments, the spacers have approximately the same height. In certain embodiments, a percentage of number of the spacers have the same height.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1000 nm in a separate preferred embodiment, 1 um (e.g., 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In certain embodiments, the spacer height and/or sample thickness (i) equal to or slightly larger than the minimum dimension of an analyte, or (ii) equal to or slightly larger than the maximum dimension of an analyte. The "slightly larger" means that it is about 1% to 5% larger and any number between the two values.

In certain embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. (Too many overlaps between the RBC's can cause serious errors in counting).

In the present invention, in certain embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (e.g., less surface concentration).

(vii) Spacer Lateral Dimension. For an open-spacer, the lateral dimensions can be characterized by its lateral dimension (sometime being called width) in the x and y—two orthogonal directions. The lateral dimension of a spacer in each direction is the same or different. In certain embodiments, the lateral dimension for each direction (x or y) is . . . .

In certain embodiments, the ratio of the lateral dimensions of x to y direction is 1, 1.5, 2, 5, 10, 100, 500, 1000, 10,000, or a range between any two of the value. In certain embodiments, a different ratio is used to regulate the sample flow direction; the larger the ratio, the flow is along one direction (larger size direction).

In certain embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In certain embodiments, all spacers have the same shape and dimensions. In certain embodiments, each of the spacers have different lateral dimensions.

For enclosed-spacers, in certain embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

(viii) Aspect Ratio of Height to the Average Lateral Dimension of Pillar Spacer. In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

(ix) Spacer Height Precisions. The spacer height should be controlled precisely. The relative precision of the spacer (e.g., the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

(x) Inter-Spacer Distance. The spacers can be a single spacer or a plurality of spacers on the plate or in a relevant area of the sample. In certain embodiments, the spacers on the plates are configured and/or arranged in an array form, and the array is a periodic, non-periodic array or periodic in some locations of the plate while non-periodic in other locations.

In certain embodiments, the periodic array of the spacers has a lattice of square, rectangle, triangle, hexagon, polygon, or any combinations of thereof, where a combination means that different locations of a plate has different spacer lattices.

In certain embodiments, the inter-spacer distance of a spacer array is periodic (e.g., uniform inter-spacer distance) in at least one direction of the array. In certain embodiments, the inter-spacer distance is configured to improve the uniformity between the plate spacing at a closed configuration.

The distance between neighboring spacers (e.g., the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a 10 mm or less, 20 mm or less, 30 mm or less, 50 mm or less, 70 mm or less, 100 mm or less, or any range between the values.

The distance between neighboring spacers (e.g., the inter-spacer distance) is selected so that for a given properties of the plates and a sample, at the closed-configuration of the plates, the sample thickness variation between two neighboring spacers is, in certain embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

Specify the accuracy of the inter spacer distance.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (e.g., 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

(xi) Spacer Density. The spacers are arranged on the respective plates at a surface density of greater than one per $um^2$, greater than one per 10 $um^2$, greater than one per 100 um2, greater than one per 500 $um^2$, greater than one per 1000 $um^2$, greater than one per 5000 um2, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

(3) the spacers are configured to not take significant surface area (volume) in a given sample area (volume);

(xii) Ratio of Spacer Volume to Sample Volume. In many embodiments, the ratio of the spacer volume (e.g., the volume of the spacer) to sample volume (e.g., the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (e.g., flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

(xiii) Spacers Fixed to Plates. The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

In certain embodiments of the present disclosure, spacers are fixed on one of the plates before bring the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (e.g., the spacer moves away from its original position on the plate surface).

In certain embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In certain embodiments, a spacer is fixed to a plate monolithically.

In certain embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (e.g., embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In certain embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In certain embodiments, at least a distance between two spacers is predetermined ("predetermined inter-spacer distance" means that the distance is known when a user uses the plates.).

In certain embodiments of all methods and devices described herein, there are additional spacers besides to the fixed spacers.

(xiv) Specific Sample Thickness. In present invention, it was observed that a larger plate holding force (e.g., the force that holds the two plates together) can be achieved by using a smaller plate spacing (for a given sample area), or a larger sample area (for a given plate-spacing), or both.

In certain embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

The spacers can be fabricated on a plate in a variety of ways, using lithography, etching, embossing (nanoimprint), depositions, lift-off, fusing, or a combination of thereof. In certain embodiments, the spacers are directly embossed or imprinted on the plates. In certain embodiments, the spacers imprinted into a material (e.g. plastics) that is deposited on the plates. In certain embodiments, the spacers are made by directly embossing a surface of a CROF plate. The nanoimprinting can be done by roll to roll technology using a roller imprinter, or roll to a planar nanoimprint. Such process has a great economic advantage and hence lowering the cost.

In certain embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom expose the plate surface and then a spacer material is deposited into the hole and afterwards the removable material is removed, leaving only the spacers on the plate surface. In certain embodiments, the spacers deposited on the plate are fused with the plate. In certain embodiments, the spacer and the plates are fabricated in a single process. The single process includes imprinting (e.g., embossing, molding) or synthesis.

In certain embodiments, at least two of the spacers are fixed to the respective plate by different fabrication methods, and optionally wherein the different fabrication methods include at least one of being deposition, bonded, fuse, imprinted, and etched.

In certain embodiments, one or more of the spacers are fixed to the respective plate(s) is by a fabrication method of being bonded, being fused, being imprinted, or being etched, or any combination of thereof.

In certain embodiments, the fabrication methods for forming such monolithic spacers on the plate include a method of being bonded, being fused, being imprinted, or being etched, or any combination of thereof.

B) Adaptor

Details of the Adaptor are described in detail in a variety of publications including International Application No. PCT/US2018/017504 (Essenlix Docket No. ESXPCT-18F04), which is hereby incorporated by reference herein for all purposes.

The present invention that is described herein address this problem by providing a system comprising an optical adaptor and a smartphone. The optical adaptor device fits over a smartphone converting it into a microscope which can take both fluorescent and bright-field images of a sample. This system can be operated conveniently and reliably by a common person at any location. The optical adaptor takes advantage of the existing resources of the smartphone, including camera, light source, processor and display screen, which provides a low-cost solution let the user to do bright-field and fluorescent microscopy.

In this invention, the optical adaptor device comprises a holder frame fitting over the upper part of the smartphone and an optical box attached to the holder having sample receptacle slot and illumination optics. In some references (U.S. Pat. No. 2016/029091 and U.S. Pat. No. 2011/0292198), their optical adaptor design is a whole piece including both the clip-on mechanics parts to fit over the smartphone and the functional optics elements. This design has the problem that they need to redesign the whole-piece optical adaptor for each specific model of smartphone. But in this present invention, the optical adaptor is separated into a holder frame only for fitting a smartphone and a universal optical box containing all the functional parts. For the smartphones with different dimensions, as long as the relative positions of the camera and the light source are the same, only the holder frame need to be redesigned, which will save a lot of cost of design and manufacture.

The optical box of the optical adaptor comprises: a receptacle slot which receives and position the sample in a sample slide in the field of view and focal range of the smartphone camera; a bright-field illumination optics for capturing bright-field microscopy images of a sample; a fluorescent illumination optics for capturing fluorescent microscopy images of a sample; a lever to switch between bright-field illumination optics and fluorescent illumination optics by sliding inward and outward in the optical box.

The receptacle slot has a rubber door attached to it, which can fully cover the slot to prevent the ambient light getting into the optical box to be collected by the camera. In U.S. Pat. 2016/0290916, the sample slot is always exposed to the ambient light which won't cause too much problem because it only does bright-field microscopy. But the present invention can take the advantage of this rubber door when doing fluorescent microscopy because the ambient light would bring a lot of noise to the image sensor of the camera.

To capture good fluorescent microscopy image, it is desirable that nearly no excitation light goes into the camera and only the fluorescent emitted by the sample is collected by the camera. For all common smartphones, however, the optical filter putting in front of the camera cannot block the undesired wavelength range of the light emitted from the light source of a smartphone very well due to the large divergence angle of the beams emitted by the light source and the optical filter not working well for un-collimated beams. Collimation optics can be designed to collimated the beam emitted by the smartphone light source to address this issue, but this approach increase the size and cost of the adaptor. Instead, in this present invention, fluorescent illumination optics enables the excitation light to illuminate the sample partially from the waveguide inside the sample slide and partially from the backside of the sample side in large oblique incidence angle so that excitation light will nearly not be collected by the camera to reduce the noise signal getting into the camera.

The bright-field illumination optics in the adaptor receive and turn the beam emitted by the light source so as to back-illuminated the sample in normal incidence angle.

Typically, the optical box also comprises a lens mounted in it aligned with the camera of the smartphone, which magnifies the images captured by the camera. The images captured by the camera can be further processed by the processor of smartphone and outputs the analysis result on the screen of smartphone.

To achieve both bright-field illumination and fluorescent illumination optics in a same optical adaptor, in this present invention, a slidable lever is used. The optical elements of the fluorescent illumination optics are mounted on the lever and when the lever fully slides into the optical box, the fluorescent illumination optics elements block the optical path of bright-field illumination optics and switch the illumination optics to fluorescent illumination optics. And when the lever slides out, the fluorescent illumination optics elements mounted on the lever move out of the optical path and switch the illumination optics to bright-field illumination optics. This lever design makes the optical adaptor work in both bright-field and fluorescent illumination modes without the need for designing two different single-mode optical boxes.

The lever comprises two planes at different planes at different heights.

In certain embodiments, two planes can be joined together with a vertical bar and move together in or out of the optical box. In certain embodiments, two planes can be separated and each plane can move individually in or out of the optical box.

The upper lever plane comprises at least one optical element which can be, but not limited to be an optical filter. The upper lever plane moves under the light source and the preferred distance between the upper lever plane and the light source is in the range of 0 to 5 mm.

Part of the bottom lever plane is not parallel to the image plane. And the surface of the non-parallel part of the bottom lever plane has mirror finish with high reflectivity larger than 95%.

The non-parallel part of the bottom lever plane moves under the light source and deflects the light emitted from the light source to back-illuminate the sample area right under the camera. The preferred tilt angle of the non-parallel part of the bottom lever plane is in the range of 45 degree to 65 degree and the tilt angle is defined as the angle between the non-parallel bottom plane and the vertical plane.

Part of the bottom lever plane is parallel to the image plane and is located under and 1 mm to 10 mm away from the sample. The surface of the parallel part of the bottom lever plane is highly light absorptive with light absorption larger than 95%. This absorptive surface is to eliminate the reflective light back-illuminating on the sample in small incidence angle.

To slide in and out to switch the illumination optics using the lever, a stopper design comprising a ball plunger and a groove on the lever is used in order to stop the lever at a pre-defined position when being pulled outward from the adaptor. This allow the user to use arbitrary force the pull the lever but make the lever to stop at a fixed position where the optical adaptor's working mode is switched to bright-filed illumination.

A sample slider is mounted inside the receptacle slot to receive the QMAX device and position the sample in the QMAX device in the field of view and focal range of the smartphone camera.

The sample slider comprises a fixed track frame and a moveable arm:

The frame track is fixedly mounted in the receptacle slot of the optical box. And the track frame has a sliding track slot that fits the width and thickness of the QMAX device so that the QMAX device can slide along the track. The width and height of the track slot is carefully configured to make the QMAX device shift less than 0.5 mm in the direction perpendicular to the sliding direction in the sliding plane and shift less than less than 0.2 mm along the thickness direction of the QMAX device.

The frame track has an opened window under the field of view of the camera of smartphone to allow the light back-illuminate the sample.

A moveable arm is pre-built in the sliding track slot of the track frame and moves together with the QMAX device to guide the movement of QMAX device in the track frame.

The moveable arm equipped with a stopping mechanism with two pre-defined stop positions. For one position, the arm will make the QMAX device stop at the position where a fixed sample area on the QMAX device is right under the camera of smartphone. For the other position, the arm will make the QMAX device stop at the position where the sample area on QMAX device is out of the field of view of the smartphone and the QMAX device can be easily taken out of the track slot.

The moveable arm switches between the two stop positions by a pressing the QMAX device and the moveable arm together to the end of the track slot and then releasing.

C) The moveable arm can indicate if the QMAX device is inserted in correct direction. The shape of one corner of the QMAX device is configured to be different from the other three right angle corners. And the shape of the moveable arm matches the shape of the corner with the special shape so that only in correct direction can QMAX device slide to correct position in the track slot/Detection System Details of the Smartphone/Detection System are described in detail in a variety of publications including International Application (IA) No. PCT/US2016/046437 filed on Aug. 10, 2016, IA No. PCT/US2016/051775 filed Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, each of which are hereby incorporated herein by reference in their entirety for all purposes.

The devices/apparatus, systems, and methods herein disclosed can include or use Q-cards for sample detection, analysis, and quantification. In certain embodiments, the Q-card is used together with an adaptor that can connect the Q-card with a smartphone detection system. In certain embodiments, the smartphone comprises a camera and/or an illumination source. In certain embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In certain embodiments, the smartphone comprises a camera, but the camera is not used for image capturing.

In certain embodiments, the smartphone comprises a light source such as but not limited to LED (light emitting diode). In certain embodiments, the light source is used to provide illumination to the sample when the sample is positioned in the field of view of the camera (e.g. by an adaptor). In certain embodiments, the light from the light source is enhanced, magnified, altered, and/or optimized by optical components of the adaptor.

In certain embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In certain embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In certain embodiments, the smartphone is an iPhone™, an Android™ phone, or a Windows™ phone.

D) Method of Manufacture

Details of the Method of Manufacture are described in detail in a variety of publications including International Application No. PCT/US2018/057873 filed Oct. 26, 2018, which is hereby incorporated by reference herein for all purposes.

Devices of the disclosure can be fabricated using techniques well known in the art. The choice of fabrication technique will depend on the material used for the device and the size of the spacer array and/or the size of the spacers. Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) is used to fabricate silicon-based devices with small gaps, small spacers and large aspect ratios (ratio of spacer height to lateral dimension). Thermoforming (embossing, injection molding) of plastic devices can also be used, e.g., when the smallest lateral feature is >20 microns and the aspect ratio of these features is ≤10.

Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser nicromachining can be adopted for plastic materials with high photon absorption efficiency. This technique is suitable for lower throughput fabrication because of the serial nature of the process. For mass-produced plastic devices, thermoplastic injection molding, and compression molding can be suitable. Conventional thermoplastic injection molding used for mass-fabrication of compact discs (which preserves fidelity of features in sub-microns) can also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding can be chosen as the method of manufacture. Compression molding (also called hot embossing or relief imprinting) has the advantages of being compatible with high molecular weight polymers, which are excellent for small structures and can replicate high aspect ratio structures but has longer cycle times. Injection molding works well for low aspect ratio structures and is most suitable for low molecular weight polymers.

A device can be fabricated in one or more pieces that are then assembled. Layers of a device can be bonded together by clamps, adhesives, heat, anodic bonding, or reactions between surface groups (e.g., wafer bonding). Alternatively, a device with channels or gaps in more than one plane can be fabricated as a single piece, e.g., using stereolithography or other three-dimensional fabrication techniques.

To reduce non-specific adsorption of cells or compounds released by lysed cells onto the surfaces of the device, one or more surfaces of the device can be chemically modified to be non-adherent or repulsive. The surfaces can be coated with a thin film coating (e.g., a monolayer) of commercial non-stick reagents, such as those used to form hydrogels. Additional examples chemical species that can be used to modify the surfaces of the device include oligoethylene glycols, fluorinated polymers, organosilanes, thiols, polyethylene glycol, hyaluronic acid, bovine serum albumin, poly-vinyl alcohol, mucin, poly-HEMA, methacrylated PEG, and agarose. Charged polymers can also be employed to repel oppositely charged species. The type of chemical species used for repulsion and the method of attachment to the surfaces of the device will depend on the nature of the species being repelled and the nature of the surfaces and the species being attached. Such surface modification techniques are well known in the art. The surfaces can be functionalized before or after the device is assembled. The surfaces of the device can also be coated in order to capture materials in the sample, e.g., membrane fragments or proteins.

In certain embodiments of the present disclosure, a method for fabricating any Q-Card of the present disclosure can comprise injection molding of the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise Laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise injection molding and laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise nanoimprinting or extrusion printing to fabricated both the first and the second plate. In certain embodiments of the present disclosure, a method for fabricating any Q-Card of the present disclosure can comprise fabricating the first plate or the second plate, using injection molding, laser cutting the first plate, nanoimprinting, extrusion printing, or a combination of thereof. In certain embodiments of the present disclosure, a method for fabricating any Q-Card of the present disclosure can comprise a step of attaching the hinge on the first and the second plates after the fabrication of the first and second plates.

E) Sample Types & Subjects

Details of the Samples & Subjects are described in detail in a variety of publications including International Application (IA) No. PCT/US2016/046437 filed on Aug. 10, 2016, IA No. PCT/US2016/051775 filed on Sep. 14, 2016, IA No. PCT/US201/017307 filed on Feb. 7, 2018, IA No. and PCT/US2017/065440 filed on Dec. 8, 2017, each of which is hereby incorporated by reference herein for all purposes.

A sample can be obtained from a subject. A subject as described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of subjects that can benefit is subjects who have or are suspected of having an infection (e.g., a bacterial and/or a viral infection). Another particular class of subjects that can benefit is subjects who can be at higher risk of getting an infection. Furthermore, a subject treated by any of the methods or compositions described herein can be male or female. Any of the methods, devices, or kits disclosed herein can also be performed on a non-human subject, such as a laboratory or farm animal. Non-limiting examples of a non-human subjects include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

The devices, apparatus, systems, and methods herein disclosed can be used for samples such as but not limited to diagnostic samples, clinical samples, environmental samples and foodstuff samples.

For example, in certain embodiments, the devices, apparatus, systems, and methods herein disclosed are used for a sample that includes cells, tissues, bodily fluids and/or a mixture thereof. In certain embodiments, the sample comprises a human body fluid. In certain embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In certain embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In certain embodiments, the devices, apparatus, systems, and methods herein disclosed are used for a foodstuff sample, which is suitable or has the potential to become suitable for animal consumption, e.g., human consumption. In certain embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter (uL, also "uL" herein) or less, 500 uL or less, 300 uL or less, 250 uL or less, 200 uL or less, 170 uL or less, 150 uL or less, 125 uL or less, 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the volume of the sample includes, but is not limited to, about 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values. In certain embodiments, the volume of the sample includes, but is not limited to, about 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

F) Machine Learning

Details of the Network are described in detail in a variety of publications including International Application (IA) No. PCT/US2018/017504 filed Feb. 8, 2018, and PCT/US2018/057877 filed Oct. 26, 2018, each of which are hereby incorporated by reference herein for all purposes.

One aspect of the present invention provides a framework of machine learning and deep learning for analyte detection and localization. A machine learning algorithm is an algorithm that is able to learn from data. A more rigorous definition of machine learning is "A computer program is said to learn from experience E with respect to some class of tasks T and performance measure P, if its performance at tasks in T, as measured by P, improves with experience E." It explores the study and construction of algorithms that can learn from and make predictions on data—such algorithms overcome the static program instructions by making data driven predictions or decisions, through building a model from sample inputs.

Deep learning is a specific kind of machine learning based on a set of algorithms that attempt to model high level abstractions in data. In a simple case, there might be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

One aspect of the present invention is to provide two analyte detection and localization approaches. The first approach is a deep learning approach and the second approach is a combination of deep learning and computer vision approaches.

(i) Deep Learning Approach. In the first approach, the disclosed analyte detection and localization workflow consists of two stages, training and prediction. We describe training and prediction stages in the following paragraphs.

(a) Training Stage

In the training stage, training data with annotation is fed into a convolutional neural network. Convolutional neural network is a specialized neural network for processing data that has a grid-like, feed forward and layered network topology. Examples of the data include time-series data, which can be thought of as a 1D grid taking samples at regular time intervals, and image data, which can be thought of as a 2D grid of pixels. Convolutional networks have been successful in practical applications. The name "convolutional neural network" indicates that the network employs a mathematical operation called convolution. Convolution is a specialized kind of linear operation. Convolutional networks are simply neural networks that use convolution in place of general matrix multiplication in at least one of their layers.

The machine learning model receives one or multiple images of samples that contain the analytes taken by the imager over the sample holding QMAX device as training data. Training data are annotated for analytes to be assayed, wherein the annotations indicate whether or not analytes are in the training data and where they locate in the image. Annotation can be done in the form of tight bounding boxes which fully contains the analyte, or center locations of analytes. In the latter case, center locations are further converted into circles covering analytes or a Gaussian kernel in a point map.

When the size of training data is large, training machine learning model presents two challenges: annotation (usually done by human) is time consuming, and the training is computationally expensive. To overcome these challenges, one can partition the training data into patches of small size, then annotate and train on these patches, or a portion of these patches. The term "machine learning" can refer to algorithms, systems and apparatus in the field of artificial intelligence that often use statistical techniques and artificial neural network trained from data without being explicitly programmed.

The annotated images are fed to the machine learning (ML) training module, and the model trainer in the machine learning module will train a ML model from the training data (annotated sample images). The input data will be fed to the model trainer in multiple iterations until certain stopping criterion is satisfied. The output of the ML training module is a ML model—a computational model that is built from a training process in the machine learning from the data that gives computer the capability to perform certain tasks (e.g. detect and classify the objects) on its own.

The trained machine learning model is applied during the predication (or inference) stage by the computer. Examples of machine learning models include ResNet, DenseNet, etc. which are also named as "deep learning models" because of the depth of the connected layers in their network structure. In certain embodiments, the Caffe library with fully convolutional network (FCN) was used for model training and predication, and other convolutional neural network architecture and library can also be used, such as TensorFlow.

The training stage generates a model that will be used in the prediction stage. The model can be repeatedly used in the prediction stage for assaying the input. Thus, the computing unit only needs access to the generated model. It does not need access to the training data, nor requiring the training stage to be run again on the computing unit.

(b) Prediction Stage

In the predication/inference stage, a detection component is applied to the input image, and an input image is fed into the predication (inference) module preloaded with a trained model generated from the training stage. The output of the prediction stage can be bounding boxes that contain the detected analytes with their center locations or a point map indicating the location of each analyte, or a heatmap that contains the information of the detected analytes.

When the output of the prediction stage is a list of bounding boxes, the number of analytes in the image of the sample for assaying is characterized by the number of detected bounding boxes. When the output of the prediction stage is a point map, the number of analytes in the image of the sample for assaying is characterized by the integration of the point map. When the output of the prediction is a heatmap, a localization component is used to identify the location and the number of detected analytes is characterized by the entries of the heatmap.

One embodiment of the localization algorithm is to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

In the detection component using heatmap, an input image, along with the model generated from the training stage, is fed into a convolutional neural network, and the output of the detection stage is a pixel-level prediction, in the form of a heatmap. The heatmap can have the same size as the input image, or it can be a scaled down version of the input image, and it is the input to the localization component. We disclose an algorithm to localize the analyte center. The main idea is to iteratively detect local peaks from the heatmap. After the peak is localized, we calculate the local area surrounding the peak but with smaller value. We remove this region from the heatmap and find the next peak from the remaining pixels. The process is repeated only all pixels are removed from the heatmap.

In certain embodiments, the present invention provides the localization algorithm to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

```
Algorithm GlobalSearch (heatmap)
Input:
    heatmap
Output:
    loci
loci ←{ }
sort(heatmap)
while (heatmap is not empty) {
    s ← pop(heatmap)
    D ← {disk center as s with radius R}
    heatmap = heatmap \ D // remove D from the heatmap
    add s to loci
}
```

After sorting, heatmap is a one-dimensional ordered list, where the heatmap value is ordered from the highest to the lowest. Each heatmap value is associated with its corresponding pixel coordinates. The first item in the heatmap is the one with the highest value, which is the output of the pop(heatmap) function. One disk is created, where the center is the pixel coordinate of the one with highest heatmap value. Then all heatmap values whose pixel coordinates resides inside the disk is removed from the heatmap. The algorithm repeatedly pops up the highest value in the current heatmap, removes the disk around it, till the items are removed from the heatmap.

In the ordered list heatmap, each item has the knowledge of the proceeding item, and the following item. When removing an item from the ordered list, we make the following changes:

Assume the removing item is $x_r$, its proceeding item is $x_p$, and its following item is $x_f$.

For the proceeding item $x_p$, re-define its following item to the following item of the removing item. Thus, the following item of $x_p$ is now $x_f$.

For the removing item $x_r$, un-define its proceeding item and following item, which removes it from the ordered list.

For the following item $x_f$, re-define its proceeding item to the proceeding item of the removed item. Thus, the proceeding item of $x_f$ is now $x_p$.

After all items are removed from the ordered list, the localization algorithm is complete. The number of elements in the set loci will be the count of analytes, and location information is the pixel coordinate for each s in the set loci.

Another embodiment searches local peak, which is not necessary the one with the highest heatmap value. To detect each local peak, we start from a random starting point, and search for the local maximal value. After we find the peak, we calculate the local area surrounding the peak but with smaller value. We remove this region from the heatmap and find the next peak from the remaining pixels. The process is repeated only all pixels are removed from the heatmap.

```
Algorithm LocalSearch (s, heatmap)
Input:
    s: starting location (x, y)
    heatmap
Output:
    s: location of local peak.
We only consider pixels of value > 0.
Algorithm Cover (s, heatmap)
Input:
    s: location of local peak.
    heatmap:
Output:
    cover: a set of pixels covered by peak:
```

This is a breadth-first-search algorithm starting from s, with one altered condition of visiting points: a neighbor p of the current location q is only added to cover if heatmap[p]>0 and heatmap[p]<=heatmap[q]. Therefore, each pixel in cover has a non-descending path leading to the local peak s.

```
Algorithm Localization (heatmap)
Input:
    heatmap
Output:
    loci
loci ←{ }
pixels ←{all pixels from heatmap}
while pixels is not empty {
    s ←any pixel from pixels
    s ←LocalSearch(s, heatmap)   // s is now local peak
    probe local region of radius R surrounding s for better local peak
    r ←Cover(s, heatmap)
    pixels ← pixels \ r          // remove all pixels in cover
    add s to loci
```

(ii) Mixture of Deep Learning and Computer Vision Approaches. In the second approach, the detection and localization are realized by computer vision algorithms, and a classification is realized by deep learning algorithms, wherein the computer vision algorithms detect and locate possible candidates of analytes, and the deep learning algorithm classifies each possible candidate as a true analyte and false analyte. The location of all true analyte (along with the total count of true analytes) will be recorded as the output.

(a) Detection. The computer vision algorithm detects possible candidate based on the characteristics of analytes, including but not limited to intensity, color, size, shape, distribution, etc. A pre-processing scheme can improve the detection. Pre-processing schemes include contrast enhancement, histogram adjustment, color enhancement, de-nosing, smoothing, de-focus, etc. After pre-processing, the input image is sent to a detector. The detector tells the existing of possible candidate of analyte and gives an estimate of its location. The detection can be based on the analyte structure (such as edge detection, line detection, circle detection, etc.), the connectivity (such as blob detection, connect components, contour detection, etc.), intensity, color, shape using schemes such as adaptive thresholding, etc.

(b) Localization. After detection, the computer vision algorithm locates each possible candidate of analytes by providing its boundary or a tight bounding box containing it. This can be achieved through object segmentation algorithms, such as adaptive thresholding, background subtraction, floodfill, mean shift, watershed, etc. Very often, the localization can be combined with detection to produce the detection results along with the location of each possible candidates of analytes.

(c) Classification. The deep learning algorithms, such as convolutional neural networks, achieve start-of-the-art visual classification. We employ deep learning algorithms for classification on each possible candidate of analytes. Various convolutional neural network can be utilized for analyte classification, such as VGGNet, ResNet, MobileNet, DenseNet, etc.

Given each possible candidate of analyte, the deep learning algorithm computes through layers of neurons via convolution filters and non-linear filters to extract high-level features that differentiate analyte against non-analytes. A layer of fully convolutional network will combine high-level features into classification results, which tells whether it is a true analyte or not, or the probability of being a analyte.

G) Applications, Bio/Chemical Biomarkers, and Health Conditions

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled condensate.

In embodiments, the sample is at least one of a biological sample, an environmental sample, and a biochemical sample.

The devices, systems and the methods in the present invention find use in a variety of different applications in various fields, where determination of the presence or absence, and/or quantification of one or more analytes in a sample are desired. For example, the subject method finds use in the detection of proteins, peptides, nucleic acids, synthetic compounds, inorganic compounds, and the like. The various fields include, but not limited to, human, veterinary, agriculture, foods, environments, drug testing, and others.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present inventions of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

An implementation of the devices, systems and methods in the present invention can include a) obtaining a sample, b) applying the sample to CROF device containing a capture agent that binds to an analyte of interest, under conditions suitable for binding of the analyte in a sample to the capture agent, c) washing the CROF device, and d) reading the CROF device, thereby obtaining a measurement of the amount of the analyte in the sample. In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the CROF device can be placed in a microfluidic device and the applying step b) can include applying a sample to a microfluidic device comprising the CROF device.

In any embodiment, the reading step d) can include detecting a fluorescence or luminescence signal from the CROF device.

In any embodiment, the reading step d) can include reading the CROF device with a handheld device configured to read the CROF device. The handheld device can be a mobile phone, e.g., a smart phone.

In any embodiment, the CROF device can include a labeling agent that can bind to an analyte-capture agent complex on the CROF device.

In any embodiment, the devices, systems and methods in the present invention can further include, between steps c) and d), the steps of applying to the CROF device a labeling agent that binds to an analyte-capture agent complex on the CROF device, and washing the CROF device.

In any embodiment, the reading step d) can include reading an identifier for the CROF device. The identifier can be an optical barcode, a radio frequency ID tag, or combinations thereof.

In any embodiment, the devices, systems and methods in the present invention can further include applying a control sample to a control CROF device containing a capture agent that binds to the analyte, wherein the control sample includes a known detectable amount of the analyte, and reading the control CROF device, thereby obtaining a control measurement for the known detectable amount of the analyte in a sample.

In any embodiment, the sample can be a diagnostic sample obtained from a subject, the analyte can be a biomarker, and the measured amount of the analyte in the sample can be diagnostic of a disease or a condition.

In any embodiment, the devices, systems and methods in the present invention can further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In any embodiment, the devices, systems and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the applying step b) can include isolating miRNA from the sample to generate an isolated miRNA sample, and applying the isolated miRNA sample to the disk-coupled dots-on-pillar antenna (CROF device) array.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the CROF device array can include a plurality of capture agents that each binds to an environmental marker, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the CROF device array can include a plurality of capture agents that each binds to a foodstuff marker, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the CROF device can be employed. Suitable methods can include using a pipet, dropper, syringe, etc. In certain embodiments, when the CROF device is located on a support in a dipstick format, as described below, the sample can be applied to the CROF device by dipping a sample-receiving area of the dipstick into the sample.

A sample can be collected at one time, or at a plurality of times. Samples collected over time can be aggregated and/or processed (by applying to a CROF device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the CROF device to remove unbound sample components can be done in any convenient manner, as described above. In certain embodiments, the surface of the CROF device is washed using binding buffer to remove unbound sample components.

Detectable labeling of the analyte can be done by any convenient method. The analyte can be labeled directly or indirectly. In direct labeling, the analyte in the sample is labeled before the sample is applied to the CROF device. In indirect labeling, an unlabeled analyte in a sample is labeled after the sample is applied to the CROF device to capture the unlabeled analyte, as described below.

The samples from a subject, the health of a subject, and other applications of the present invention are further described below. Exemplary samples, health conditions, and application are also disclosed in, e.g., U.S. Pub. Nos. 2014/0154668 and 2014/0045209, which are hereby incorporated by reference.

The present inventions find use in a variety of applications, where such applications are generally analyte detection applications in which the presence of a particular analyte in a given sample is detected at least qualitatively, if not quantitatively. Protocols for carrying out analyte detection assays are well known to those of skill in the art and need not be described in great detail here. Generally, the sample suspected of comprising an analyte of interest is contacted with the surface of a subject nanosensor under conditions sufficient for the analyte to bind to its respective capture agent that is tethered to the sensor. The capture agent has highly specific affinity for the targeted molecules of interest. This affinity can be antigen-antibody reaction where antibodies bind to specific epitope on the antigen, or a DNA/RNA or DNA/RNA hybridization reaction that is sequence-specific between two or more complementary strands of nucleic acids. Thus, if the analyte of interest is present in the sample, it likely binds to the sensor at the site of the capture agent and a complex is formed on the sensor surface. Namely, the captured analytes are immobilized at the sensor surface. After removing the unbounded analytes, the presence of this binding complex on the surface of the sensor (e.g., the immobilized analytes of interest) is then detected, e.g., using a labeled secondary capture agent.

Specific analyte detection applications of interest include hybridization assays in which the nucleic acid capture agents are employed and protein binding assays in which polypeptides, e.g., antibodies, are employed. In these assays, a sample is first prepared and following sample preparation, the sample is contacted with a subject nanosensor under specific binding conditions, whereby complexes are formed between target nucleic acids or polypeptides (or other molecules) that are complementary to capture agents attached to the sensor surface.

In one embodiment, the capture oligonucleotide is synthesized single strand DNA of 20-100 bases length, that is thiolated at one end. These molecules are are immobilized on the nanodevices' surface to capture the targeted single-strand DNA (which can be at least 50 bp length) that has a sequence that is complementary to the immobilized capture DNA. After the hybridization reaction, a detection single strand DNA (which can be of 20-100 bp in length) whose sequence are complementary to the targeted DNA's unoccupied nucleic acid is added to hybridize with the target. The detection DNA has its one end conjugated to a fluorescence label, whose emission wavelength are within the plasmonic resonance of the nanodevice. Therefore by detecting the fluorescence emission emanate from the nanodevices' surface, the targeted single strand DNA can be accurately detected and quantified. The length for capture and detection DNA determine the melting temperature (nucleotide strands will separate above melting temperature), the extent of misparing (the longer the strand, the lower the misparing).

One of the concerns of choosing the length for complementary binding depends on the needs to minimize misparing while keeping the melting temperature as high as possible. In addition, the total length of the hybridization length is determined in order to achieve optimum signal amplification.

A subject sensor can be employed in a method of diagnosing a disease or condition, comprising: (a) obtaining a liquid sample from a patient suspected of having the disease or condition, (b) contacting the sample with a subject nanosensor, wherein the capture agent of the nanosensor specifically binds to a biomarker for the disease and wherein the contacting is done under conditions suitable for specific binding of the biomarker with the capture agent; (c) removing any biomarker that is not bound to the capture agent; and (d) reading a light signal from biomarker that remain bound to the nanosensor, wherein a light signal indicates that the patient has the disease or condition, wherein the method further comprises labeling the biomarker with a light-emitting label, either prior to or after it is bound to the capture agent. As will be described in greater detail below, the patient can suspected of having cancer and the antibody binds to a cancer biomarker. In other embodiments, the patient is suspected of having a neurological disorder and the antibody binds to a biomarker for the neurological disorder.

The applications of the subject sensor include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

In some embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

In some cases, the nanosensor can be employed to detect a biomarker that is present at a low concentration. For example, the nanosensor can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example. The following table provides a list of protein biomarkers that can be detected using the subject nanosensor (when used in conjunction with an appropriate monoclonal antibody), and their associated diseases. One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva.

H) Utility

The subject method finds use in a variety of different applications where determination of the presence or absence, and/or quantification of one or more analytes in a sample are desired. For example, the subject method finds use in the detection of proteins, peptides, nucleic acids, synthetic compounds, inorganic compounds, and the like.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present invention of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

I) Diagnostic Method

In certain embodiments, the subject method finds use in detecting biomarkers. In some embodiments, the devices, systems and methods in the present invention of using CROF are used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like. Thus, the sample, e.g. a diagnostic sample, can include various fluid or solid samples.

In some instances, the sample can be a bodily fluid sample from a subject who is to be diagnosed. In some instances, solid or semi-solid samples can be provided. The sample can include tissues and/or cells collected from the subject. The sample can be a biological sample. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate and/or other excretions. The samples can include nasopharyngeal wash. Nasal swabs, throat swabs, stool samples, hair, finger nail, ear wax, breath, and other solid, semi-solid, or gaseous samples can be processed in an extraction buffer, e.g., for a fixed or variable amount of time, prior to their analysis. The extraction buffer or an aliquot thereof can then be processed similarly to other fluid samples if desired. Examples of tissue samples of the subject can include but are not limited to, connective tissue, muscle tissue, nervous tissue, epithelial tissue, cartilage, cancerous sample, or bone.

In some instances, the subject from which a diagnostic sample is obtained can be a healthy individual, or can be an individual at least suspected of having a disease or a health condition. In some instances, the subject can be a patient.

In certain embodiments, the CROF device includes a capture agent configured to specifically bind a biomarker in a sample provided by the subject. In certain embodiments, the biomarker can be a protein. In certain embodiments, the biomarker protein is specifically bound by an antibody capture agent present in the CROF device. In certain embodiments, the biomarker is an antibody specifically bound by an antigen capture agent present in the CROF device. In certain embodiments, the biomarker is a nucleic acid specifically bound by a nucleic acid capture agent that is complementary to one or both strands of a double-stranded nucleic acid biomarker, or complementary to a single-stranded biomarker. In certain embodiments, the biomarker is a nucleic acid specifically bound by a nucleic acid binding protein. In certain embodiments, the biomarker is specifically bound by an aptamer.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers can influence the choices of drug treatment or administration regimes given to an individual. In evaluating potential drug therapies, a biomarker can be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject method. Furthermore, the early detection of biomarkers associated with diseases is facilitated by the high sensitivity of the devices, systems and methods in the present invention, as described above. Due to the capability of detecting multiple biomarkers with a mobile device, such as a smartphone, combined with sensitivity, scalability, and ease of use, the presently disclosed method finds use in portable and point-of-care or near-patient molecular diagnostics.

In certain embodiments, the subject method finds use in detecting biomarkers for a disease or disease state. In certain instances, the subject method finds use in detecting biomarkers for the characterization of cell signaling pathways and intracellular communication for drug discovery and vaccine development. For example, the subject method can be used to detect and/or quantify the amount of biomarkers in diseased, healthy or benign samples. In certain embodiments, the subject method finds use in detecting biomarkers for an infectious disease or disease state. In some cases, the biomarkers can be molecular biomarkers, such as but not limited to proteins, nucleic acids, carbohydrates, small molecules, and the like.

The subject method find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

In some embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

Other pathogens that can be detected in a diagnostic sample using the devices, systems and methods in the present invention include, but are not limited to: Varicella zoster; *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*; gonorrhea (*Neisseria gorrhoeae*), syphilis (*Treponena pallidum*), clamydia (*Clamyda tracomitis*), nongonococcal urethritis (*Ureaplasm urealyticum*), chancroid (*Haemophilus ducreyi*), trichomoniasis (*Trichomonas vaginalis*); *Pseudomonas aeruginosa*, methicillin-resistant *Staphylococcus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*, etc.

In some cases, the CROF device can be employed to detect a biomarker that is present at a low concentration. For example, the CROF device can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva. It will also be clear to one with ordinary skill in the art that the subject CROF devices can be configured to capture and detect many more biomarkers known in the art that are diagnostic of a disease or health condition.

A biomarker can be a protein or a nucleic acid (e.g., mRNA) biomarker, unless specified otherwise. The diagnosis can be associated with an increase or a decrease in the level of a biomarker in the sample, unless specified otherwise. Lists of biomarkers, the diseases that they can be used to diagnose, and the sample in which the biomarkers can be detected are described in Tables 1 and 2 of U.S. provisional application Ser. No. 62/234,538, filed on Sep. 29, 2015, which application is incorporated by reference herein.

In some instances, the devices, systems and methods in the present invention is used to inform the subject from whom the sample is derived about a health condition thereof. Health conditions that can be diagnosed or measured by the devices, systems and methods in the present invention, device and system include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause. Table 3 of U.S. provisional application Ser. No. 62/234,538, filed on Sep. 29, 2015, which application is incorporated by reference herein, provides a list of biomarker that can be detected using the present CROF device (when used in conjunction with an appropriate monoclonal antibody, nucleic acid, or other capture agent), and their associated health conditions.

J) Kits

Aspects of the present disclosure include a kit that find use in performing the devices, systems and methods in the present invention, as described above. In certain embodiments, the kit includes instructions for practicing the subject methods using a hand held device, e.g., a mobile phone. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that can be present is a website address which can be used via the Internet to access the information at a removed site. The kit can further include a software for implementing a method for measuring an analyte on a device, as described herein, provided on a computer readable medium. Any convenient means can be present in the kits.

In some embodiments, the kit includes a detection agent that includes a detectable label, e.g. a fluorescently labeled antibody or oligonucleotide that binds specifically to an analyte of interest, for use in labeling the analyte of interest. The detection agent can be provided in a separate container as the CROF device, or can be provided in the CROF device.

In some embodiments, the kit includes a control sample that includes a known detectable amount of an analyte that is to be detected in the sample. The control sample can be provided in a container, and can be in solution at a known concentration, or can be provided in dry form, e.g., lyophilized or freeze dried. The kit can also include buffers for use in dissolving the control sample, if it is provided in dry form.

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No.

62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Other Embodiments

Further examples of inventive subject matter according to the present disclosure are described in the following enumerated paragraphs.

It must be noted that, as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed. The term "about" has the meaning as commonly understood by one of ordinary skill in the art. In some embodiments, the term "about" refers to ±10%. In some embodiments, the term "about" refers to ±5%.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function can additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") can refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, e.g., "one or more" of the entity so conjoined. Other entity can optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

What is claimed is:

1. A method for performing a competitive assay of an analyte in a liquid sample, comprising:
   (a) providing a liquid sample that contains or is suspected of containing an analyte;

(b) providing one or more beads that have a capture agent attached onto the surface of the one or more beads, wherein the capture agent specifically binds to the analyte;

(c) providing a labeled competitive detection agent, wherein the labeled competing detection agent competes with the analyte, if present, for binding to the capture agent;

(d) providing a sample holder that is capable of making the liquid sample into a thin layer;

(e) having the liquid sample in the sample holder and making the liquid sample form a thin layer having a thickness of 200 um or less, wherein the one or more beads and the labeled competitive detection agent are mixed with the liquid sample;

(f) taking, after step (e), without washing the liquid sample, at least two images, including a first image and a second image, of a common area of the sample layer, wherein the common area of the sample layer is an area of the liquid sample that contains at least one bead, wherein the first image is a direct image for measuring a position of a bead in the common area; and the second image is a signal image for measuring a signal from the labeled competitive detection agent; and (g) after (f), comparing and analyzing the first image and the second image to identify the signal at the one or more beads;

wherein the beads have various shape and have a dimension in the range of 0.05 um to 50 um, wherein the spacing in the sample holder is such that in the common area (i) the sample layer has uniform thickness, and (ii) the one or more beads do not overlap with each other in a direction normal to the sample layer such that when viewing from the top of the sample layer, no bead substantially blocks a view of any other bead.

2. A method for performing a competitive assay of an analyte in a liquid sample, comprising:

(a) providing a liquid sample that contains or is suspected of containing an analyte;

(b) providing one or more beads that have a capture agent attached onto the surface of the beads;

(c) providing a labeled competitive detection agent, wherein the labeled competing detection agent specifically binds to the analyte and the capture agent, and wherein the capture agent competes with the analyte, if present, for binding to the labeled competing detection agent;

(d) providing a sample holder that is capable of making the liquid sample into a thin layer having a thickness of 200 um or less;

(e) having the liquid sample in the sample holder and making the liquid sample form a thin layer, wherein the beads and the labeled competitive detection agent are mixed with the liquid sample;

(f) taking, after step (e), without washing the liquid sample, at least two images, including a first image and a second image, of a common area of the thin sample layer, wherein the common area of the thin sample layer is an area of the sample that contains at least one bead, wherein the first image is a direct image for measuring a position of a bead in the common area; and the second image is a signal image for measuring a signal from the labeled competitive detection agent; and (g) after (f), comparing and analyzing the first image and the second image to identify the signal at the beads;

wherein the beads and have a dimension in the range of 0.05 um to 50 um, wherein the spacing in the sample holder is uniform such that in the common area (i) the sample layer has uniform thickness, and (ii) the one or more beads do not overlap with each other in a direction normal to the sample layer such that when viewing from the top of the sample layer, no bead substantially blocks a view of any other bead.

3. A method for assaying an analyte in a liquid sample using beads, comprising:

(a) depositing a liquid sample that contains or is suspected of containing an analyte, into a sample holder, said sample holder comprising:
  i. a first plate having an inner surface; and
  ii. a second plate having an inner surface;

wherein the first plate and the second plate are movable relative to each other into:
  i. an open configuration in which the first plate and the second plate are at least partially separated such that the liquid sample can be deposited therebetween; and
  ii. a closed configuration, in which the first plate is placed on top of the second plate thereby compressing at least a portion of the liquid sample between the first plate and the second plate into a sample layer having uniform thickness of 200 um or less;

(b) having the plates into a closed configuration, wherein the liquid sample is mixed with (i) one or more beads comprising a capture agent attached onto a surface thereof; and (ii) a labeled competitive detection agent;

(c) taking, after step (b), while the plates are in the closed configuration and without washing the liquid sample, at least two images, including a first image and a second image, of a common area of the sample layer, wherein the common area of the sample layer is an area of the liquid sample that contains at least one bead, wherein the first image is a direct image for measuring a position of a bead in the common area, and wherein the second image is a signal image for measuring a signal from the labeled competitive detection agent; and (d) after (c), comparing and analyzing the first image and the second image to identify the signal at the beads;

wherein the beads have a dimension in the range of 0.05 um to 50 um, wherein the spacing between the inner surfaces of the two plates is uniform such that in the common area (i) the sample layer has uniform thickness, and (ii) the one or more beads do not overlap with each other in a direction normal to the sample layer such that when viewing from the top of the sample layer, no bead substantially blocks a view of any other bead.

4. The method of claim 3, wherein the common area of the sample is an area of the sample comprising at least one of the one or more beads.

5. The method of claim 3, wherein one of the two or more images is a direct image.

6. The method of claim 5, wherein the direct image comprises information of the topology and position of the beads in the common area.

7. The method of claim 3, wherein the capture agent specifically binds to the analyte.

8. The method of claim 3, wherein the labeled competing detection agent competes with the analyte, if present, for binding to the capture agent for the analyte.

9. The method of claim 3, further comprising comparing and analyzing the two or more images and using an algorithm to identify the signal at the beads.

10. The method of claim 3, wherein the beads have a different shape.

11. The method of claim 3, wherein the sample holder further comprises spacers disposed on at least one of the first plate and the second plate.

12. The method of claim 11, wherein the wherein the thickness of the layer is regulated by the spacers.

13. A kit for performing a competitive assay for analyzing an analyte in a sample, comprising:
a first plate, a second plate, one or plurality of beads, a capture agent, a labeled competing detection agent, and an imager, wherein:
i. the plates are movable relative to each other into different configurations;
ii. each of the plates has, on its respective surface, a sample contact area for contacting a sample that contains or is suspected of containing an analyte;
iii. the beads have a capture agent attached onto the surface of the beads, wherein the capture agent specifically bind to the analyte;
iv. the labeled competing detection agent competes with the analyte, if present, for binding to the capture agent for the analyte; and
v. the beads have a size of 0.2 urn to 100 µm;
wherein one of the configurations is an open configuration, in which: the two plates are separated apart, and the sample is deposited on one or both plate;
wherein another of the configurations is a closed configuration which is configured after the sample deposition in the open configuration; and in the closed configuration: at least part of the sample is compressed by the two plates into a layer of highly uniform thickness of 200 µm or less and is substantially stagnant relative to the plates;
wherein at the closed configuration, a detector detects the analyte in the at least part of the sample; and
wherein the imager takes, at least two images, including a first image and a second image, of a common area of the thin sample layer, wherein the common area of the thin sample layer is an area of the sample that contains at least one bead, wherein the first image is a direct image for measuring a position of a bead in the common area; and the second image is a signal image for measuring a signal from the labeled competitive detection agent.

14. The kit of claim 13, wherein the direct image is bright field image.

15. The kit of claim 13, wherein the direct image is an image formed with an illumination from an angle of 0 to 30 degrees from the normal of the sample thin layer.

16. The kit of claim 13, wherein the signal image is a dark field image.

17. The kit of claim 13, wherein the signal image is a fluorescence image.

18. The kit of claim 13, wherein the signal image is an image formed with an illumination from an angle of 0 to 30 degrees parallel to the sample thin layer.

19. The kit of claim 13, wherein the assay is a homogeneous assay that measures the analyte and does not use any wash.

20. The kit of claim 13, wherein the beads have a diameter in a range of 5 µm to 50 µm.

21. The kit of claim 13, wherein the beads can be polystyrene, polypropylene, polycarbonate, glass, metal or any other material whose surface can be modified to bind antibodies.

22. The kit of claim 13, wherein one or both plates have one or more spacers and the diameter of the beads is about the same as a height of the one or more spacers.

23. The kit of claim 22, wherein the diameter of the beads is equal or less than the height of the one or more spacers.

24. The kit of claim 13, wherein the labels is selected from the group consisting of a fluorescent label, a colorimetric label, and luminescent label.

25. The kit of claim 13, wherein the detection agent is coated on the inner surface(s) of one or both of the plates, and is configured to, upon contacting the sample, be dissolved and diffuse in the sample.

26. The kit of claim 13, wherein the detection agent is pre-loaded into the sample before the sample is deposited on the plate(s).

27. The kit of claim 13, wherein one or both of the plates further comprise, on the respective inner surface, a signal amplification surface that amplify the signal in proximity to the amplification surface.

28. The kit of claim 13, wherein the beads and the detection agent are on the same plate.

29. The kit of claim 13, wherein the beads and the detection agent are on different plates.

30. The kit of claim 13, wherein the analyte is selected from the group consisting of: cells, viruses, proteins, peptides, DNAs, RNAs, oligonucleotides, and any combination thereof.

31. The kit of claim 13, wherein the analyte is C Reactive Protein (CRP).

32. The kit of claim 13, wherein the capture agent is selected from the group consisting of: protein, peptide, peptidomimetics, streptavidin, biotin, oligonucleotide, oligonucleotide mimetics, any other affinity ligand and any combination thereof.

33. The kit of claim 13, wherein the capture agent is an antibody.

34. The kit of claim 13, wherein the detection agent is selected from the group consisting of: protein, peptide, peptidomimetics, streptavidin, biotin, oligonucleotide, oligonucleotide mimetics, any other affinity ligand and any combination thereof.

35. The kit of claim 13, wherein the detection agent is an antibody.

36. The kit of claim 13, wherein the beads are prepared by:
a. activating with N-Hydroxysuccinimide (NETS);
b. blocking with a BSA solution; and
c. incubating with a capture agent solution.

37. The kit of claim 13, wherein the sample is a biological sample selected from the group consisting of: amniotic fluid, aqueous humour, vitreous humour, blood, breast milk, cerebrospinal fluid (CSF), cerumen (earwax), chyle, chime, endolymph, perilymph, feces, breath, gastric acid, gastric juice, lymph, mucus, pericardial fluid, peritoneal fluid, pleural fluid, pus, rheum, saliva, exhaled breath condensates, sebum, semen, sputum, sweat, synovial fluid, tears, vomit, urine, and any combination thereof.

38. The kit of claim 13, wherein the sample is an environmental liquid sample selected from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

39. The kit of claim 13, wherein the sample is an environmental gaseous sample from a source selected from the group consisting of: the air, underwater heat vents, industrial exhaust, vehicular exhaust, and any combination thereof.

40. The kit of claim 13, wherein the sample is a foodstuff sample selected from the group consisting of: raw ingredients, cooked food, plant and animal sources of food, pre-processed food, and partially or fully processed food, and any combination thereof.

41. The kit of claim 13, wherein the beads are associated with a label, and wherein the detection agent is a quencher that is configured to quench signal of the beads-associated label when the detection agent is in proximity of the label.

42. The kit of claim 13, wherein the detector detects the signal emanating from the analyte concentration areas or beads indicative of the presence and/or quantity of the analyte.

43. The kit of claim 13, wherein the signal is:
  i. luminescence selected from the group consisting of photoluminescence, electroluminescence, and electrochemiluminescence;
  ii. light absorption, reflection, transmission, diffraction, scattering, or diffusion;
  iii. surface Raman scattering;
  iv. electrical impedance selected from the group consisting of resistance, capacitance, and inductance;
  v. magnetic relaxivity; or
  vi. any combination of i-v.

44. A kit for performing a competitive assay for analyzing an analyte in a sample, comprising:
  a first plate, a second plate, one or plurality of beads, a capture agent, a labeled competing detection agent, spacers, an imager, wherein:
    i. the plates are movable relative to each other into different configurations;
    ii. each of the plates has, on its respective inner surface, a sample contact area for contacting a sample that contains or is suspected an analyte;
    iii. the beads have a capture agent attached to the surface of the beads, wherein the capture agent specifically bind to the analyte;
    iv. the labeled competing detection agent competes with the analyte, if present, for binding to the capture agent for the analyte;
    v. the spacers are on one or both of the plates, wherein the spacers are fixed on one of the plates and have a flat top, and in at least one of the spacers is in the sample area; and
    vi. the beads have a capture agent attached on their surface and have a size of 0.2 µm to 100 µm;
  wherein one of the configurations is an open configuration, in which: the two plates are separated apart, the spacing between the plates is not regulated by the spacers, and the sample is deposited on one or both of the plates;
  wherein another of the configurations is a closed configuration which is configured after the sample deposition in the open configuration; and in the closed configuration: at least part of the sample is compressed by the two plates into a layer of highly uniform thickness of 200 µm or less and is substantially stagnant relative to the plates, wherein the uniform thickness of the layer is confined by the inner surfaces of the two plates and is regulated by the plates and the spacers; and
  wherein the imager takes, at least two images, including a first image and a second image, of a common area of the thin sample layer, wherein the common area of the thin sample layer is an area of the sample that contains at least one bead, wherein the first image is a direct image for measuring a position of a bead in the common area; and the second image is a signal image for measuring a signal from the labeled competitive detection agent.

45. The kit of claim 44, wherein the beads regulate the thickness of the layer at the closed configuration.

46. The kit of claim 44, wherein the analyte is selected from the group consisting of proteins, peptides, nucleic acids, synthetic compounds, and inorganic compounds.

47. The kit of claim 44, wherein the spacers have a shape of pillars and a ratio of the width to the height of the pillar is equal or larger than one.

48. The kit of claim 44, wherein the samples is related to infectious and parasitic disease, injuries, cardiovascular disease, cancer, mental disorders, neuropsychiatric disorders, pulmonary diseases, renal diseases, and other and organic diseases.

49. The kit of claim 44, wherein the samples are related to the detection, purification and quantification of microorganism.

50. The kit of claim 44, wherein the samples is related to virus, fungus and bacteria from environment.

51. The kit of claim 44, wherein the sample is related to the detection, quantification of chemical compounds or biological samples that pose hazard to food safety or national security.

52. The kit of claim 44, wherein the samples are related to quantification of vital parameters in medical or physiological monitor.

53. The kit of claim 44, wherein the samples are related to glucose, blood, oxygen level, total blood count.

54. The kit of claim 44, wherein the samples are related to the detection and quantification of specific DNA or RNA from biosamples.

55. The kit of claim 44, wherein the samples are related to the sequencing and comparing of genetic sequences in DNA in the chromosomes and mitochondria for genome analysis.

56. The kit of claim 44, wherein the samples are related to detect reaction products.

57. The kit of claim 44, wherein the samples are cells, tissues, bodily fluids, and stool.

58. The kit of claim 44, wherein the sample is the sample in the fields of human, veterinary, agriculture, foods, environments, and drug testing.

59. The kit of claim 44, wherein the sample is a biological sample selected from the group consisting of blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, and bone.

60. A device for performing a homogeneous assay, comprising:
  a first plate, a second plate, and spacers, wherein:
    i. the plates are movable relative to each other into different configurations, including an open configuration and a closed configuration;

ii. each of the plates has, on its respective inner surface, a sample contact area for contacting a sample suspected of comprising an analyte;
iii. one or both of the plates comprise the spacers, at least one of the spacers is inside the sample contact area, and the spacers have a predetermined substantially uniform height; and
iv. one or both of the plates comprise, on the respective inner surface, a plurality of beads that have capture agent immobilized thereon, wherein the capture agent is capable of binding to and immobilizing the analyte;
wherein in the open configuration, the two plates are partially or entirely separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers, the analyte in the layer of uniform thickness is concentrated by the beads so that signal of the captured analyte on the beads is distinguishable from signal emanating from other area in the layer of uniform thickness.

61. A device for performing a homogeneous assay, comprising:
a first plate, a second plate, and spacers, wherein:
i. the plates are movable relative to each other into different configurations, including an open configuration and a closed configuration;
ii. each of the plates has, on its respective inner surface, a sample contact area for contacting a sample suspected of comprising an analyte;
iii. one or both of the plates comprise the spacers, at least one of the spacers is inside the sample contact area, and the spacers have a predetermined substantially uniform height; and
iv. one or both of the plates comprise, on the respective inner surface, a plurality of beads that have capture agent immobilized thereon, wherein the capture agent is capable of binding to and immobilizing the analyte;
wherein the spacers have a height that is equal to or less than 3 times of a diffusion parameter, wherein the diffusion parameter is square root of the intended assay time multiplying diffusion constant of the analyte in the sample and wherein the intended assay time is equal to or less than 240 seconds;
wherein the average distance between two neighboring beads is equal to or less than 2 times of the diffusion parameter;
wherein in the open configuration, the two plates are partially or entirely separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers and the analyte in the layer of uniform thickness is concentrated in the concentration area so that signal of captured analyte in the concentration areas is distinguishable from signal emanating from non-concentration area in the layer of uniform thickness.

62. A method, comprising:
(a) depositing a sample that contains or is suspected of containing an analyte, into a sample holder, said sample holder comprising:
iii. a first plate; and
iv. a second plate;
wherein the first plate and the second plate are movable relative to each other into:
iii. an open configuration in which the first plate and the second plate are at least partially separated such that the sample can be deposited therebetween; and
iv. a closed configuration, in which the first plate is placed on top of the second plate thereby compressing at least a portion of the sample between the first plate and the second plate into a layer having uniform thickness;
wherein the sample is mixed with:
i. one or more beads comprising a capture agent attached onto a surface thereof; and
ii. a labeled competitive detection agent; and
(b) obtaining two or more images of a common area of the sample.

* * * * *